United States Patent [19]
Takeshima et al.

[11] Patent Number: 5,548,124
[45] Date of Patent: Aug. 20, 1996

[54] DECAY CHARACTERISTIC MEASURING APPARATUS

[75] Inventors: Akira Takeshima; Musubu Koishi, both of Hamamatsu, Japan

[73] Assignee: Hamamatsu Photonics K.K., Hamamatsu, Japan

[21] Appl. No.: 519,422

[22] Filed: Aug. 25, 1995

[30] Foreign Application Priority Data

Sep. 19, 1994 [JP] Japan .................................. 6-223628

[51] Int. Cl.⁶ ............................................. G01N 21/64
[52] U.S. Cl. ................................. 250/458.1; 356/318
[58] Field of Search .......................... 250/458.1, 459.1, 250/461.1; 356/317, 318, 417

[56] References Cited

U.S. PATENT DOCUMENTS 5,323,010  6/1994  Gratton et al. ....................... 250/458.1

FOREIGN PATENT DOCUMENTS 7-43404   2/1995  Japan .
7-63855   3/1995  Japan .
7-120327  5/1995  Japan .

OTHER PUBLICATIONS

Zhang et al, "Phase–Locked Detection of Fluorescence Lifetime", Rev. Sci. Instrum. vol. 64, No. 9, Sep. 1993, pp. 2531–2540.

Sugeta et al, "Metal–Semiconductor–Metal Photodetector for High–Speed Optoelectronic Circuits", Proceedings of the 11th Conference (1979 International) on Solid State Device, Tokyo, 1979, Japanese Journal of Applied Physics, vol. 19 (1980) Supplement 19-1, pp. 459–464.

Ito et al, "Low Dark Current GaAs Metal–Semiconductor––Metal (MSM) Photodiodes Using $WSi_x$ Contacts", IEEE Journal of Quantum Electronics, vol. QE-22, No. 7, Jul. 1986, pp. 1073–1077.

Primary Examiner—Davis L. Willis
Assistant Examiner—Kiet T. Nguyen
Attorney, Agent, or Firm—Cushman Darby & Cushman, L.L.P.

[57] ABSTRACT

An excitation light beam intensity-modulated and output from a light-sending unit is irradiated on a target measurement object. A scattered light beam or a reaction light beam is detected by a light-receiving unit through a wavelength selector. The light-receiving unit outputs a signal according to the product of a supplied modulation signal and the received light beam. A processing unit acquires data corresponding to the product value for each type of light, and calculates the decay characteristics of the reaction light beam on the basis of the acquisition result. In this manner, with a simple arrangement, the decay time of a fluorescence sample or the like is precisely measured in a wide frequency range.

23 Claims, 29 Drawing Sheets

MSM CHARACTERISTICS 1

MSM CHARACTERISTICS 2

MSM CHARACTERISTICS 3

MSM CHARACTERISTICS 4

VOLTAGE INPUT (V_M)

MODULATED INCIDENT LIGHT

TIME-AVERAGED OUTPUT (V_dc)

PHASE DIFFERENCE=0

PHASE DIFFERENCE=$\pi/2$

PHASE DIFFERENCE=$\pi$

SINE WAVE

TRIANGULAR WAVE

TRAPEZOIDAL WAVE

RECTANGULAR WAVE

PHASE DIFFERENCE OUTPUT

DECAY CHARACTERISTIC MEASURING APPARATUS

BACKGROUND OF THE INVENTION

1. Field of the Invention

The present invention relates to a decay characteristic measuring apparatus for measuring the decay time and the like of a light beam, e.g., fluorescence generated upon light irradiation on an object having decay characteristics.

2. Related Background Art

Various systems are conventionally proposed for measurement of the decay characteristics of fluorescence or the like. These systems can be roughly classified into (1) a system for measuring the waveform of a change of light intensity to obtain a decay waveform from the measured waveform (to be referred to as a direct method hereinafter) and (2) a system using intensity-modulated excitation light to obtain decay characteristics from a phase difference with respect to decay signal light (to be referred to as a phase difference method hereinafter).

The following arrangements are available as typical specific arrangements of apparatuses using the conventional direct method:

① Light Source+Photomultiplier (PMT)+Oscilloscope

This apparatus is used in a relatively slow region and rarely used in a high-speed region of 10 ns or less where a distortion of an electrical signal (e.g., ringing and overshoot) or a distortion of the detector itself (e.g., spread of transit time) poses a problem.

② Short Pulse Laser+High-Speed PMT+Constant Fraction Discriminator+TAC (Time to Amplitude Converter)+PHA (Pulse Height Analyzer)

A time resolving power of several tens ps can be obtained by a time-correlated single photon counting method.

③ Streak Camera (Real Time Measurement)

A time resolving power in units of subpico seconds can be obtained. A single phenomenon can also be observed. In a system for overlapping (multiplying) a phenomenon many times in a single photoelectron region to obtain a waveform, a sufficient dynamic range can be obtained, which enables highly precise measurement of decay characteristics. Wavelength information can simultaneously be acquired using a spectroscope. This apparatus is excellent as a time-resolved spectroscope.

④ Optical Oscilloscope (Sampling Measurement)

This is a sampling type optical waveform observing apparatus using a streak tube. It is not suitable for measurement of extremely low intensity light because of a poor collection efficiency of target measurement light in this method, though the dynamic range in the measurement light amount region is excellent.

⑤ Boxcar (Sampling Measurement)

An electrical gate system is applied, and an inexpensive system is available. The time resolving power ($\geq 100$ ps) is determined by the frequency response and electrical gate width of a detector.

⑥ Kerr cell (Optical Sampling Measurement)

An optical gate system is applied. The time resolving power depends on the laser pulse width for sampling, which can be shortened.

The phase difference method is suitable to obtain a decay time constant with a somewhat specified waveform at a high speed because of its high light utilization efficiency. A system or apparatus like an optical fiber thermometer usable in an environment with large disturbance noise such as a high electromagnetic field is proposed, in which a ruby or alexandrite crystal whose a fluorescence decay time largely changes in accordance with a temperature is used as a probe, and a phase difference between an excitation light beam and fluorescence is converted into a frequency by a PLL (Phase-Locked Loop), thereby measuring a lifetime (e.g., "Zhiyi Zhang et al., Rev. Sci. Instrum. 64 (9), pp. 2531–2540 (1993)", Japanese Patent Laid-Open No 63-308596, "T. Bosselmen et al., Proc. 2nd Optical Fiber Sensor Conf., 1984, Stuttgart, pp 151–154", "Zhiyi Zhang et al., Rev. Sci. Instrum. 62, p. 1735 (1991)"). If the waveform is not specified, or multicomponent decay characteristics are to be measured, the modulation frequency is changed (when the excitation light is modulated by sine wave modulation), or the target frequency (an integer multiple of a repetition period when the excitation light is an impulse) is changed. Data of phase difference and intensity are acquired every time the frequency is changed, and processing such as fitting is performed, thereby obtaining the decay characteristics (J. R. Lakowicz et al., SPIE vol. 1204 Time-Resolved Laser Spectroscopy in Biochemistry II, pp. 13–20 (1990)).

SUMMARY OF THE INVENTION

It is an object of the present invention to provide a decay characteristic measuring apparatus with a simple arrangement, which can precisely measure the decay time of a fluorescence sample or the like and is usable in a wide frequency range, and particularly, in a high-frequency range up to several GHz.

The first decay characteristic measuring apparatus according to the present invention comprises (a) a light-sending unit for irradiating a first light beam having a first wavelength on a target measurement object, the first light beam being intensity-modulated with a first electrical signal changed in accordance with a first frequency, and having an intensity periodically changed in accordance with the first frequency, (b) a wavelength selector for receiving a second light beam as a scattered light beam of the first light beam on the target measurement object, and a third light beam having a second wavelength, the third light beam being generated on the target measurement object upon irradiation of the first light beam output from the light-sending unit on the target measurement object, and selecting and outputting one of the second and third light beams in accordance with a designation from an outside, (c) a light-receiving unit, having a photodetector for receiving a second electrical signal controlling a photoelectric conversion gain and having a second frequency, receiving the light beam output from the wavelength selector, and generating a third electrical signal containing a component having a third frequency corresponding to an absolute value of a difference between the first frequency and the second frequency, the third electrical signal being an electrical signal corresponding to a received light intensity and the set photoelectric conversion gain, for outputting a fourth signal reflecting the component of the third frequency from the third electrical signal, and (d) a measurement processing unit for outputting the first electrical signal to the light-sending unit, outputting the second electrical signal to the light-receiving unit, outputting a wavelength selection designation signal for designating the selected wavelength to the variable wavelength selector, and obtaining decay characteristics of the third light beam from a first measurement result of the fourth signal output from the light-receiving unit upon selection of the first wavelength and a second measurement result of the fourth signal output from the light-receiving unit upon selection of the second wavelength, on the basis of a phase difference between a phase of a change in intensity of the second light beam supplied to the light-receiving unit and a phase of a change in intensity of the third light beam supplied to the light-receiving unit.

The second decay characteristic measuring apparatus according to the present invention comprises (a) a first light-sending unit for irradiating a first light beam having a first wavelength on a target measurement object, the first light beam being intensity-modulated with a first electrical signal changed in accordance with a first frequency, and having an intensity periodically changed in accordance with the first frequency, (b) a first wavelength selector for selecting and outputting a second light beam as a scattered light beam of the first light beam on the target measurement object, (c) a first light-receiving unit, having a first photodetector for receiving a second electrical signal controlling a photoelectric conversion gain and having a second frequency, receiving the second light beam, and generating a third electrical signal containing a component having a third frequency corresponding to an absolute value of a difference between the first frequency and the second frequency, the third electrical signal being an electrical signal corresponding to a received light intensity and the set photoelectric conversion gain, for outputting a fourth signal reflecting an amplitude value of the component of the third frequency from the third electrical signal, (d) a second light-sending unit for irradiating a third light beam having the first wavelength on the target measurement object, the third light beam being intensity-modulated with a fifth electrical signal changed in accordance with a fourth frequency, and having an intensity periodically changed in accordance with the fourth frequency, (e) a second wavelength selector for selecting and outputting a fourth light beam having a second wavelength, the fourth light beam being generated on the target measurement object upon irradiation of the third light beam output from the second light-sending unit on the target measurement object, (f) a second light-receiving unit, having a second photodetector for receiving a sixth electrical signal controlling the photoelectric conversion gain and having a fifth frequency, receiving the light beam transmitted through the second wavelength selector, and generating a seventh electrical signal containing a component having a sixth frequency corresponding to an absolute value of a difference between the fourth frequency and the fifth frequency, the seventh electrical signal being an electrical signal corresponding to the received light intensity and the set photoelectric conversion gain, for outputting an eighth signal reflecting an amplitude value of the component of the sixth frequency from the seventh electrical signal, and (g) a measurement processing unit for outputting the first electrical signal to the light-sending unit, outputting the second electrical signal to the light-receiving unit, outputting the fifth electrical signal to the second light-sending unit, outputting the sixth electrical signal to the second light-receiving unit, and obtaining decay characteristics of the fourth light beam from a first measurement result of the fourth signal output from the first light-receiving unit and a second measurement result of the eighth signal output from the second light-receiving unit, on the basis of a phase difference between a phase of a change in intensity of the second light beam supplied to the first light-receiving unit and a phase of a change in intensity of the fourth light beam supplied to the second light-receiving unit.

In both the apparatuses, the light-receiving unit may comprise ① a signal supplying unit for receiving an electrical signal, converting the electrical signal into a predetermined output form, and outputting the electrical signal, ② a photoconductive photodetector, having an electrical signal application terminal for receiving the electrical signal output from the signal supplying unit, for receiving a light beam, ③ a conversion amplification unit for outputting a voltage signal corresponding to the electrical signal flowing through the photoconductive photodetector, and ④ a frequency selector for receiving the voltage signal output from the conversion amplification unit, and selecting and passing a voltage signal having substantially the same frequency as that corresponding to an absolute value of a difference between a frequency of a change in intensity of the light beam incident on the photoconductive photodetector and a frequency of the electrical signal supplied to the signal supplying unit.

The predetermined output form is preferably ① a voltage signal output in a low output impedance state, or ② a current signal output in a high output impedance state. It is preferable to further provide bias regulating means for adjusting an operating point of the photoconductive photodetector.

The photoconductive photodetector may be characterized in that ① when a target measurement light intensity is constant, and an applied voltage value is an independent variable, a current amount flowing through the photoconductive photodetector exhibits a substantial odd function of the applied voltage within a predetermined domain including an applied voltage value of 0 V, ② when the applied voltage is constant, and the target measurement light intensity is an independent variable, the current amount flowing through the photoconductive photodetector exhibits a substantial linear function of an irradiation signal intensity within a predetermined domain of the target measurement light intensity, and ③ the voltage signal applied to the photoconductive photodetector is periodic and has a time average value of substantially zero, in which an amplitude exhibits a substantial even function of a time when a middle point between adjacent times where the amplitude becomes zero is defined as an origin. Alternatively, the photoconductive photodetector may be characterized in that ① when a target measurement light intensity is constant, and an applied current value is an independent variable, a voltage value generated across the photoconductive photodetector is represented by a substantial odd function of the applied current within a predetermined domain including an applied current value of 0 A, ② when the applied current is constant, and the target measurement light intensity is an independent variable, the voltage value generated across the photoconductive photodetector is represented by a substantial linear function of an irradiation signal intensity within a predetermined domain of the target measurement light intensity, and ③ the non-DC component of the current signal applied to the photoconductive photodetector is periodic and has a time average value of substantially zero, in which an amplitude is represented by a substantial even function of a time when a middle point between adjacent times where the amplitude of the non-DC component becomes zero is defined as an origin.

As such a photoconductive photodetector, ① a metal-semiconductor-metal photodetector having a structure wherein rectifier junctions are connected in opposite directions or ② a photodetector having a structure wherein ohmic contact electrodes are connected to oppose each other can be applied.

The first apparatus may be characterized in that the first frequency is equal to the second frequency, and the phase difference between the first electrical signal and the second electrical signal is known, and the measurement processing unit comprises ① a frequency adjustment unit for adjusting the first frequency to maintain a condition for fixing the output signal from the light-receiving unit to a reference value, ② a frequency measurement device for measuring the first frequency adjusted and fixed by the frequency adjustment unit, and ③ an arithmetic processing unit for calculating a first phase difference corresponding to a difference between the phase of the change in intensity of the second light beam at a position of the photodetector and a phase of a change in amplitude of the first electrical signal from a first measurement frequency measured by the frequency measurement device when the second light beam is selected by the wavelength selector, calculating a second phase difference corresponding to a difference between the phase of the change in intensity of the third light beam at the position of the photodetector and a phase of a change in amplitude of the first electrical signal from a second measurement frequency measured by the frequency measurement device when the third light beam is selected by the wavelength selector, and obtaining the decay characteristics of the third light beam on the basis of the first phase difference and the second phase difference.

The fourth signal is a voltage signal, the reference value is 0 V, and the difference between the phase of the change in intensity of the second light beam at the position of the photodetector and the phase of the change in amplitude of the second electrical signal when the first frequency fixed by the frequency adjustment unit is the first measurement frequency, and the difference between the phase of the change in intensity of the third light beam at the position of the photodetector and the phase of the change in amplitude of the second electrical signal when the first frequency fixed by the frequency adjustment unit is the second measurement frequency may be one of $\pi/2$ and $3\pi/2$.

The second apparatus may be characterized in that the first frequency is equal to the second frequency, the phase difference between the first electrical signal and the second electrical signal is known, the fourth frequency is equal to the fifth frequency, the phase difference between the fifth electrical signal and the sixth electrical signal is known, and the measurement processing unit comprises ① a first frequency adjustment unit for adjusting the first frequency to maintain a condition for fixing the output signal from the first light-receiving unit to a reference value, ② a first frequency measurement device for measuring the first frequency adjusted and fixed by the first frequency adjustment unit, ③ a second frequency adjustment unit for adjusting the fourth frequency to maintain a condition for fixing the output signal from the second light-receiving unit to a reference value, ④ a second frequency measurement device for measuring the fourth frequency adjusted and fixed by the second frequency adjustment unit, and ⑤ an arithmetic processing unit for calculating a first phase difference corresponding to a difference between the phase of the change in intensity of the second light beam at a position of the first photodetector and a phase of a change in amplitude of the first electrical signal from a first measurement frequency measured by the first frequency measurement device, calculating a second phase difference corresponding to a difference between the phase of the change in intensity of the fourth light beam at a position of the second photodetector and a phase of a change in amplitude of the fifth electrical signal from a second measurement frequency measured by the second frequency measurement device, and obtaining the decay characteristics of the fourth light beam on the basis of the first phase difference and the second phase difference.

The fourth electrical signal and the eighth electrical signal are voltage signals, the reference value is 0 V, and the difference between the phase of the change in intensity of the second light beam at the position of the first photoconductor and the phase of the change in amplitude of the second electrical signal when the first frequency fixed by the first frequency adjustment unit is the first measurement frequency, and the difference between the phase of the change in intensity of the fourth light beam at the position of the second photodetector and the phase of the change in amplitude of the sixth electrical signal when the fourth frequency fixed by the second frequency adjustment unit is the second measurement frequency may be one of $\pi/2$ and $3\pi/2$.

In the first apparatus, the first frequency may be different from the second frequency, and the measurement processing unit may calculate the decay characteristics of the third light beam on the basis of measurement values of an amplitude and phase of the fourth signal.

In the decay characteristic measuring apparatus of the present invention, the measurement processing unit designates the wavelength selector to select and output one light beam having the first wavelength (wavelength of excitation light) or the second wavelength (wavelength of reaction light such as fluorescence). For the descriptive convenience, assume that the light beam having the first wavelength is selected. The measurement processing unit sends the first electrical signal to the light-sending unit and the second electrical signal to the light-receiving unit before or after this selection.

Upon reception of the first electrical signal, the light-sending unit outputs a light beam having the first wavelength and an intensity corresponding to a change in amplitude of the first electrical signal, i.e., the first light beam having the first wavelength and intensity-modulated with the first electrical signal to the target measurement object as an excitation light beam. The excitation light beam output from the light-sending unit is irradiated on the target measurement object. The third light beam as a reaction light beam such as fluorescence having the second wavelength is generated by an interaction between the irradiated excitation light beam and the material of the target measurement object is generated and output from the target measurement object. Part of the excitation light beam is scattered on the target measurement object. The second light beam as the scattered light beam on the target measurement object and the third light beam are supplied to the wavelength selector.

On the other hand, upon reception of the second electrical signal, the light-receiving unit applies an electrical signal reflecting a change in second electrical signal to the photodetector. As the photodetector, an element whose photoconductive conversion efficiency changes in accordance with the value of the applied electrical signal is used. In this state, the photodetector receives the light beam having the first wavelength selected by the wavelength selector. Since the electrical signal reflecting the change in second electrical signal is applied to the photodetector, the photodetector actually calculates the product of the intensity of the light beam having the first wavelength and the amplitude of the second electrical signal. Therefore, a change in third electrical signal generated in the photodetector contains components of the sum and difference between the first frequency and the second frequency. The light-receiving unit converts the third electrical signal (e.g., an current signal) generated in the photodetector into an electrical signal reflecting a change with time in third electrical signal (e.g., a voltage signal), and thereafter, selects and outputs the fourth electrical signal containing only the component of the difference between the first frequency and the second frequency. More specifically, in the decay characteristic measuring apparatus according to the present invention, processing of a signal having a high frequency is performed by the photodetector. The signal is converted into a signal in an frequency region electrically easily to be handled, and thereafter, electrically amplified, thereby performing measurement.

The fourth signal output from the light-receiving unit is collected/measured by the measurement processing unit. As described above, the fourth signal contains only the component of the difference between the first frequency and the second frequency and also carries the intensity change information of the received second light beam. Therefore, when a signal having a frequency lower than the frequency of the change in intensity of the second light beam and electrically easily to be handled is electrically processed, e.g., amplified, the intensity change information of the second light beam is obtained. The measurement processing unit receives the fourth signal and records the characteristic value thereof.

If the first frequency is equal to the second frequency, the fourth signal contains only the DC component, and the value of the DC component reflects the phase difference between the second light beam and the second electrical signal. In this case, the measurement processing unit obtains the phase difference between the second light beam and the second electrical signal from the value of the fourth signal or the first frequency value and records the phase difference.

The measurement processing unit designates the wavelength selector to select and output a light beam having the second wavelength. The measurement processing unit sends the first electrical signal to the light-sending unit and the second electrical signal to the light-receiving unit before or after this selection. As in the above description, the characteristic value of the fourth signal associated with the third light beam (i.e., reaction light beam) is recorded by the measurement processing unit.

In accordance with the obtained difference between the characteristic value associated with the scattered light beam and that associated with the reaction light beam, the measurement processing unit calculates the decay characteristics such as the fluorescence lifetime of the reaction light beam.

In the decay characteristic measuring apparatus of the present invention, a photoconductive photodetector is preferably used as a photodetector, and the second electrical signal is supplied to the signal supplying terminal of the photoconductive photodetector as a modulation electrical signal. As a form of such a modulation electrical signal, a voltage signal output in a low output impedance state, or a current signal output in a high output impedance state can be used. When the photoconductive photodetector is applied, an electrical signal is selected in which the non-DC component of the electrical signal supplied to the photoconductive photodetector is periodic, the time average value is substantially zero, and the amplitude exhibits a substantial even function of a time when the middle point between adjacent times where the amplitude becomes zero is defined as an origin. At the same time, the bias value of the applied electrical signal is adjusted. In this case, the DC component of background light is removed, and AC component of background light other than the frequency of the modulation voltage signal is also reduced, thereby performing measurement.

In the second apparatus of the present invention, measurement of the characteristic value associated with the scattered light beam and measurement of the characteristic value associated with the reaction light beam are simultaneously performed. As a result, even when the distance from the light-sending unit or the light-receiving unit to the target measurement object tends to change, the decay characteristics can be precisely measured.

The decay time resolving power according to the conventional phase difference method is limited to 1/1000 the modulation period because of the fluctuation in intensity of the received light beam in reading the phase difference between the excitation light beam and the fluorescence. On the other hand, according to the present invention, the phase difference information is converted into a frequency and read, phase difference detection is directly performed by the photoconductive photodetector, and the phase difference between the voltage applied to the photodetector and the intensity-modulated light beam incident on the photodetector is fixed to, e.g. $\pi/2$ to $3\pi/2$ by a phase-locked loop (PLL) system. Therefore, a system not so influenced by abrupt variations in intensity of incident light can be formed, and the phase resolving power is not limited to 1/1000 the period.

In a normal system for performing phase comparison between electrical signals, an amplifier having a band up to the modulation frequency is required. However, a system for directly performing phase comparison between incident light and an electrical signal, as in the present invention, only requires an amplifier having a low frequency band, which is used as a loop filter in a PLL. Therefore, a simple circuit arrangement can be obtained. In addition, according to a system for converting the phase difference information into a frequency and reading the information, the resolving power is limited by the precision of the frequency counter. For this reason, measurement at a high resolving power can be performed.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Figure 1:
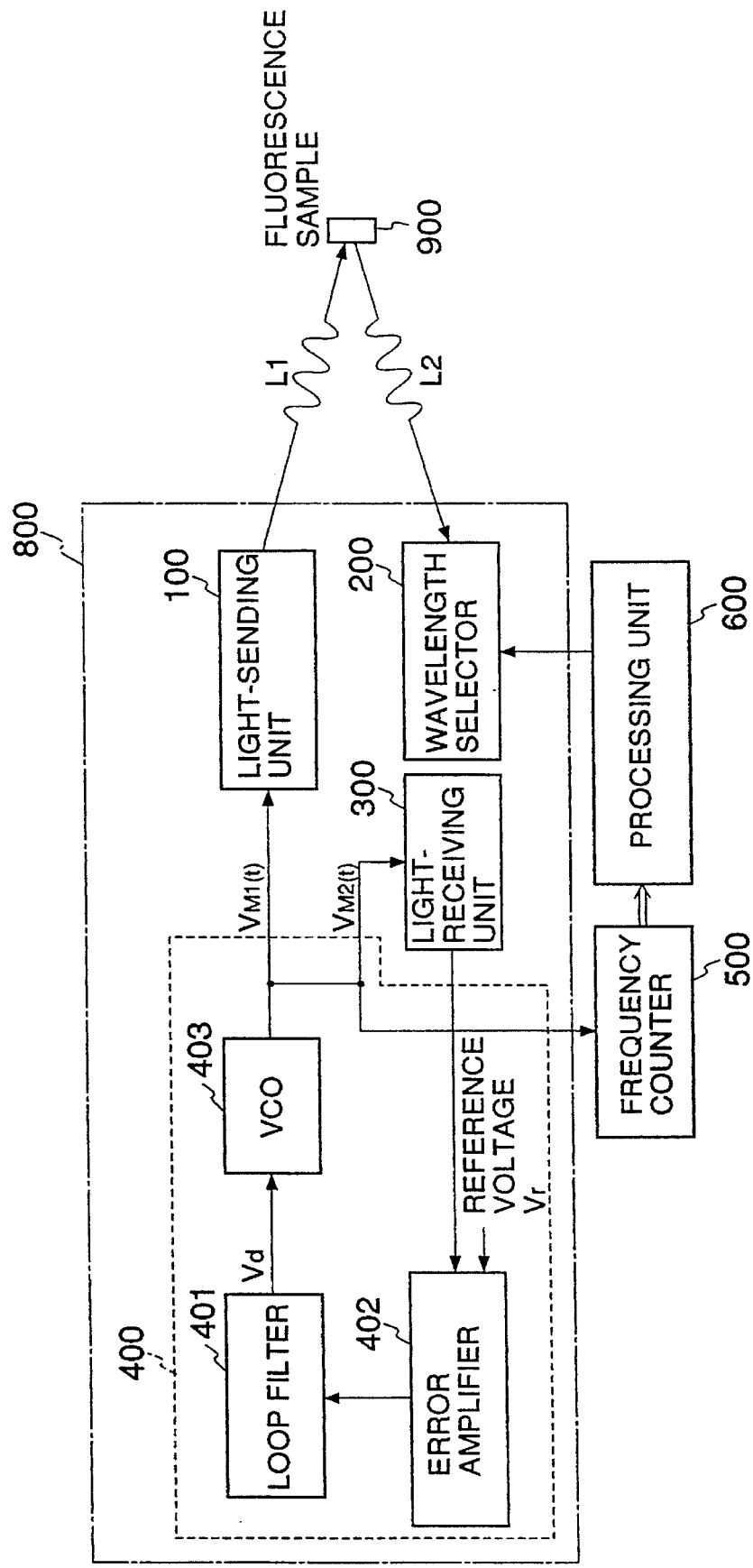
FIG. 1 is a block diagram schematically showing the arrangement of a decay characteristic measuring apparatus according to the first embodiment of the present invention.

A decay characteristic measuring apparatus according to an embodiment of the present invention will be described below with reference to the accompanying drawings. The same reference numerals denote the same elements throughout the drawings, and a repetitive description will be omitted.

(First Embodiment)

In this embodiment, the intensity modulation frequency of an excitation light beam is equal to the frequency of a control signal for the photoelectric conversion efficiency of a photodetector. The principle of this embodiment will be described prior to a detailed description of this embodiment.

FIG. 1 is a block diagram schematically showing the arrangement of a decay characteristic measuring apparatus of this embodiment. As shown in FIG. 1, this apparatus comprises (a) a light-sending unit 100, (b) a wavelength selector 200, (c) a light-receiving unit 300, (d) a frequency adjustment unit 400, (e) a frequency counter 500, and (f) a processing unit 600. The light-sending unit 100 receives a modulation signal $V_M(t)$ from the outside and outputs an excitation light beam $I_{EX}(t)$ having a wavelength=$\lambda_1$, which is intensity-modulated with the modulation signal $V_M(t)$, to a target measurement object 900. The wavelength selector 200 receives a reaction light beam $I_{RC}(t+\Phi_1+\Phi_2)$ having a wavelength=$\lambda_2$, which is generated on the target measurement object 900 when the excitation light beam $I_{EX}(t)$ output from the light-sending unit 100 is irradiated on the target measurement object 900, and a scattered light beam $I_{RF}(t+\Phi_1)$ obtained upon scattering of the excitation light beam $I_{EX}(t)$ on the target measurement object 900, and selects and outputs one of the light beams in accordance with a designation from the processing unit 600. The light-receiving unit 300 receives the modulation signal $V_M(t)$ and the light beam output from the wavelength selector 200, generates a current signal corresponding to the product of the intensity of the received light beam ($I_{RC}(t+\Phi_1+\Phi_2)$ or $I_{RF}(t+\Phi_1)$) and the modulation signal $V_M(t)$, and thereafter, outputs a voltage signal containing only an almost DC component. The frequency adjustment unit 400 outputs a modulation signal having a frequency corresponding to the voltage value of the almost DC voltage signal output from the light-receiving unit 300. The frequency counter 500 measures the frequency of the modulation signal output from the frequency adjustment unit 400. The processing unit 600 outputs a wavelength selection designation signal for designating the selected wavelength ($\lambda_1$ or $\lambda_2$) to the wavelength selector 200. At the same time, the processing unit 600 reads a frequency value f1 from the frequency counter 500 when the voltage value of the DC voltage signal output from the light-receiving unit 300 becomes almost "0 V" upon selection of the wavelength=$\lambda_1$. A phase difference $\Phi_1$ between the modulation signal $V_M(t)$ and the scattered light beam $I_{RF}(t+\Phi_1)$ is obtained from the read frequency value f1. The processing unit 600 reads a frequency value f2 from the frequency counter 500 when the voltage value of the DC voltage signal output from the light-receiving unit 300 becomes almost "0 V" upon selection of the wavelength=$\lambda_2$. A phase difference ($\Phi_1+\Phi_2$) between the modulation signal $V_M(t)$ and the reaction light beam $I_{RC}(t+\Phi_1+\Phi_2)$ is obtained from the read frequency value f2. The processing unit 600 obtains the decay characteristics of the reaction light beam in accordance with the two phase differences, i.e., $\Phi_2$.

The frequency adjustment unit 400 comprises ① an error amplifier 402, ② a loop filter 401, and ③ a voltage-controlled oscillator 403. The error amplifier 402 receives the DC voltage output signal from the light-receiving unit 300, amplifies the difference with respect to a reference voltage Vr, and outputs a signal. The loop filter 401 receives the output signal from the error amplifier 402 and passes only the almost DC component. The voltage-controlled oscillator 403 outputs a modulation signal having a frequency corresponding to the voltage value of the DC voltage signal output from the loop filter 401.

The light-sending unit 100, the wavelength selector 200, the light-receiving unit 300, and the frequency adjustment unit 400 constitute a lock system 800 for forming a phase-locked loop.

The principle of decay characteristic measurement by this apparatus will be described below.

The error amplifier 402 receives the DC voltage signal through the input terminal, outputs a voltage ($V_1 = G \cdot (V_d - Vr)$) having a value corresponding to the amplified difference between a DC voltage value ($V_d$) and the reference voltage value (Vr), and supplies the control voltage to the voltage-controlled oscillator (VCO) 403 through the loop filter 401. The voltage-controlled oscillator 403 oscillates a frequency corresponding to the supplied control voltage value. A voltage signal $V_{M1}(t)$ output from the voltage-controlled oscillator 403 is supplied to the light-sending unit 100. The light-sending unit 100 has a light source such as a laser diode (LD). The light-sending unit 100 modulates the intensity of an output light beam from the light source in accordance with the voltage signal output from the voltage-controlled oscillator 403 and outputs the light beam to the target measurement object 900 as the excitation light beam $I_{EX}(t)$. The scattered and reaction light beams on the target measurement object 900 are received by the light-receiving unit 300 through the wavelength selector 200. The wavelength selector 200 is constituted by a wavelength selecting element such as a spectroscope, an interference filter, and a dichroic mirror. The wavelength selector 200 separates the scattered component and fluorescence of the excitation light beam from each other, selects one of these components, and passes it. The modulation signal output from the voltage-controlled oscillator 403 is simultaneously received by the light-receiving unit 300. The light-receiving unit 300 calculates the phase difference between the received light beam and the modulation signal, converts the phase difference signal into the time-averaged voltage value, and outputs the voltage value. This time-averaged voltage value is supplied to the input terminal of the error amplifier 402. The frequency counter 500 detects the frequency of the modulation signal output from the voltage-controlled oscillator 403. Note that the frequency counter 500 can be replaced with any other device for measuring a frequency. For example, a combination of a frequency/voltage converter (F/V converter) and a voltmeter, a combination of a rate meter for outputting a voltage proportional to the repetition period of a pulse and a voltmeter, or a frequency discriminator used for an FM detector can also be used.

Figure 2:
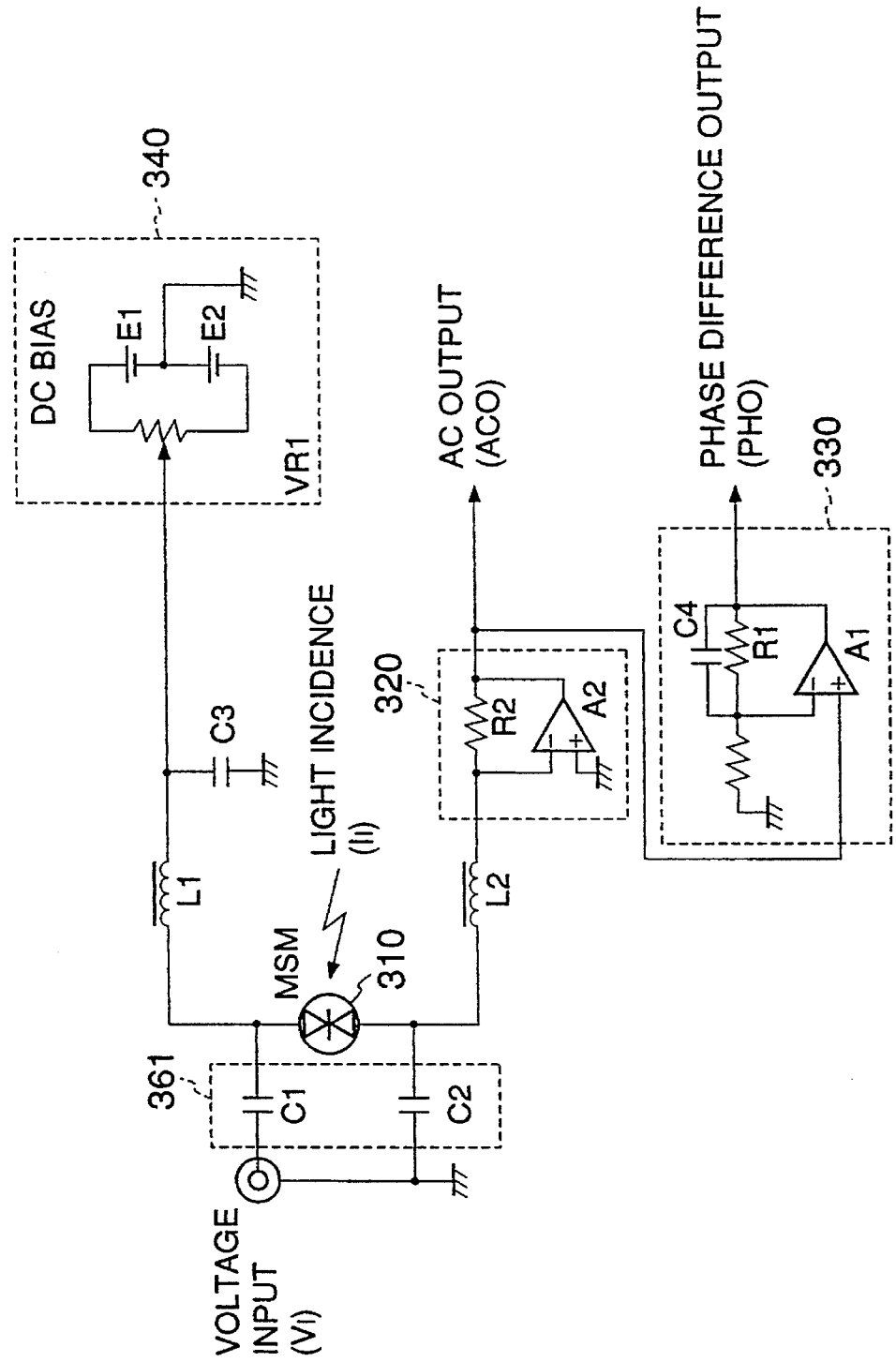
FIG. 2 is a block diagram showing the arrangement of a light-receiving unit of the first embodiment.

The light-receiving unit 300 directly multiplies the received optical waveform by the received electrical signal waveform, and outputs the low frequency component of the multiplication result as a voltage value. FIG. 2 is a block diagram showing arrangement 1 of the light-receiving unit for realizing this function. The light-receiving unit 300 is constituted by ① a photoconductive photodetector 310, ② a voltage application unit 361, ③ choke coils L1 and L2, ④ a current-to-voltage converter 320, ⑤ a low-pass filter 330, and ⑥ a bias regulator 340. The photoconductive photodetector 310 receives an optical signal ($I_t$) and a voltage signal ($V_t$) and calculates the product of the optical signal and the voltage signal, thereby outputting a current signal reflecting the phase difference between the received light beam and the modulation signal. The voltage application unit 361 is constituted by connecting capacitors C1 and C2 for applying a voltage signal corresponding to the AC component of the voltage signal to the photoconductive photodetector 310. The choke coils L1 and L2 pass the DC component of the current generated in the photoconductive photodetector 310. The current-to-voltage converter 320 converts the AC component of the current signal flowing through the choke coil L1, the photoconductive photodetector 310, and the choke coil L2 into a voltage. The low-pass filter 330 calculates the time average of the voltage signal output from the current-to-voltage converter 320 and outputs the calculation result. The bias regulator 340 adjusts the bias value of the voltage to be applied to the photoconductive photodetector 310.

Figure 3:
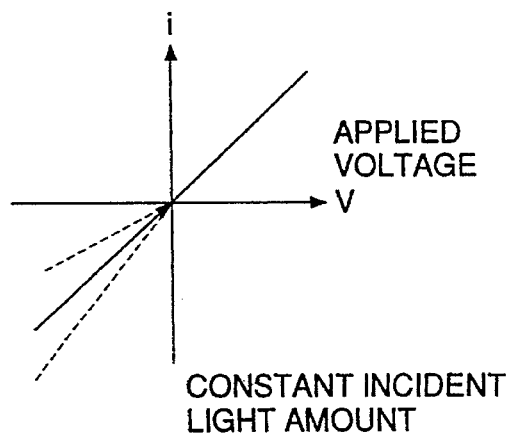
FIGS. 3 to 6 are graphs showing the characteristics of photoconductive photodetector usable in the first embodiment.
Figure 4:
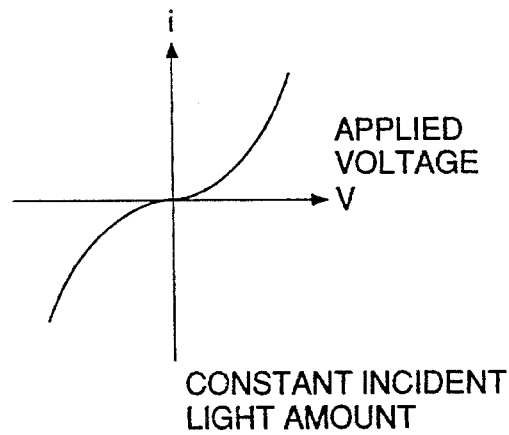
Figure 5:
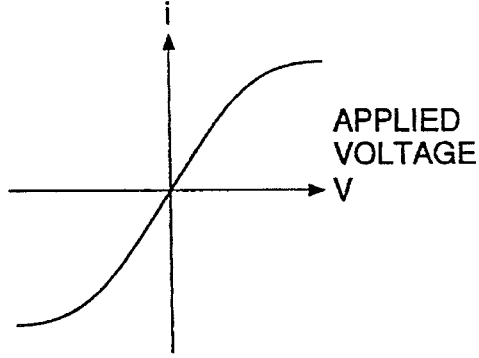
Figure 6:
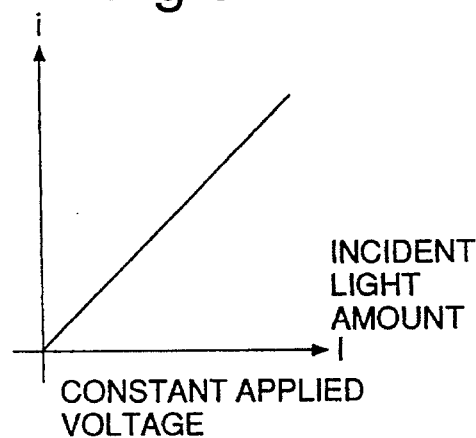

The photoconductive photodetector 310 is constituted by a metal-semiconductor-metal (MSM) photodetector using GaAs as a semiconductor material. This photoconductive photodetector 310 has characteristics representing that, when the irradiation light amount is constant, and the applied voltage value is an independent variable, the current amount flowing through the photoconductive photodetector exhibits an odd function of the applied voltage in a predetermined domain including an applied voltage value of 0 V, and characteristics representing that, when the applied voltage is constant, and the incident light amount is an independent variable, the current amount flowing through the photoconductive photodetector exhibits an almost linear function of the incident light amount. FIGS. 3 to 6 are graphs showing the characteristics of the photoconductive photodetector 310 usable in the phase difference detector of this embodiment. Generally, a photoconductive detector exhibits linear output current characteristics with respect to an applied voltage when the incident light amount is constant, as shown in FIG. 3. With respect to a positive/negative applied voltage, the current has a value equal to an absolute value corresponding to the voltage and can be regarded as a linear pure resistance. When the applied voltage is constant, the output current characteristics with respect to incident light can be represented by a straight line as shown in FIG. 6. An MSM as a high-speed photoconductive detector sometimes exhibits a non-linear current characteristics with respect to an applied voltage, as shown in FIG. 4 or 5. In this case as well, the detector can be applied as the photoconductive photodetector of this embodiment as far as current characteristics represent a value equal to the absolute value with respect to a positive/negative applied voltage. Assume that the characteristics represent different absolute values with respect to a positive/negative applied voltage, as indicated by broken lines in FIG. 3. In this case, as far as the absolute value ratio of a positive current to a negative current is kept constant within the range of a voltage applied to the MSM, this detector can also be applied in this embodiment by adding a DC offset voltage to the AC voltage applied to the MSM.

The photoconductive photodetector 310 can also be constituted by using single-crystal silicon, InP, amorphous silicon, or the like. A CdS cell or an MCT (HgCdTe) detector having a sensitivity in an infrared region with a wavelength of 2 to 17 μm can also be used, through they are not suitable for a high-speed operation. The MSM detector has a very simple arrangement wherein comb-shaped electrodes are formed on a wafer. Because of its small stray capacitance, the frequency response characteristics with respect to the size of a light-receiving surface are more excellent than those of a pin photodiode as a generally used typical high-speed detector. For this reason, a photodetector having a high sensitivity and excellent frequency characteristics can be easily formed. In addition, since the dark current can be minimized due to the arrangement, a high S/N ratio can be obtained.

An avalanche photodiode (APD) is also available as a photodetector. In this case, the dependency of the APD amplification characteristics on the voltage can be used to perform gain modulation, thereby constituting a light-receiving unit having phase difference detection characteristics. However, since this photodetector cannot be used while being applied with symmetrical positive/negative voltages, the phase difference output contains a DC offset voltage depending on the incident light amount, resulting in complex handling. In addition, the output with respect to background light cannot be eliminated. For this reason, in a measurement environment with strong background light, an incident light amount adjustment mechanism using a variable ND filter must be designed in consideration of saturation in the detector and the first-stage amplifier, resulting in a complex system.

On the other hand, with the above-described photoconductive photodetector such as an MSM to which symmetrical positive/negative voltages can be applied, saturation of the first-stage amplifier need not be taken into consideration even when strong background light is incident, so that a system can be easily formed.

The current-to-voltage converter 320 is constituted by an operational amplifier A2 and a resistor R2. A received AC current signal is converted into a voltage by the resistor R2, and a voltage signal is output.

The low-pass filter 330 is constituted by an operational amplifier A1, a capacitor C4, and a resistor R1. The low-pass filter 330 integrates a received voltage signal with a time constant determined by the product of the capacitance value of the capacitor C4 and the resistance value of the resistor R1 to calculate a time-averaged value, thereby outputting an almost DC voltage corresponding to the phase difference.

The bias regulator 340 is constituted by a variable resistor VR1 for adjusting the bias voltage value and DC power supplies E1 and E2 connected to the terminals of the variable resistor VR1 and connected to each other in series. The connecting point between the DC power supplies E1 and E2 is set to a ground potential.

The bias voltage of the light-receiving unit 300 is regulated by the variable resistor VR1 such that the output becomes "0 V" when unmodulated light is received. In this case, when the fluctuation of air is neglected, an AC component $I_{RV}(t)$ of a received light beam (DC component=$I_0$) as an input signal to the light-receiving unit 300, and a modulation signal $V_{M2}(t)$ are represented by following equations:

$$I_{RV}(t) = I_{RV0} \sin(\omega t - \Phi) \quad (1)$$

where $I_{RV0}$: intensity amplitude (modulation component) of scattered modulated light
$\omega$: modulation frequency
$\Phi$: phase difference between received light and modulation signal $$V_M(t) = V_{M0} \sin(\omega t) \quad (2)$$

where $V_{M0}$: voltage amplitude of modulation signal.
A current $i_{DT}(t)$ flowing through the photoconductive photodetector 310 is represented as follows:

$$\begin{aligned} i_{DT}(t) &= I_{RV}(t) \cdot V_M(t) \\ &= K_1 \cdot \sin(\omega t - \Phi) \cdot \sin(\omega t) \\ &= K_2 \cdot (\cos(2\omega t - \Phi) + \cos\Phi) \end{aligned} \quad (3)$$

where $K_i$: constant (i=1, 2)
The current-to-voltage converter 320 converts the current signal $i_{DT}(t)$ into a voltage signal $V_{AC}(t)$ represented by the following equation and outputs the voltage signal $V_{AC}(t)$:

$$\begin{aligned} V_{AC}(t) &= K_3 \cdot i_{DT}(t) \\ &= K_4 \cdot (\cos(2\omega t - \Phi) + \cos\Phi) \end{aligned} \quad (4)$$

The time-averaged value of the voltage signal $V_{AC}(t)$ is obtained by the low-pass filter 330, and a voltage value represented by the following equation is output from the low-pass filter 330:

$$\begin{aligned} V_{DC}(t) &= V_{DC} \\ &= K_5 \cdot \cos\Phi \end{aligned} \quad (5)$$

Figure 7A:
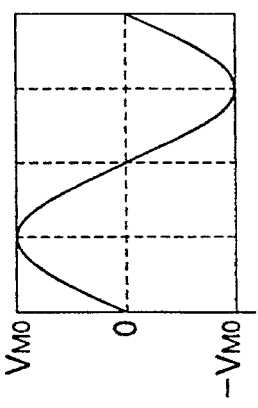
FIGS. 7 to 9 are graphs for explaining the operation of the light-receiving unit of the first embodiment.
Figure 8A:
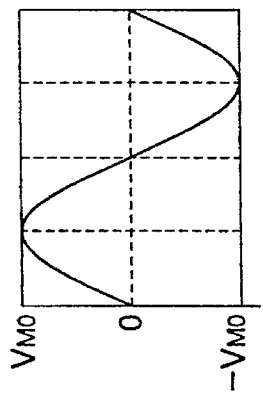
Figure 9A:
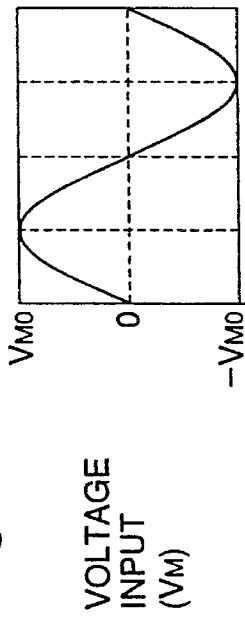
Figure 7B:
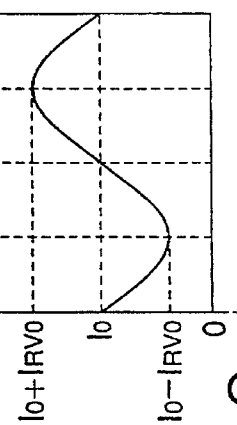
Figure 8B:
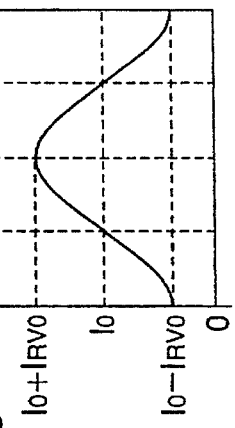
Figure 9B:
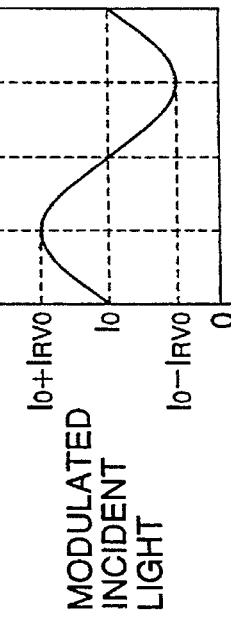
Figure 7C:
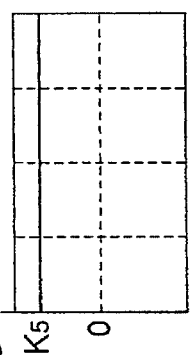
Figure 8C:
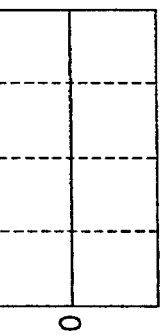
Figure 9C:
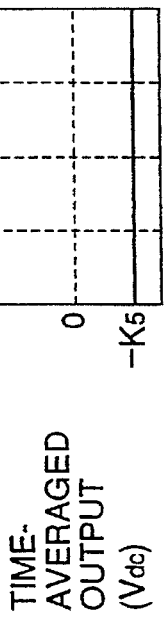

FIGS. 7 to 9 are graphs each showing the relationship between the phase difference ($\Phi$) in equation (1) and the output voltage ($V_{DC}$) so as to explain the operation of the light-receiving unit. FIG. 7 shows a case wherein the phase difference is zero (+2n$\pi$; n=integer), FIG. 8 shows a case wherein the phase difference is $\pi/2$ (+n$\pi$; n=integer), and FIG. 9 shows a case wherein the phase difference is $\pi$ (+2n$\pi$; n=integer).

Therefore, when the input value to the reference voltage terminal of the error amplifier 402 is "0 V", an output voltage value $V_f$ from the error amplifier 402 is represented as follows:

$$V_f = G \cdot V_{DC} = G \cdot K_5 \cdot \cos\Phi \quad (6)$$

where G: gain of error amplifier
That is, $$\cos\Phi = V_f/(G \cdot K_5) \quad (7)$$

If the error amplifier 402 has a sufficient gain (i.e., if the value G is sufficiently large), a phase-locked loop (PLL) for always maintaining the phase difference between the scattered modulated light and the modulation signal to almost $\pi/2$ (+n$\pi$; n=integer) is formed.

Even when the lock condition of the phase-locked loop is satisfied, the modulation frequency value is not uniquely determined. If the oscillation frequency range of the voltage-controlled oscillator 403 is set to include a period 4/3 a delay time (L/c) of the two-way distance in advance, and the initial modulation frequency is sufficiently low, the phase difference is exactly set to $\pi/2$ at a predetermined frequency value of the voltage-controlled oscillator 403.

When the transmission wavelength is set to the wavelength $\lambda_1$ of the scattered excitation light beam by the wavelength selector, the oscillation frequency $f_1$ for satisfying the above lock condition is given by the following equation:

$$1/f_1 = (4/3)(T_d + (L/c)) \quad (8)$$

where Td is the sum of the group delay time in the light-sending unit and the group delay time in the light-receiving unit.

When the transmission wavelength is set to the wavelength $\lambda_2$ of the reaction light beam by the wavelength selector, the oscillation frequency $f_2$ for satisfying the above lock condition is given by the following equation:

$$1/f_2 = (4/3)(T_d + (L/c) + (1/f_2)(\Phi_2/2\pi)) \quad (9)$$

where $\Phi_2$ is a phase delay with respect to the scattered excitation light beam. In accordance with equations (8) and (9), $\Phi_2$ is obtained as follows:

$$\Phi_2 = 2\pi(3/4)(1 - (f_2/f_1)) \quad (17)$$

If the decay characteristics can be approximated by a simply logarithmic function, it is known that a phase delay $\Phi_D$ of a decay signal light beam with respect to the excitation light beam is given by the following equation:

$$\Phi_D = \tan^{-1}\omega\tau \quad (10)$$

where $\omega$: angular frequency $\tau$: decay constant (lifetime) (F. W. J. Teale: Time-Resolved Spectroscopy in Biochemistry and Biology, NATO ASI Series, Life Sciences, vol. 69, pp. 59–80). Therefore, the lifetime $\tau$ representing the decay characteristics of a decay light beam can be obtained as follows:

$$\tau = \tan \Phi_2/(2\pi f_2) \quad (11)$$

Figure 10:
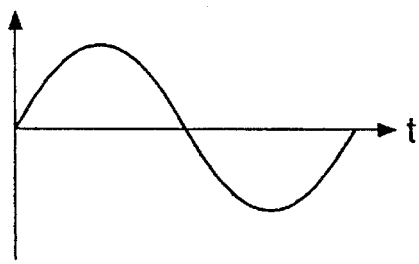
FIGS. 10 to 13 are charts for explaining modulation signals supplied to the photoconductive photodetector of the first embodiment.
Figure 11:
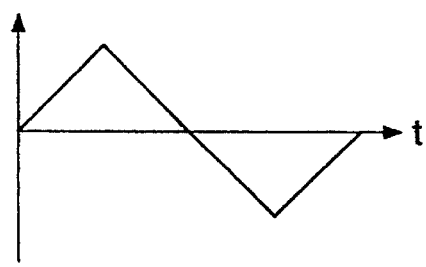
Figure 12:
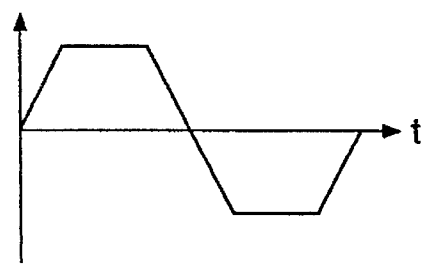
Figure 13:
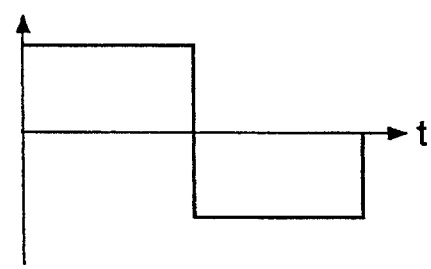

FIGS. 10 to 13 are graphs for explaining modulation signals. In the above description, a sine wave shown in FIG. 10 is used as a modulation signal. In the time-amplitude coordinate system, the waveform of the modulation signal exhibits ① a periodic function having a predetermined period, ② a time-averaged amplitude value of "0" and ③ an output value of "0 V" from the light-receiving unit 300 when the phase difference becomes ¼ the period, as in the above example, assuming that a time at a middle point between adjacent times where the amplitude becomes zero is defined as the origin, and the amplitude represents an even function of time. More specifically, a triangular wave in FIG. 11, a trapezoidal wave in FIG. 12, or a rectangular wave in FIG. 13 is usable.

Figure 14:
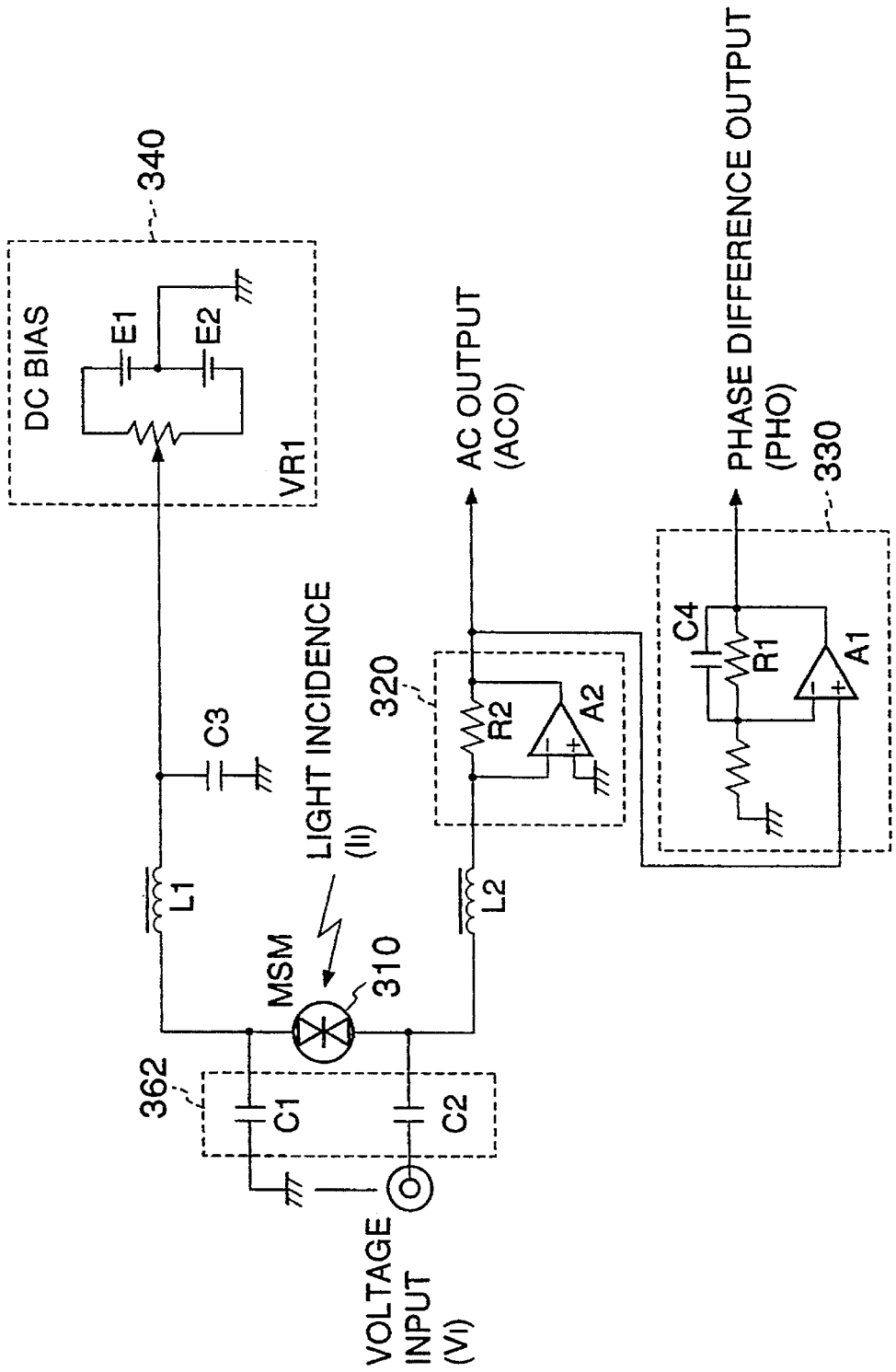
FIG. 14 is a block diagram showing the arrangement of a modification of the light-receiving unit.
Figure 15:
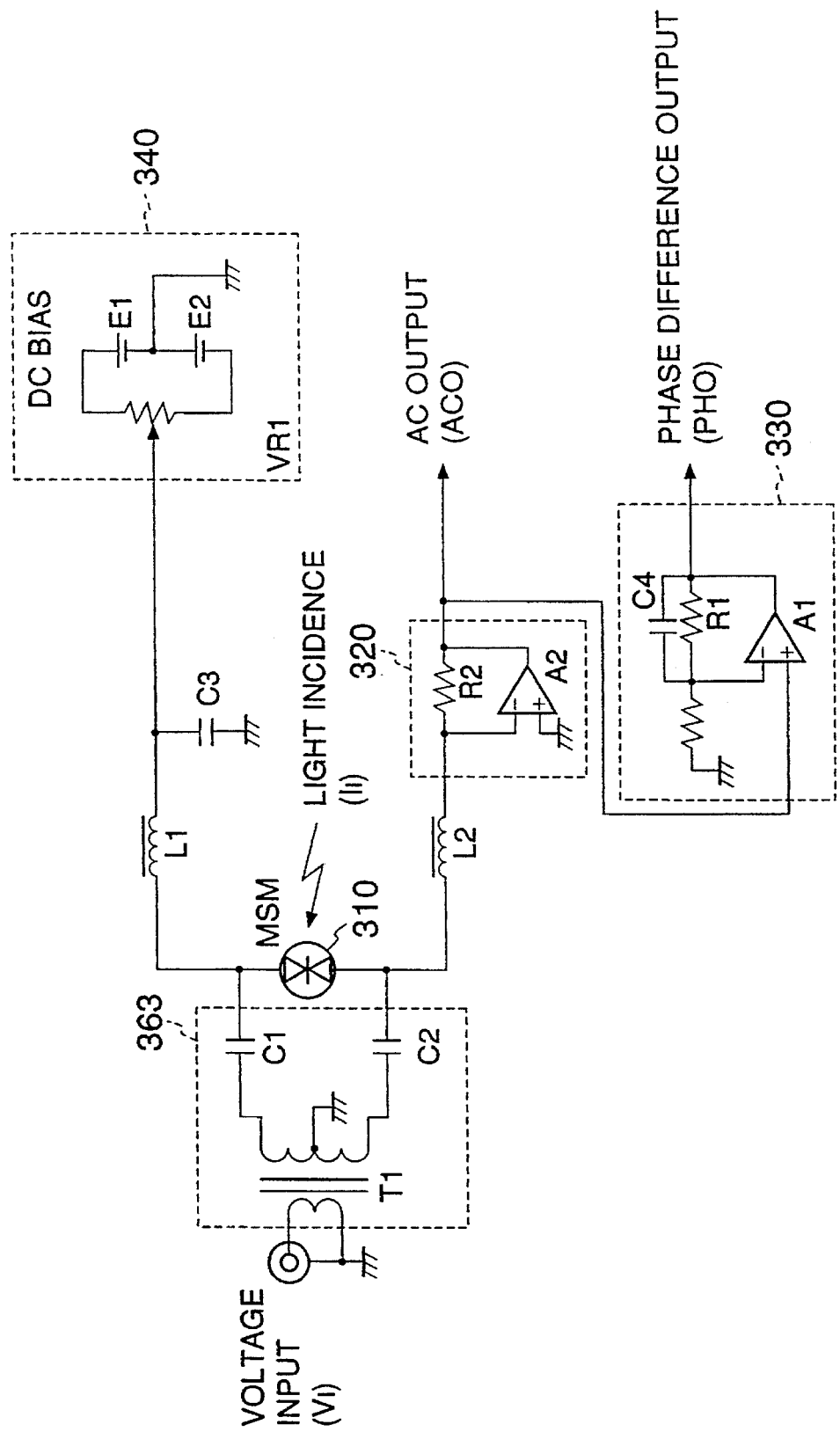
FIG. 15 is a block diagram showing the arrangement of another modification of the light-receiving unit.
Figure 16:
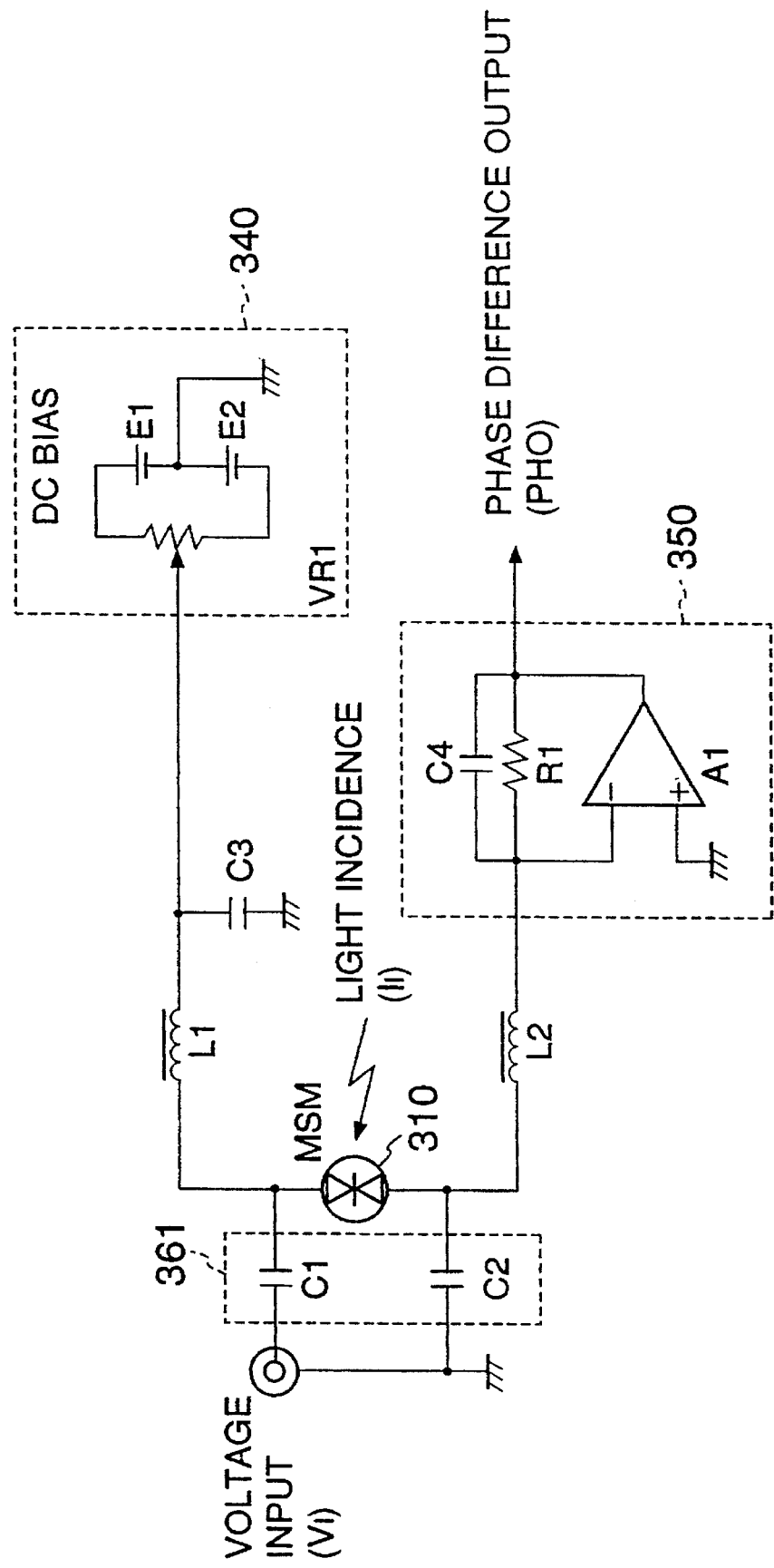
FIG. 16 is a block diagram showing the arrangement of still another modification of the light-receiving unit.
Figure 17:
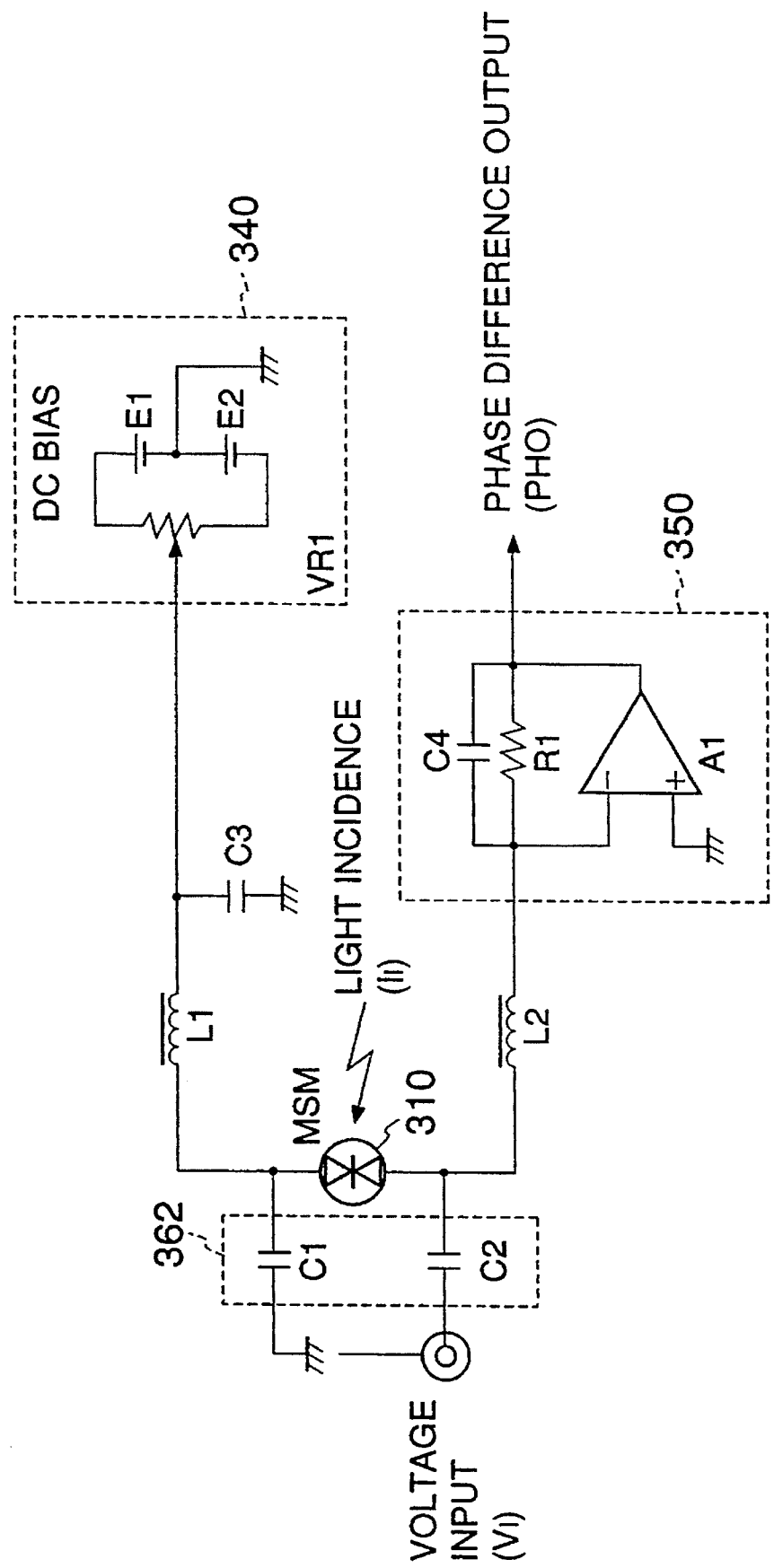
FIG. 17 is a block diagram showing the arrangement of still another modification of the light-receiving unit.
Figure 18:
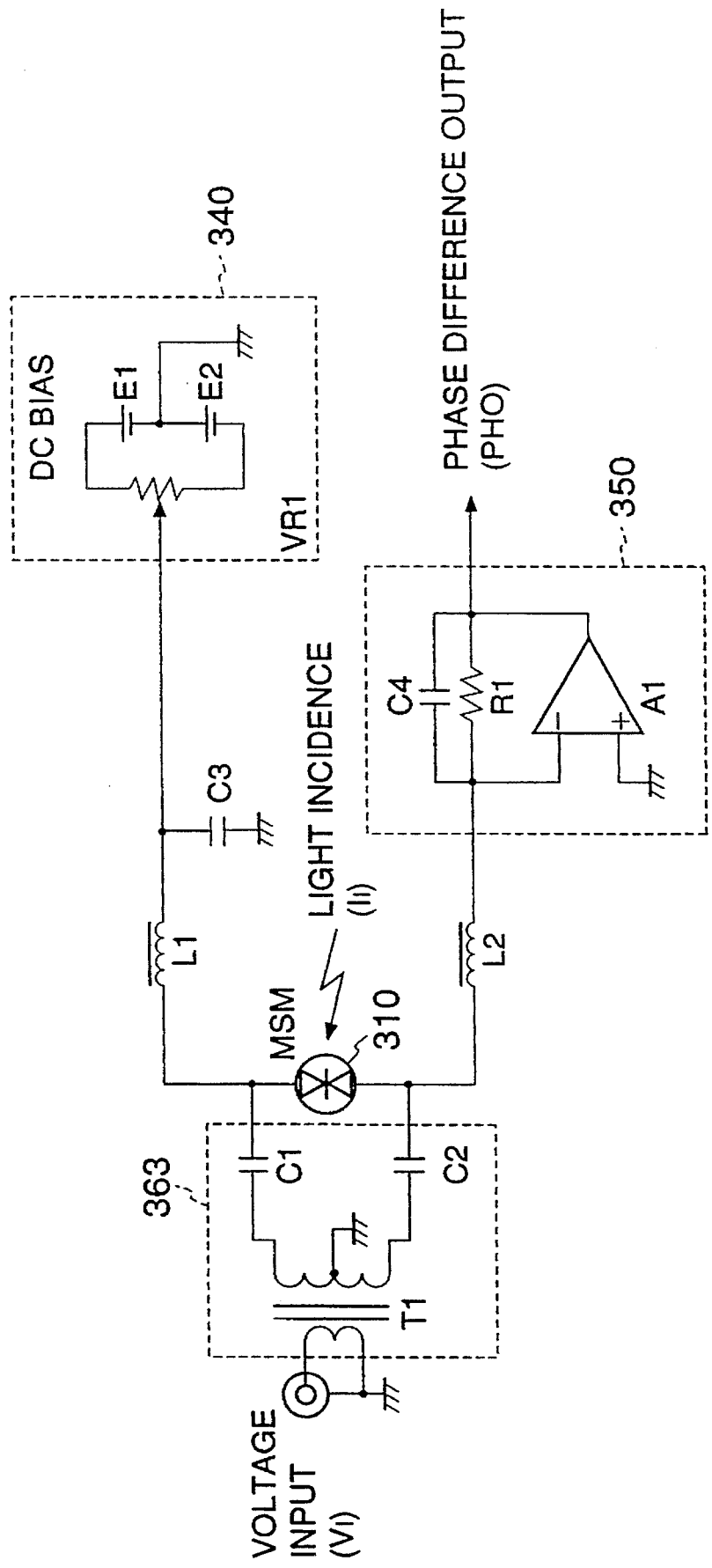
FIG. 18 is a block diagram showing the arrangement of still another modification of the light-receiving unit.

For the light-receiving unit 300 with the arrangement in FIG. 2, the phase-locked loop can also be similarly formed even when the modulation signal applying method is changed, i.e., a voltage application unit 362 as shown in FIG. 14 is applied, or a voltage application unit 363 as shown in FIG. 15 is applied. If only a DC voltage is necessary as an output, a current-to-voltage converter 350 constituted by integrating the current-to-voltage converter 320 and the low-pass filter 330 can also be used, as shown in FIG. 16. In correspondence with a modification of the light-receiving unit 300 from the arrangement in FIG. 2 to that in FIG. 14 or 15, the arrangement of the light-receiving unit in FIG. 16 can be modified into that in FIG. 17 or 18.

Figure 19:
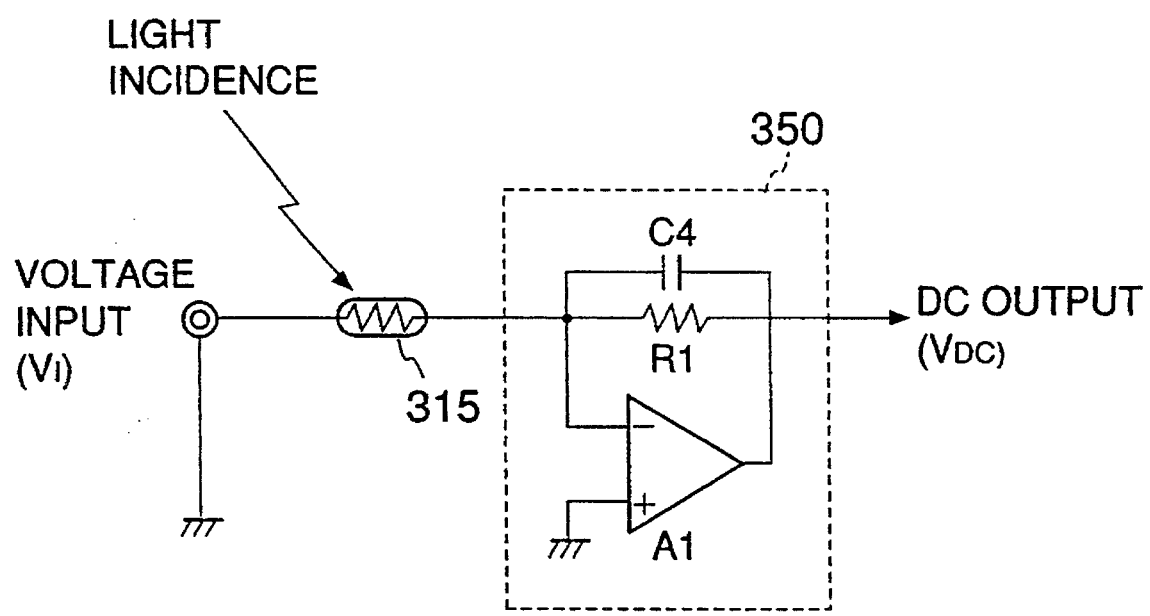
FIG. 19 is a block diagram showing the arrangement of still another modification of the light-receiving unit.

The above circuit arrangement is preferable for the photoconductive photodetector 310 consisting of, e.g., an MSM using GaAs with a satisfactory transient response. However, when a photoconductive photodetector 315 using CdS or PbS as a light-receiving material with an insufficient transient response is used, a circuit arrangement as shown in FIG. 19 is preferable. In this case, the arrangement can be realized without any voltage application unit.

Some photoconductive photodetector exhibit a small dark resistance, so they are not suitable for use in voltage application performed in the first embodiment (for example, an MCT (HgCdTe) photodetector having a sensitivity in an infrared region with a wavelength of 2 to 17 μm exhibits a dark resistance of 40 Ω). When such a photoconductive photodetector is applied, the following system is more preferable from the viewpoint of stability or S/N ratio. That is, instead of modulating the gain of the photodetector by voltage application, a current is supplied from a current supply equivalently having a very large output impedance, and this supplied current is modulated to detect a voltage generated across the photodetector.

Figure 20:
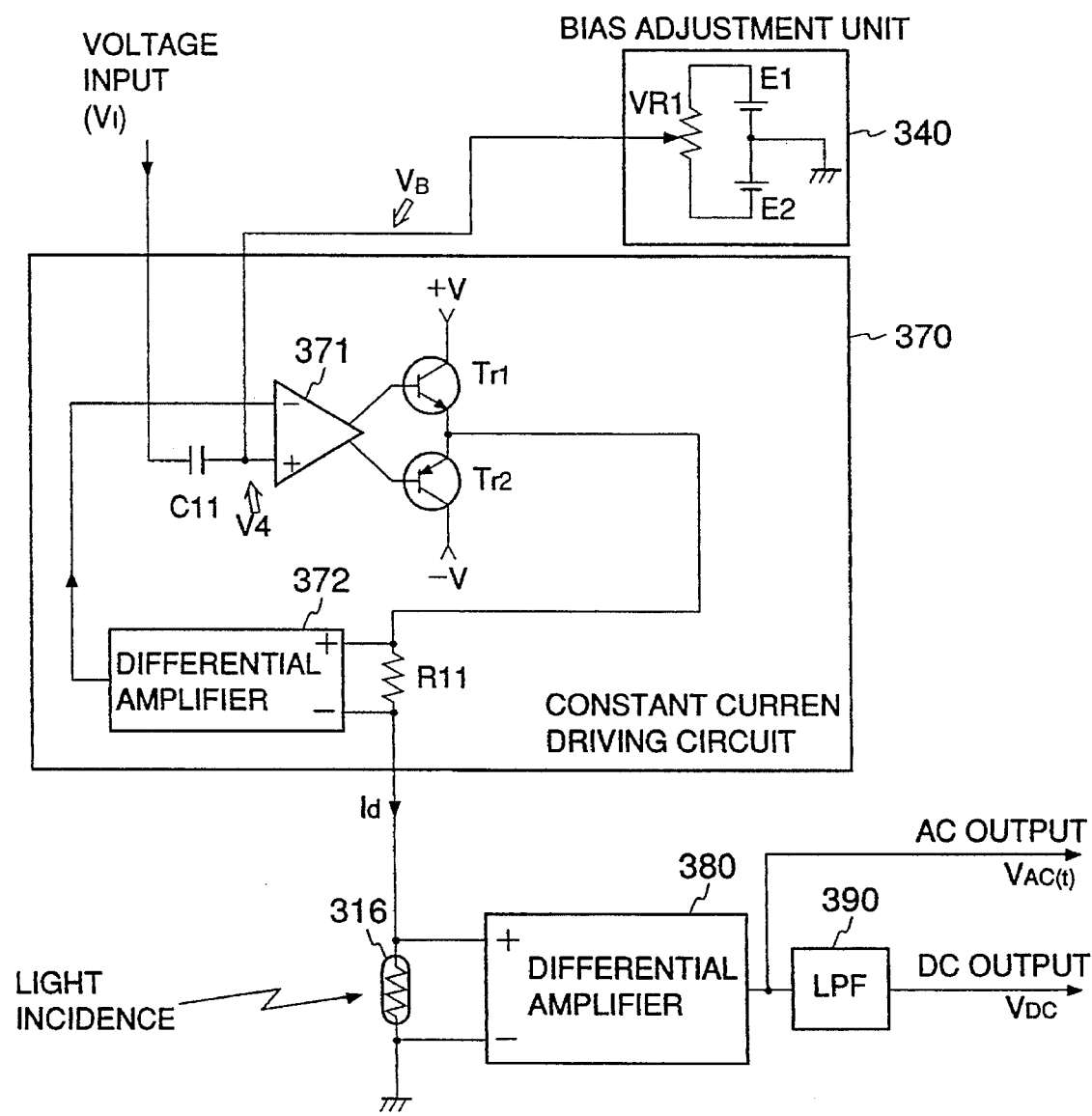
FIG. 20 is a block diagram showing the arrangement of still another modification of the light-receiving unit.

FIG. 20 is a block diagram showing the arrangement of a preferable light-receiving unit to which the above photoconductive photodetector is applied. As shown in FIG. 20, this light-receiving unit comprises ① a constant current driving circuit 370, ② a photoconductive photodetector 316, ③ the bias regulation unit 340, ④ a differential amplifier 350, and ⑤ a low-pass filter 390. The constant current driving circuit 370 receives the modulation signal and supplies a current signal in a high impedance state in accordance with the AC component value of the modulation signal. The photoconductive photodetector 316 has current supply terminals for inputting/outputting the current supplied from the constant current driving circuit 370 and receives the target measurement light beam. The bias regulation unit 340 sets the average driving current value of the constant current driving circuit 370. The differential amplifier 380 amplifies a voltage signal generated by a current generated in the photoconductive photodetector 316 upon reception of the light beam. The low-pass filter 390 passes an almost DC component contained in the voltage signal output from the differential amplifier 380. The constant current driving circuit 370 has ① a capacitor C11, ② an operational amplifier 371, ③ a transistor Tr1 and a transistor Tr2, ④ a resistor R11, and ⑤ a differential amplifier 372. The capacitor C11 receives the modulation signal through one terminal while receiving a bias voltage ($V_B$) output from the bias regulation unit 340 through the other terminal, and outputs an AC voltage signal ($V_4(t) = V_B + V_3(t)$) which is DC-biased by the bias voltage value from the other terminal. The operational amplifier 371 receives the voltage signal $V_4(t)$ through the positive input terminal, amplifies the difference with respect to the voltage received through the negative input terminal (gain=G1), and outputs the voltage signal (two outputs). The transistor Tr1 receives the positive output from the operational amplifier 371 through the base terminal and has a collector terminal connected to a positive power supply (+V). The transistor Tr2 receives the negative output from the operational amplifier 371 through the base terminal and has a collector terminal connected to a negative power supply (−V) and an emitter terminal connected to the emitter terminal of the transistor Tr1. The resistor R11 has one terminal connected to the emitter terminal of the transistor Tr1 (and the emitter terminal of the transistor Tr2) and the other terminal connected to one of the current input/output terminals of the photoconductive photodetector 316. The differential amplifier 372 has a positive input terminal connected to one of the terminals of the resistor R11, a negative input terminal connected to the other terminal of the resistor R11, and an output terminal connected to the negative input terminal of an operational amplifier 371.

The light-receiving unit shown in FIG. 20 operates as follows.

A voltage (=r11·Id) generated across the resistor R11 by a current Id flowing through the resistor R11 is amplified by the differential amplifier 372 and supplied to the negative input terminal of the operational amplifier 371. The operational amplifier 371 controls the transistors Tr1 and Tr2 such that the voltage value at the negative input terminal of the operational amplifier 371 matches the voltage value $V_4(t)$ supplied to the positive input terminal. As a result, the current value Id flowing through the photoconductive photodetector 316 is given by the following equation:

$$Id = V_4(t)/(G1 \cdot r11) \qquad (12)$$
$$= (V_B/(G1 \cdot r11)) + (V_3(t)/(G1 \cdot r11))$$

More specifically, the current value Id is not influenced by the resistance value of the photoconductive photodetector 316, and its change amount is proportional to the AC component $V_3(t)$ of the voltage signal generated by the modulation voltage signal.

In this state, when an optical signal is supplied to the photoconductive photodetector 316, a voltage signal corresponding to the product value of the modulation voltage $V_3(t)$ and the AC component of the incident light beam is generated between the current input/output terminals of the photoconductive photodetector 316. This voltage signal contains a DC component and an AC component. The voltage signal containing the two components is amplified by the differential amplifier 380. Thereafter, the DC component is selected by the low-pass filter 390 and output.

Figure 21:
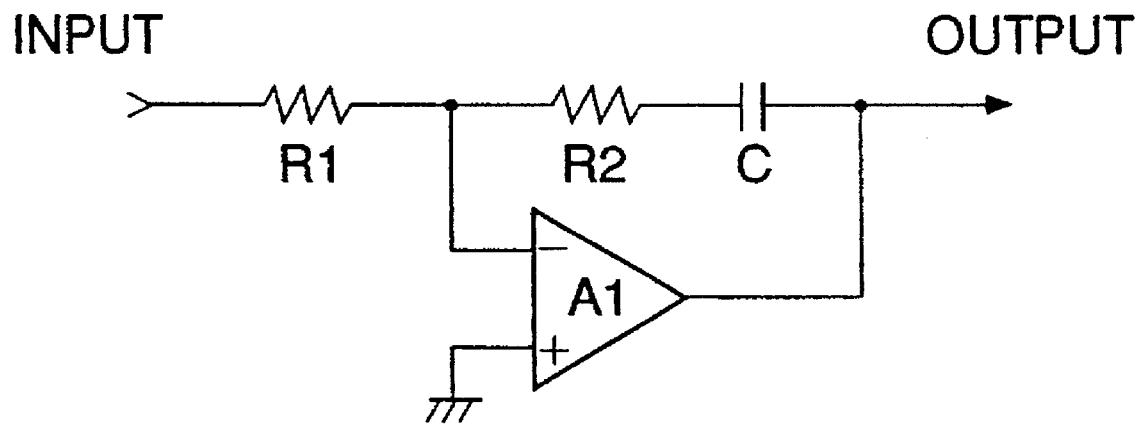
FIG. 21 is a circuit diagram showing the arrangement of a loop filter.

FIG. 21 is a circuit diagram showing the arrangement of the loop filter 401. As shown in FIG. 21, to eliminate the steady-state error in phase, an integration type arrangement is applied to ensure an almost infinite gain in the low frequency band, and reduce the noise band to stabilize the oscillation frequency.

Figure 22:
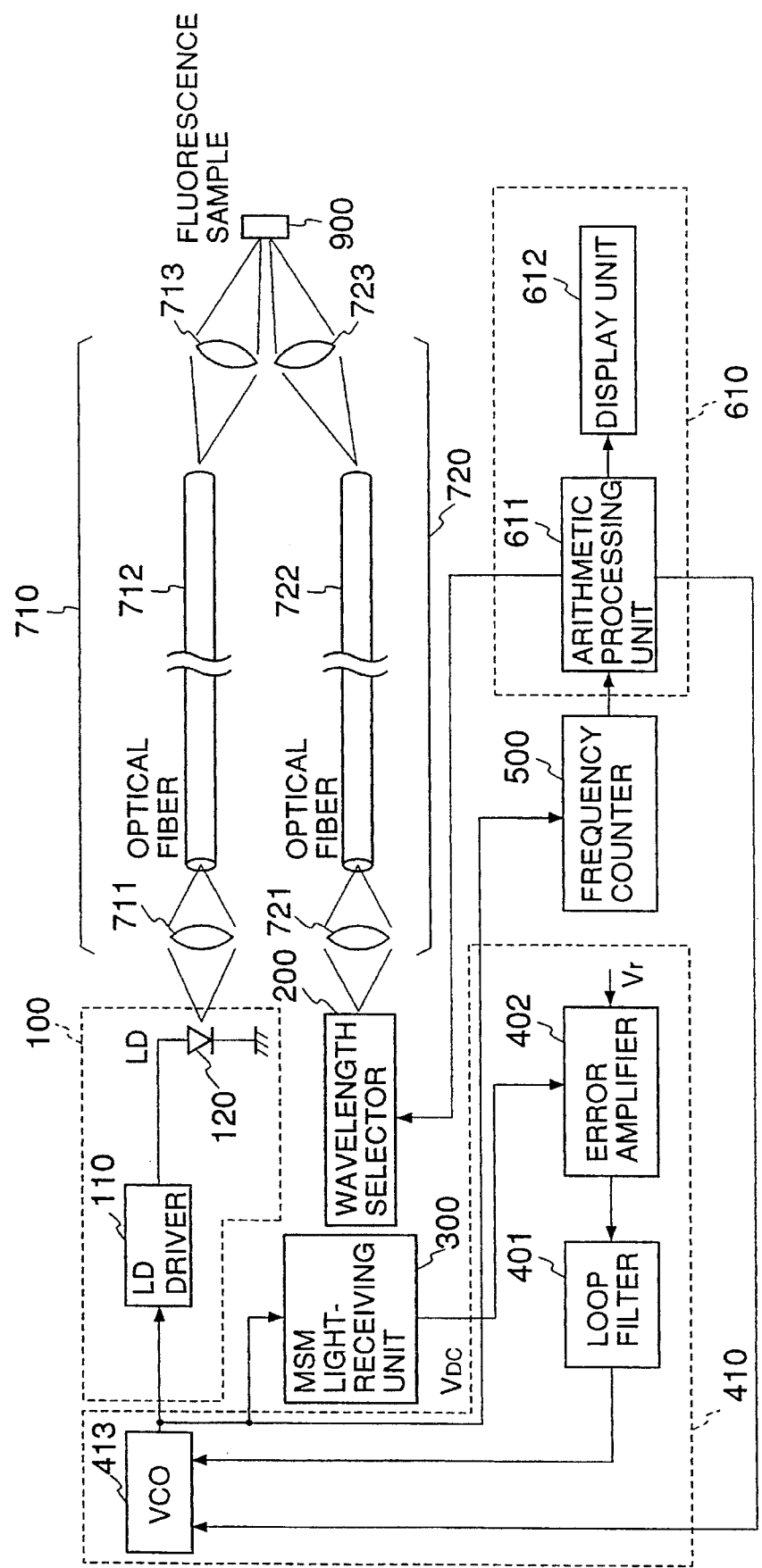
FIG. 22 is a block diagram showing the arrangement of the decay characteristic measuring apparatus of the first embodiment.

FIG. 22 is a block diagram showing the arrangement of the decay characteristic measuring apparatus of this embodiment in detail. Note that a fluorescence sample is used as the target measurement object 900 in this embodiment. As shown in FIG. 22, this apparatus comprises (a) the light-sending unit 100, (b) an optical system 710, (c) an optical system 720, (d) the wavelength selector 200, (e) the light-receiving unit 300, (f) a frequency adjustment unit 410, (g) the frequency counter 500, and (h) a processing unit 610. The light-sending unit 100 receives the modulation signal $V_M(t)$ from the frequency adjustment unit 410, and outputs the excitation light beam $I_{EX}(t)$ having the wavelength=$\lambda_1$, which is intensity-modulated with the modulation signal $V_M(t)$, to the target measurement object 900. The optical system 710 guides the light beam output from the light-sending unit 100 to the target measurement object 900. The optical system 720 guides the reaction light beam $I_{RC}(t+\Phi_1+\Phi_2)$ having the wavelength=$\lambda_2$, which is generated on the target measurement object 900 upon irradiation of the excitation light beam $I_{EX}(t)$ output from the light-sending unit 100 on the target measurement object 900, and the scattered light beam $I_{RF}(t+\Phi_1)$ obtained upon scattering of the excitation light beam $I_{EX}(t)$ on the target measurement object 900. The wavelength selector 200 receives the reaction and scattered light beams, and selects and outputs one of the light beams in accordance with a designation from the processing unit 610. The light-receiving unit 300 receives the modulation signal $V_M(t)$ and the light beam output from the wavelength selector 200, generates a current signal corresponding to the product of the intensity of the received light beam ($I_{RC}(t+\Phi_1+\Phi_2)$ or $I_{RF}(t+\Phi_1)$) and the modulation signal $V_M(t)$, and thereafter, outputs a voltage signal containing only an almost DC component. The frequency adjustment unit 410 outputs a modulation signal having a frequency corresponding to the voltage value of the almost DC voltage signal output from the light-receiving unit 300. The frequency counter 500 measures the frequency of the modulation signal output from the frequency adjustment unit 400. The processing unit 610 outputs a wavelength selection designation signal for designating the selected wavelength ($\lambda_1$ or $\lambda_2$) to the wavelength selector 200. At the same time, the processing unit 610 reads the frequency value f1 from the frequency counter 500 when the voltage value of the DC voltage signal output from the light-receiving unit 300 becomes almost "0 V" upon selection of the wavelength=$\lambda_1$. The phase difference $\Phi_1$ between the modulation signal $V_M(t)$ and the scattered light beam $I_{RF}(t+\Phi_1)$ is obtained from the read frequency value f1. The processing unit 610 also reads the frequency value f2 from the frequency counter 500 when the voltage value of the DC voltage signal output from the light-receiving unit 300 becomes almost "0 V" upon selection of the wavelength=$\lambda_2$. The phase difference ($\Phi_1+\Phi_2$) between the modulation signal $V_M(t)$ and the reaction light beam $I_{RC}(t+\Phi_1+\Phi_2)$ is obtained from the read frequency value f2. The processing unit 610 obtains the decay characteristics of the reaction light beam in accordance with the two phase differences, i.e., $\Phi_2$.

The light-sending unit 100 is constituted by ① a laser diode (LD) 120 and ② an LD driver 110. The LD 120 emits an excitation light beam (wavelength=$\lambda_1$) having an intensity according to the flowing current. The LD driver 110 receives a modulation signal $V_{M1}(t)$ from the frequency adjustment unit 410 and supplies a current according to the value of the modulation signal $V_{M1}(t)$ to the LD 120.

The processing unit 610 has ① an arithmetic processing unit 611 and ② a display unit 612. The arithmetic processing unit 611 issues a wavelength selection designation signal to the wavelength selector 200, reads the frequency value measured by the frequency counter 500, and calculates the decay characteristics of the reaction light beam. The display unit 612 displays the calculation result from the arithmetic processing unit 611 in accordance with a designation from the arithmetic processing unit 611.

The frequency adjustment unit 410 uses a voltage-controlled oscillator 413 capable of designating the oscillation frequency band in accordance with a designation from the arithmetic processing unit 611, in place of the voltage-controlled oscillator 403 of the frequency adjustment unit 400.

The optical system 710 is constituted by ① a lens 711 for focusing the excitation light beam output from the LD 120, ② an optical fiber 712 for receiving and guiding the excitation light beam focused by the lens 711 and ③ a lens 713 for focusing the light beam output from the optical fiber 712 onto the target measurement object 900.

The optical system 720 is constituted by ① a lens 723 for focusing the scattered light beam and the reaction light beam from the target measurement object 900, ② an optical fiber 722 for receiving and guiding the excitation light beam focused by the lens 723, and ③ a lens 721 for focusing the light beam output from the optical fiber 722 onto the wavelength selector 200.

The apparatus shown in FIG. 22 measures the decay characteristics of the reaction light beam in the following manner.

The arithmetic processing unit 611 designates the wavelength selector 200 to select and output the light beam having the wavelength $\lambda_1$ as the wavelength of an excitation light beam. In this state, the light-receiving unit 300 is operated, and the bias voltage value output from the bias regulator 340 is adjusted such that the DC output voltage value from the light-receiving unit 300 becomes "0 V".

The voltage-controlled oscillator 413 is designated to select the oscillation frequency band. Upon reception of a band selection designation, the voltage-controlled oscillator 413 oscillates an angular frequency (ω) within the designated band and outputs an oscillation signal to the light-sending unit 100 and the light-receiving unit 300. The light-sending unit 100 receives the oscillation signal through the LD driver 110. The LD driver 110 applies an appropriate DC bias to the oscillation signal and drives the LD 120. The driven LD 120 emits an excitation light beam which is intensity-modulated with the modulation angular frequency ω.

The laser beam emitted from the LD 120 is irradiated on the target measurement object 900 through the optical system 710 as an excitation light beam. On the target measurement object 900 irradiated with the excitation light beam, part of the excitation light beam is scattered while fluorescence is generated. The scattered component of the excitation light beam and part of the fluorescence are guided to the wavelength selector 200 through the optical system 720. The wavelength selector 200 separates the scattered component (to be referred to as a scattered light beam hereinafter) of the excitation light beam from the fluorescence in accordance with the wavelength selection designation from the processing unit 610, and outputs the scattered light beam to the light-receiving unit 300.

The scattered light beam supplied to the light-receiving unit 300 is received by the photoconductive photodetector 310. An output signal from the voltage-controlled oscillator 413 is applied between the voltage application terminals of the photoconductive photodetector 310. Therefore, the current signal represented by equation (3) is generated in the photoconductive photodetector 310. The current signal generated in the photoconductive photodetector 310 sequentially passes through the current-to-voltage converter 320 and the low-pass filter 330, and the DC voltage signal $V_{DC}$ represented by equation (5) is output. The error voltage signal $V_{DC}$ output from the light-receiving unit 300 is guided by the loop filter 401 and limited to a necessary band. Thereafter, the voltage signal is amplified by the DC amplifier 402 and supplied to the voltage-controlled oscillator 413 as a control voltage. The voltage-controlled oscillator 413 determines the oscillation frequency in accordance with the control voltage value. More specifically, when a frequency lower than the locked frequency (f1) is oscillated, the oscillation frequency is controlled to become higher. To the contrary, when a frequency higher than the locked frequency (f1) is oscillated, the oscillation frequency is controlled to become lower. Since the gain G of the error amplifier 402 is set to be sufficiently high, the phase difference ($\Phi_1$) between the phase of the scattered light beam ($I_{SC}(\omega t+\Phi_1)$) incident on the photoconductive photodetector 310 and that of a modulation voltage ($V_{M2}(t)$) applied to the photoconductive photodetector 310 is obtained as almost π/2 (+nπ; n=integer) in accordance with equation (7).

The locked frequency f1 for satisfying the lock condition is generally represented as follows:

$$1/f1 = (4/(4n-1)) \cdot (Td+L/c) \quad (13)$$

Figure 24:
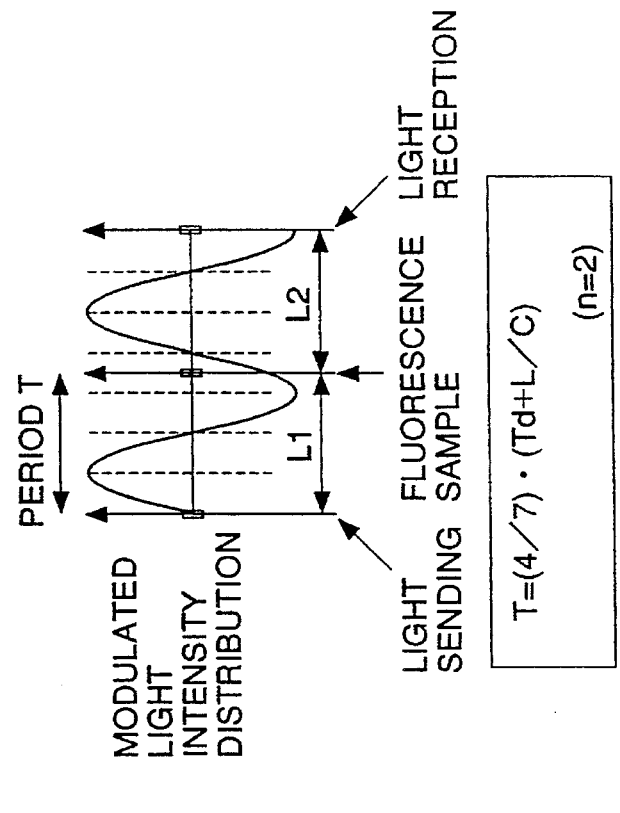
FIGS. 23 and 24 are views for explaining the lock condition of the decay characteristic measuring apparatus of the first embodiment.
Figure 23:
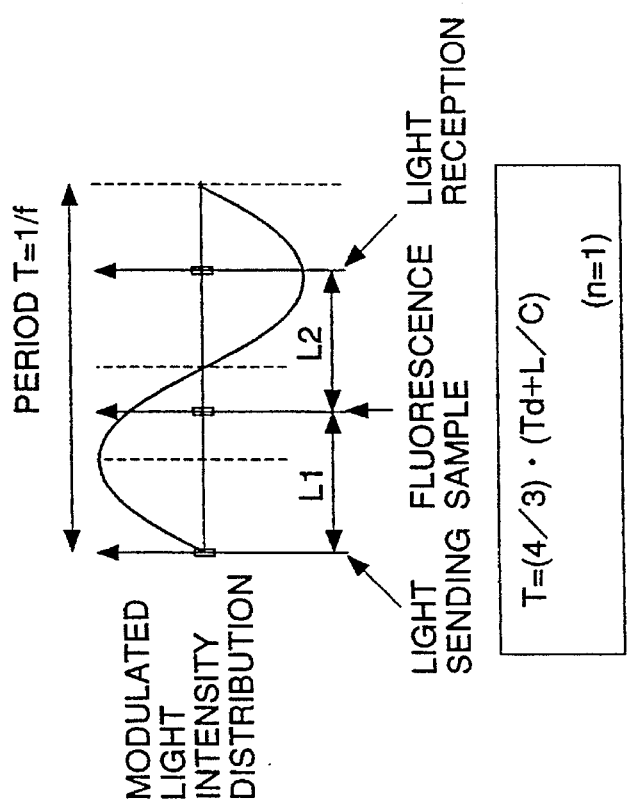

FIGS. 23 and 24 are views each showing the timing of sending of the modulated excitation light beam and reception of the scattered light beam in detail, which satisfies the lock condition when n=1, 2 in equation (13).

When the polarity of the error amplifier 402 is inverted as compared to the above case, the locked frequency f1 for satisfying the lock condition is generally represented as follows:

$$1/f1 = (4/(4n-3)) \cdot (Td+L/c) \quad (14)$$

Figure 25:
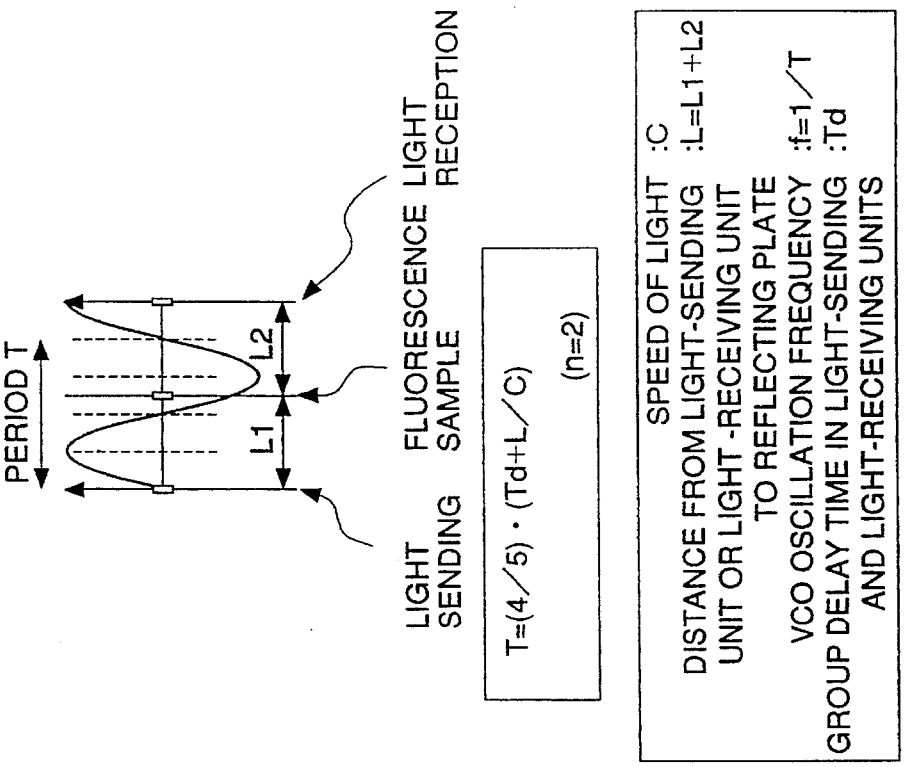
FIGS. 25 and 26 are views for explaining the lock condition of the decay characteristic measuring apparatus of the first embodiment.
Figure 26:
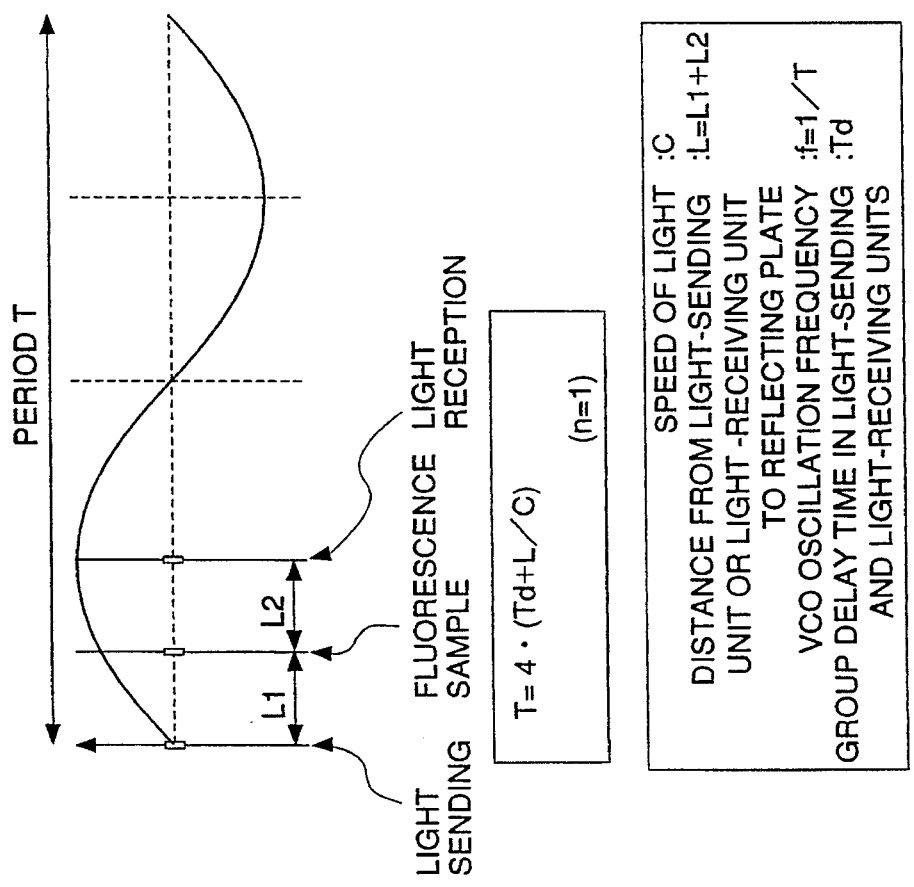

FIGS. 25 and 26 are views each showing the timing of sending of the modulated excitation light beam and reception of the scattered light beam in detail, which satisfies the lock condition when n=1, 2 in equation (14).

As is apparent from equations (13) and (14), the phase difference ($\Phi_1$) cannot be uniquely determined by only satisfying the lock condition. For this reason, the arithmetic processing unit 611 specifies the oscillation frequency range of the voltage-controlled oscillator 413 in advance. The value Td in equations (13) and (14) is normally known. When the value L is approximately known, the arithmetic processing unit 611 can designate measurement according to an arbitrary value n.

When the lock condition is satisfied, the arithmetic processing unit 611 reads the value of the oscillation frequency fi from the frequency counter 500 which is monitoring and measuring the oscillation frequency f1 of the output signal from the voltage-controlled oscillator 413 and stores the frequency value.

The arithmetic processing unit 611 subsequently designates the wavelength selector 200 to select and output a light beam having the wavelength=$\lambda_2$ as the wavelength of a reaction light beam (fluorescence). In this state, the light-receiving unit 300 is operated, and the bias voltage value output from the bias regulator 340 is adjusted such that the DC output voltage value from the light-receiving unit 300 becomes "0 V", as in the above case of the scattered light beam.

The voltage-controlled oscillator 413 is designated to select the oscillation frequency band. As in the above case of the scattered light, the oscillation frequency f2 for setting the phase difference ($\Phi_1+\Phi_2$) between the phase of the reaction light beam ($I_{RC}(\omega t+\Phi_1+\Phi_2)$) incident on the photoconductive photodetector 310 and the phase of the modulation voltage ($V_{M2}(t)$) applied to the photoconductive photodetector 310 to almost π/2 is measured and stored in the arithmetic processing unit 611. On the basis of the measured phase differences ($\Phi_1$) and ($\Phi_1+\Phi_2$), the lifetime τ as the decay characteristics of the reaction light beam is calculated in accordance with equation (11). The measured lifetime is displayed on the display unit 612.

The apparatus according to this embodiment has the following measurement precision, e.g., when ① an excitation light beam modulated with a frequency of 100 MHz is used, and ② the reaction light beam has a lifetime of about 2 ns. Under these conditions, the phase difference ($\Phi_2$) is estimated as 51.4881°.

In the conventional phase difference method, the measurement precision depends on the resolving power in phase reading. Since this resolving power is about 1/1000 (0.36°) the period, the influence to measurement of the lifetime τ is estimated as follows:

$$\Delta\tau = (\tan\Phi_2 - \tan(\Phi_2 - 0.36))/(2\pi \times 100 \times 10^6) \quad (15)$$
$$= 25.6 \text{ ps}$$

According to the apparatus of this embodiment, assuming that f1=100 MHz in equation (6), and a fluorescence sample having a lifetime of 2 ns is used, the following relation is derived from equations (10) and (11):

$$\tan[(\text{¾}) \times 2\pi \times (1-f2/(100 \times 10^6))] = 2\pi \times f2 \times \tau \quad (16)$$

Figure 27:
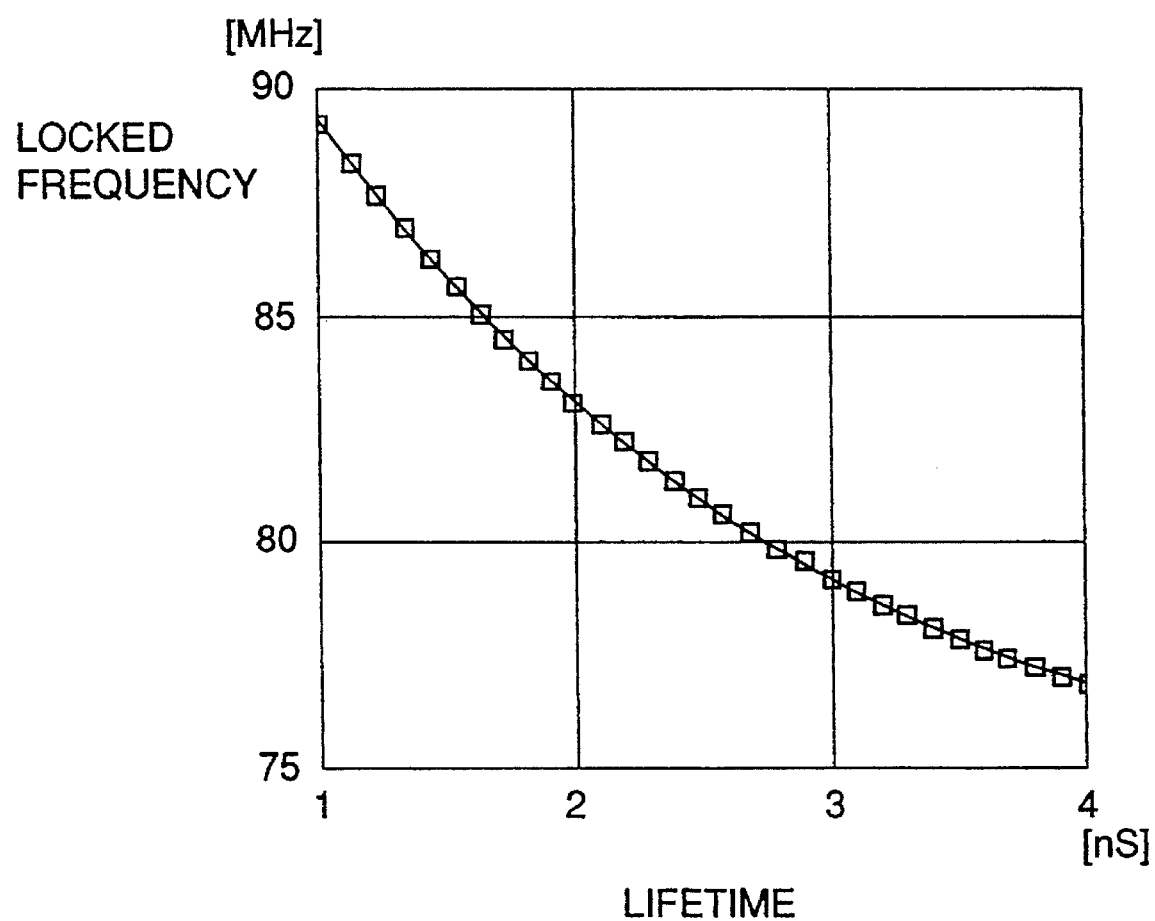
FIG. 27 is a graph showing the relationship between a lock frequency and a lifetime.

When f2=82.9 MHz is observed, the lifetime is specified as 2.00012 ns (FIG. 27). It is not difficult for the frequency counter used as a means for detecting a frequency to obtain a resolving power of six digits. Assume that the frequency resolving power is 100 Hz, and 82.8999 (82.9–0.0001) MHz is observed. In this case, the lifetime is specified as 2.00014 ns. Therefore, 0.02 ps is obtained as a lifetime resolving power.

In the apparatus of this embodiment, a time area on the order of subpico second is also subjected to measurement. For this reason, the timing drift (variations in group delay) in the electric circuit system or in the light-sending and light-receiving units has a value which cannot be neglected with respect to the measurement value. Equations (8) and (9) include the drift value. When the excitation light beam and fluorescence are measured without any delay, and the phase difference $\Phi_2$ is obtained, the influence of drift can be minimized. Assume that the group delay time in the light-sending and light-receiving units is not flat with respect to the frequency, and their values cannot be neglected in association with the precision of the measurement system in measurement of the frequencies f1 and f2. In this case, the values of the group delay time in the light-sending and light-receiving units with respect to the frequency are stored in the arithmetic processing unit 611 in advance. The measurement precision can be improved by correcting the delay time by, e.g., interpolation after measurement of the frequencies f1 and f2.

(Second Embodiment)

Figure 28:
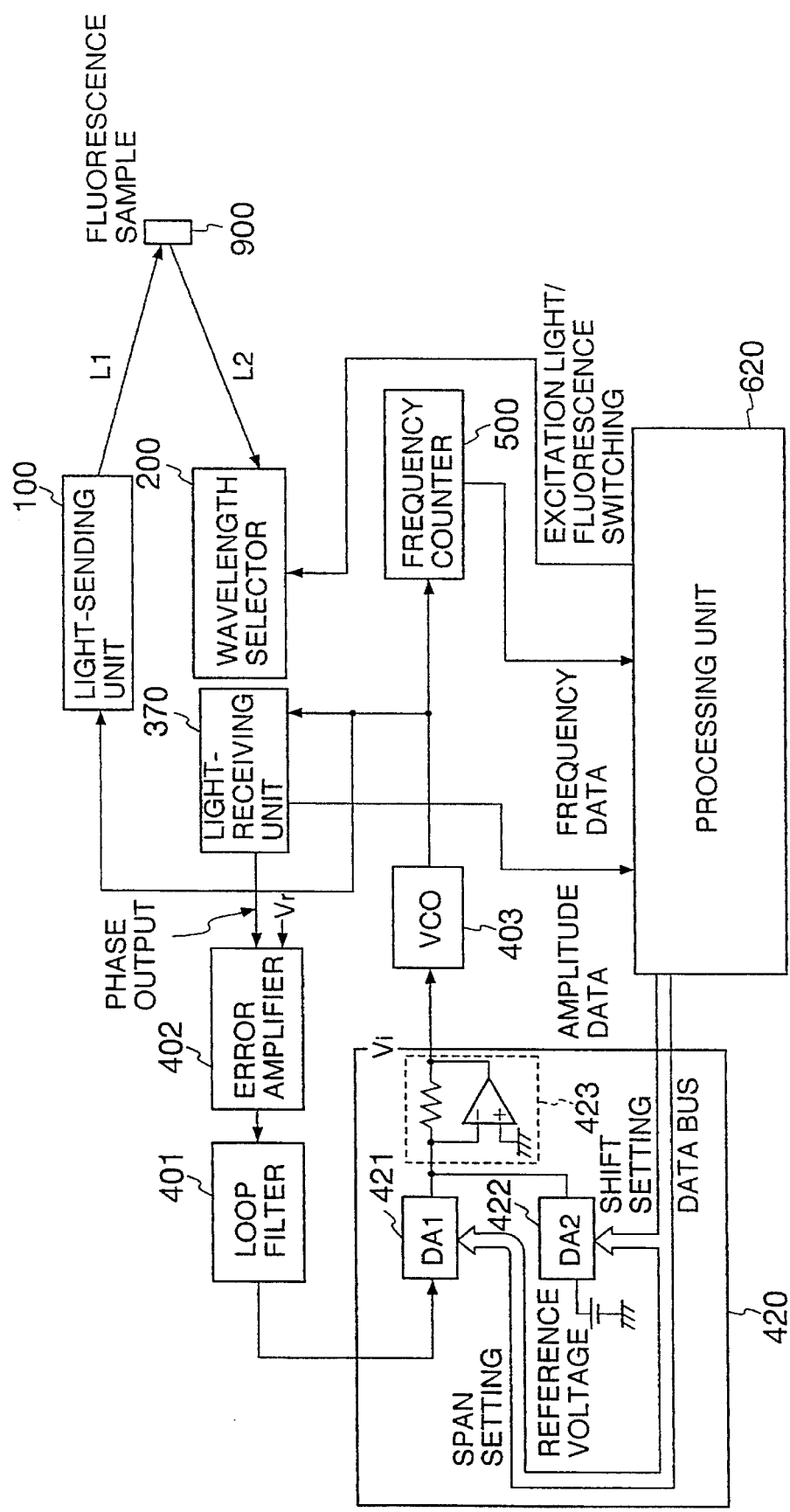
FIG. 28 is a block diagram showing the arrangement of a decay characteristic measuring apparatus of the second embodiment.

FIG. 28 is a block diagram showing the arrangement of a decay characteristic measuring apparatus according to the second embodiment of the present invention. This apparatus can obtain fluorescence decay characteristics approximated by a polynomial exponential function. As shown in FIG. 28, the apparatus of this embodiment comprises, in addition to the apparatus of the first embodiment, ① a control voltage generation unit 420 for receiving an output signal from a DC amplifier 402 and generating a control voltage to be supplied to a voltage-controlled oscillator 403, ② in place of the light-receiving unit 300, a light-receiving unit 370 for outputting an amplitude output in addition to a phase difference output, and ③ in place of the processing unit 610 of the apparatus of the first embodiment, a processing unit 620 for issuing a generation voltage designation to the control voltage generation unit 420, and reading the measurement value of a frequency counter 500 and the measurement value of a peak detector 520, thereby measuring the decay characteristics of a reaction light beam.

The control voltage generation unit 420 comprises ① a multiplication type D/A converter 421, ② a D/A converter 422, ③ a summing converter 423. The multiplication type D/A converter 421 outputs a current value corresponding to the voltage value output from the DC amplifier 402 within a range of an output current value designated by the processing unit 620. The D/A converter 422 outputs a current value designated by the processing unit 620. The summing converter 423 adds the output current from the multiplication type D/A converter 421 and the output current from the D/A converter 422, converts it into a voltage value corresponding to the sum current value, and outputs the voltage value to the voltage-controlled oscillator 403.

The multiplication type D/A converter 421 has a function of dividing an input voltage from the DC amplifier 402 by a digital span setting input from the processing unit 620 and outputting the result. When the maximum value of span setting is 255 (8bit), a set value "51" is given. When the output voltage from the DC amplifier 402 is 5 V, a current value corresponding to 1 V (5 V×51/255) is output from the multiplication type D/A converter 421. When an oscillation frequency of 100 to 600 MHz linearly corresponds to an output range of 0 to 5 V of the DC amplifier 402 and the control voltage range of 0 to 5 V of the voltage-controlled oscillator 403, span setting with the value "51" means that the frequency range is limited to 1/5 the maximum frequency deviation of 500 MHz (e.g., 100 MHz in a range of 100 to 200 MHz). Shift setting to the D/A converter 422 is used to set the shift amount with respect to an operational amplifier A3 of the summing converter 423 and determine the usable frequency range. When the frequency variable range is set to 100 MHz by span setting, as described above, a use point in the range of 100 to 600 MHz is determined.

Figure 29:
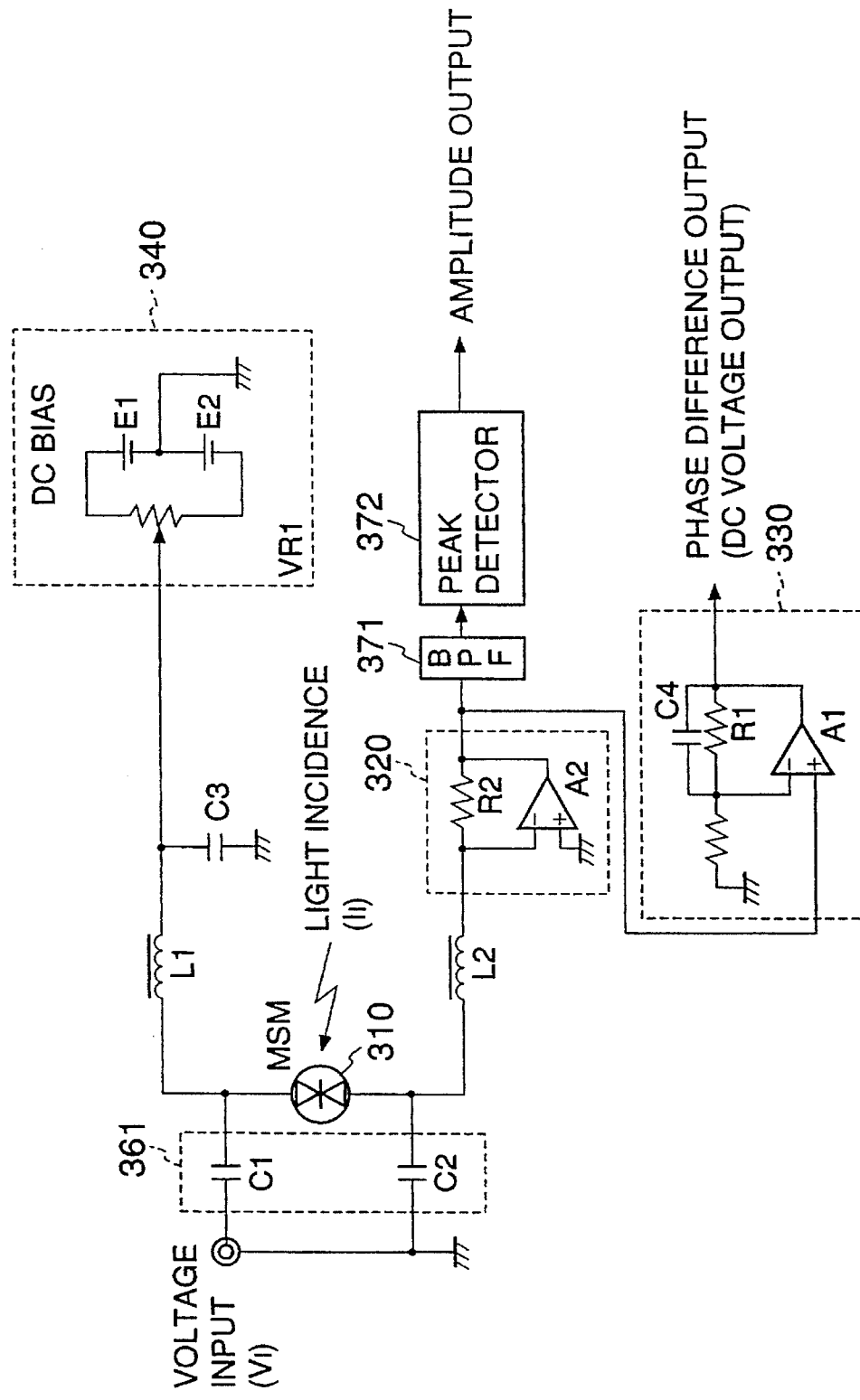
FIG. 29 is a block diagram showing an arrangement of a light-receiving unit of the second embodiment.

FIG. 29 is a block diagram showing the arrangement of the light-receiving unit 370. As shown in FIG. 29, the light-receiving unit 370 comprises, in addition to the light-receiving unit 300 shown in FIG. 2, ① a band-pass filter 371 and ② a peak detector 372. The band-pass filter 371 receives an AC voltage output, and selects and outputs a signal having a frequency about twice that of the modulation signal. The peak detector 372 measures the amplitude value of the signal output from the band-pass filter 371 and outputs an amplitude signal.

Figure 30:
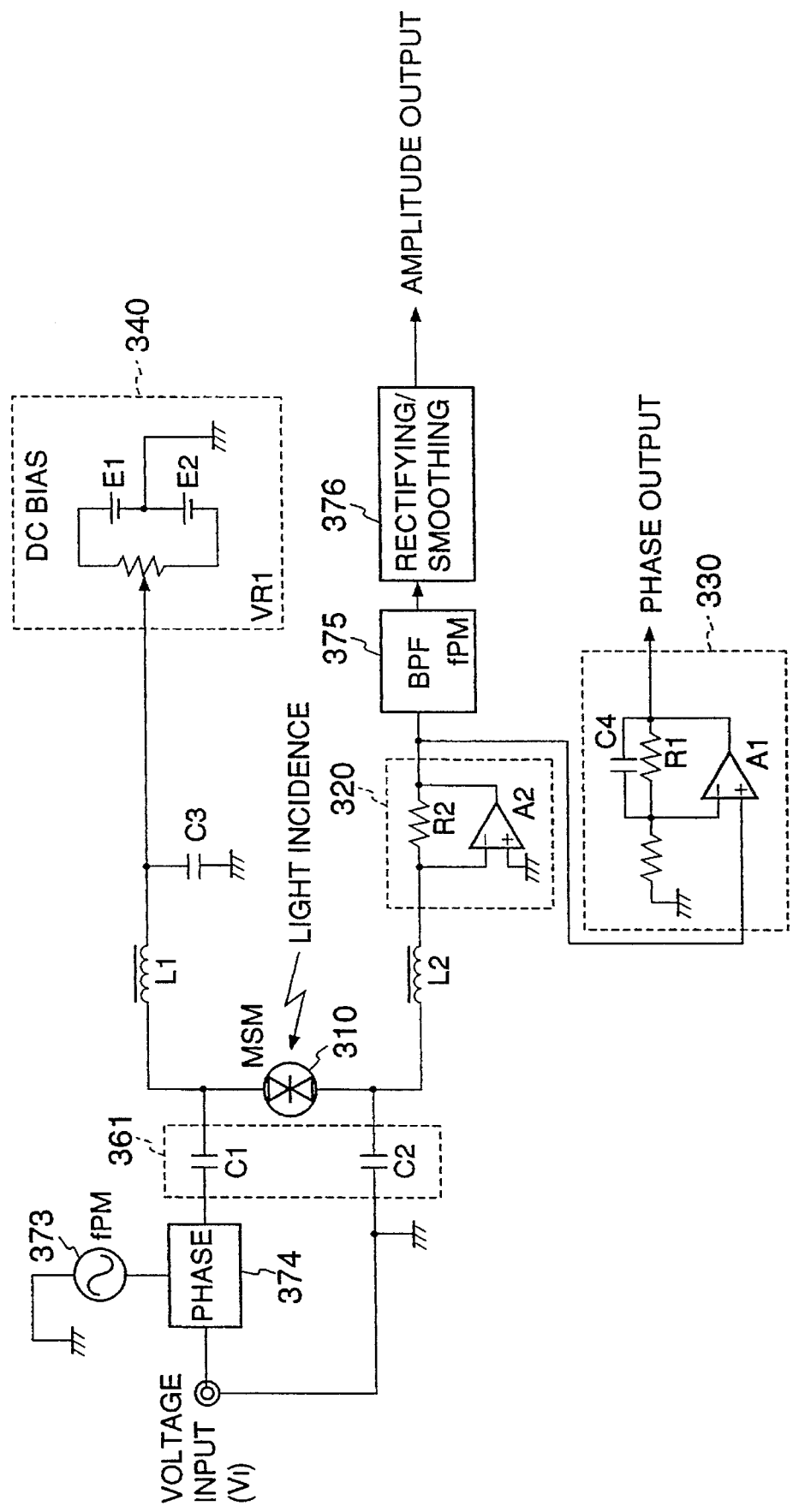
FIG. 30 is a block diagram showing another arrangement of the light-receiving unit of the second embodiment.

FIG. 30 is a block diagram showing the arrangement of a light-receiving unit usable in this embodiment and different from that shown in FIG. 29. The light-receiving unit shown in FIG. 30 comprises, in addition to the light-receiving unit 300 shown in FIG. 2, ① an oscillator 373, ② a phase modulator 374, ③ a band-pass filter 375, and ④ an amplitude detector 376. The oscillator 373 generates a signal having a frequency ($f_{PM}$; $f_{PM}$<frequency $f_M$ of voltage input $V_I$) higher than the loop bandwidth, which does not affect the characteristics of a PLL in formation of a phase-locked loop. The phase modulator 374 receives the modulation signal (voltage input $V_I$; frequency=$f_M$) and an output signal from the oscillator 373 and phase-modulates the modulation signal. The band-pass filter 375 receives the AC voltage output, and selects and outputs a signal having a frequency almost equal to the frequency $f_{PM}$. The amplitude detector 376 rectifies/smoothes the signal output from the band-pass filter 375.

The current signal generated in a photoconductive photodetector 310 is converted into a voltage signal by a current-to-voltage converter 320. During the operation of the PLL, when a reference voltage (Vr) of the error amplifier 402 is set to "0 V", an average output (DC component) from the current-to-voltage converter 320 is kept to be zero because the gain with respect to the DC component of the error amplifier 402 and a loop filter 401 is almost infinite. Therefore, an AC voltage having an amplitude proportional to the modulation component of the incident light amount appears, which AC voltage is generated upon phase modulation with the frequency $f_{PM}$ higher than the loop bandwidth. The AC voltage signal passes through the band-pass filter 375 for selecting only a frequency component almost equal to the phase modulation frequency $f_{PM}$, is converted into a DC voltage proportional to the amplitude modulation component of the incident light by the amplitude detector 376, and output. The AC voltage signal output from the current-to-voltage converter 320 is supplied to a low-pass filter 330. A phase modulation component is removed by a non-inverting amplifier constituted by an operational amplifier A1 for a cutoff frequency determined by a time constant R1·C4 to convert the AC voltage signal into a DC voltage signal. The voltage signal is supplied to the error amplifier 402 as a phase difference output.

The arithmetic processing unit 620 sets a frequency range for the voltage-controlled oscillator 403 such that the frequency to be locked is limited to one point by span setting. The usable frequency range is gradually shifted by shift setting to gradually change the locked frequency. Every time the locked frequency is changed, the intensities of the excitation light beam and the fluorescence, and the oscillation frequency of the voltage-controlled oscillator 403, which depends on the phase difference between the excitation light beam and the fluorescence, are recorded. The locked frequency at this time is based on equation (13) or (14). When the fluorescence intensity and the phase difference are obtained for each frequency, the fluorescence decay component is determined by curve fitting.

(Third Embodiment)

Figure 31:
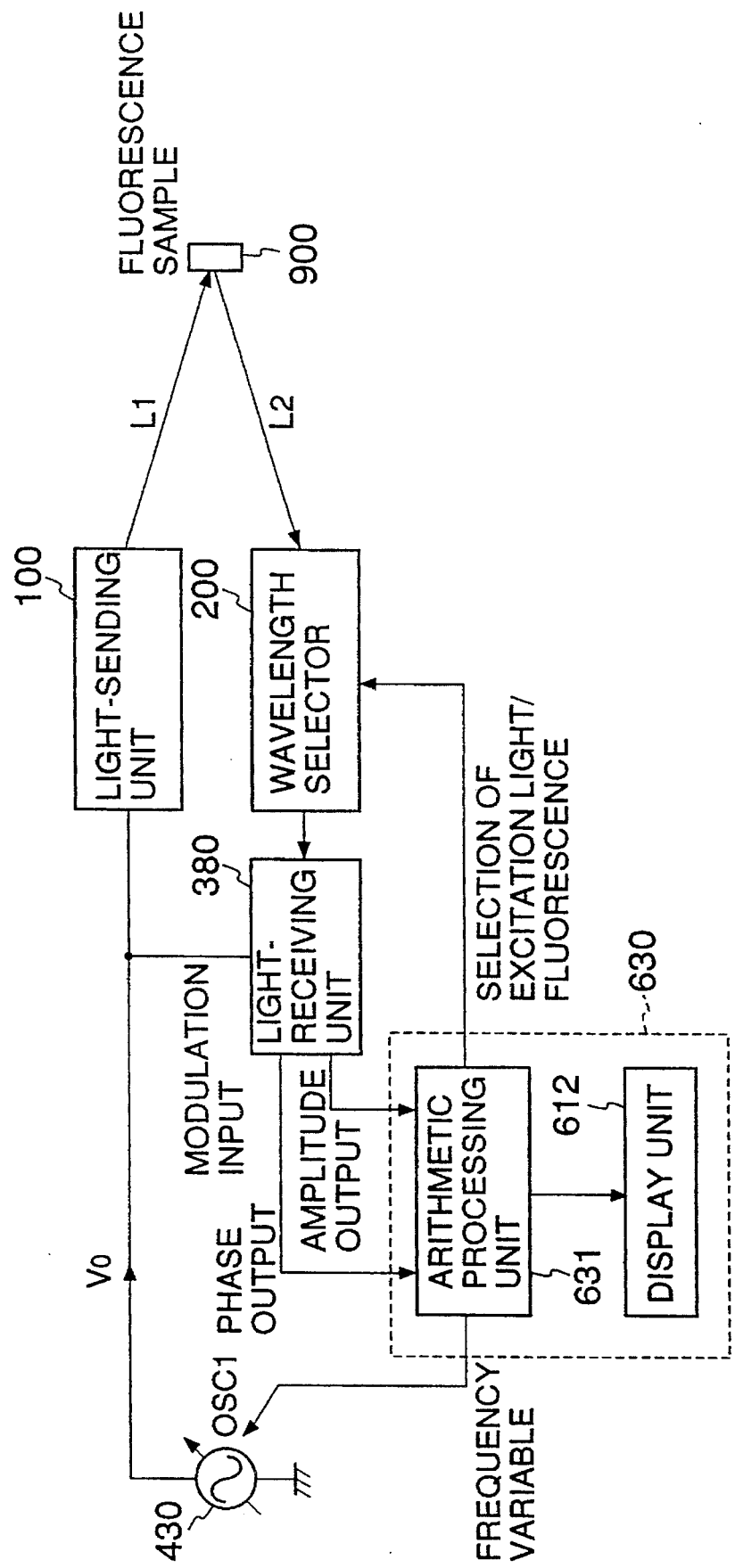
FIG. 31 is a block diagram showing the arrangement of a decay characteristic measuring apparatus of the third embodiment.

FIG. 31 is a block diagram showing the arrangement of a decay characteristic measuring apparatus according to the third embodiment of the present invention. This apparatus directly measures the decay characteristics from the phase difference by using a phase comparator using a photoconductive photodetector instead of forming a PLL feedback loop. As shown in FIG. 31, this apparatus comprises (a) a variable frequency oscillator 430, (b) a light-sending unit 100, (c) a wavelength selector 200, (d) a light-receiving unit 380, and (e) a processing unit 630. The variable frequency oscillator 430 generates a modulation signal having a frequency according to a designation from the outside. The light-sending unit 100 receives the modulation signal from the variable frequency oscillator 430 and outputs an excitation light beam $I_{EX}(t)$ having a wavelength=$\lambda_1$, which is intensity-modulated with the modulation signal, to a target measurement object 900. The wavelength selector 200 receives a reaction light beam and a scattered light beam, and selects and outputs one of the light beams in accordance with a designation from the outside. The light-receiving unit 380 receives the modulation signal and the light beam output from the wavelength selector 200, generates a current signal corresponding to the product of the intensity of the received light and the modulation signal, and thereafter, outputs a phase difference signal reflecting the phase difference between the received light and the modulation signal and an amplitude signal reflecting the amplitude of the AC component of the current signal. The processing unit 630 outputs an oscillation frequency designation signal to the variable frequency oscillator 430 and a wavelength selection designation signal for designating the selected wavelength ($\lambda_1$ or $\lambda_2$) to the wavelength selector 200. When the wavelength= $\lambda_1$ is selected, the processing unit 630 obtains a phase difference $\Phi_1$ between a modulation signal $V_{M2}(t)$ and a scattered light beam $I_{RF}(t+\Phi_1)$ from the signal output from the light-receiving unit 380. When the wavelength=$\lambda_2$ is selected, the processing unit 630 obtains a phase difference $(\Phi_1+\Phi_2)$ between the modulation signal $V_{M2}(t)$ and a reaction light beam $I_{RC}(t+\Phi_1+\Phi_2)$ from the signal output from the light-receiving unit 380. The processing unit 630 obtains the decay characteristics of the reaction light beam in accordance with the two phase differences, i.e., $\Phi_2$.

Figure 32:
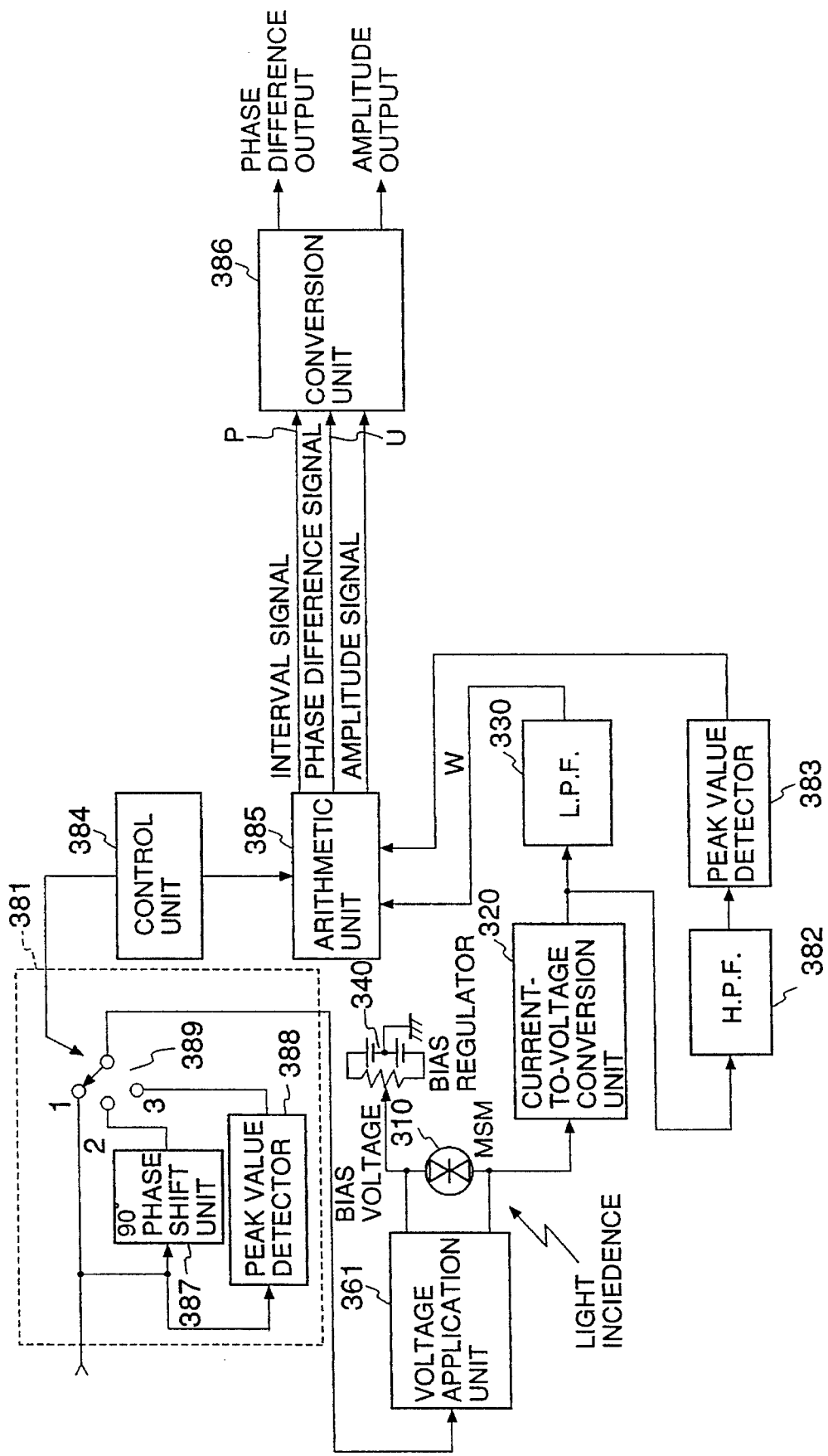
FIG. 32 is a block diagram showing the arrangement of a light-receiving unit of the third embodiment.

FIG. 32 is a block diagram showing the arrangement of the light-receiving unit 380 of the apparatus of this embodiment. As shown in FIG. 32, the light-receiving unit 380 comprises, in addition to the light-receiving unit 300 shown in FIG. 2, (a) a signal selection unit 381, (b) a high-pass filter (HPF) 382, (c) a peak value detector 383, (d) a control unit 384, (e) an arithmetic unit 385, and (f) a conversion unit 386. The signal selection unit 381 selects a signal to be supplied to a voltage application unit 361. The high-pass filter 382 receives a signal output from an AC output (ACO) of a current-to-voltage converter 320, removes the DC component, and outputs the signal. The peak value detector 383 receives the signal output from the high-pass filter 382 and measures the peak value. The control unit 384 issues a selection designation to the signal selection unit 381. The arithmetic unit 385 receives an output signal from a low-pass filter 330 and an output signal from the peak value detector 383, and outputs an interval signal representing an interval between the normalized phase difference signal and the phase difference in accordance with the selection designation from the control unit 384. The conversion unit 386 receives the normalized phase difference signal and the interval signal, converts the signals into a phase difference, and uniquely outputs a phase difference with respect to the phase difference.

The signal selection unit 381 is constituted by ① a phase shifter 387, ② a peak detector 388, and ③ a switch 389. The phase shifter 387 shifts the phase of a received electrical signal by $\pi/2$. The peak detector 388 measures the peak value of the received electrical signal. The switch 389 selects one of the received electrical signal (selection 1), an output from the phase shifter 387 (selection 2), and an output signal from the peak detector 388 (selection 3) in accordance with the selection designation from the control unit 384, and supplies the selected signal to the voltage application unit 361.

The control unit 384 notifies the switch 389 and the arithmetic unit 385 of a selection designation for selection 3. Upon this setting, the output value from the high-pass filter 382 is maximized. The arithmetic unit 385 receives and accumulates a value V.

Figure 33:
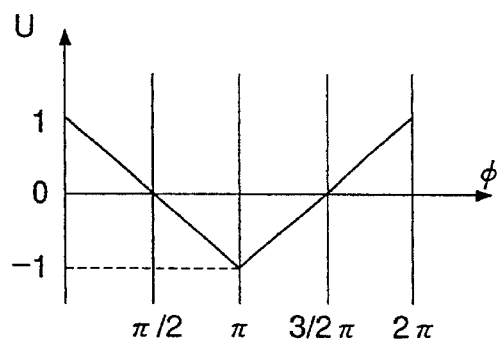
FIG. 33 is a graph for explaining the operation of the third embodiment.

The control unit 384 notifies the switch 389 and the arithmetic unit 385 of a selection designation for selection 1. The arithmetic unit 385 receives a value W, divides the value W by the value V, and outputs a normalized phase difference signal U. FIG. 33 is a graph showing a change in phase difference signal U with respect to a phase difference $\Phi$, which is observed when a rectangular wave at a duty ratio of 50% is received. The phase difference signal U does not depend on the amplitude value of the voltage signal and the intensity value of the optical signal, which are supplied to the photoconductive photodetector 310. For this reason, when this phase difference signal U is used, phase difference detection independent of the amplitude value of the voltage signal and the intensity value of the optical signal, which are supplied to the photoconductive photodetector 310, can be performed.

As described above, when indefiniteness of phase difference is in a range of 0 to $\pi$ or $\pi$ to $2\pi$, a phase difference can be uniquely obtained from the value of the phase difference signal U.

Figure 34:
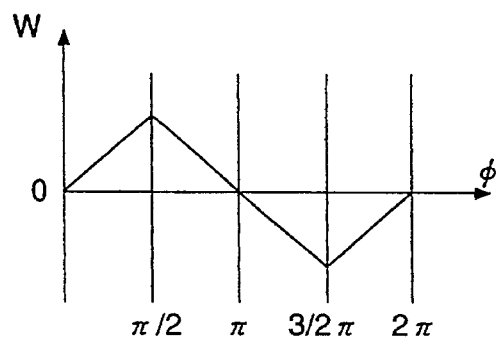
FIG. 34 is a graph for explaining another operation of the third embodiment.
Figure 35:
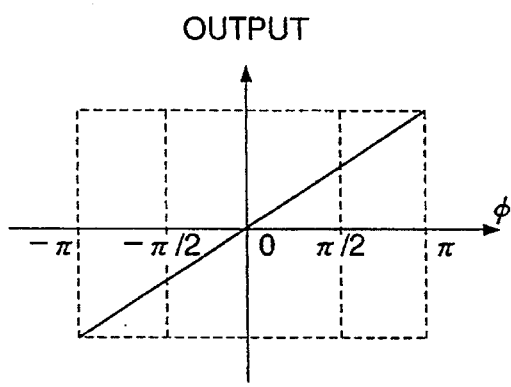
FIG. 35 is a graph for explaining still another operation of the third embodiment.

However, when the indefiniteness of phase difference is in a range of 0 to $2\pi$, two phase difference values are obtained as candidates with respect to the single phase difference signal U, as is apparent from FIG. 33, so the phase difference value cannot be uniquely determined by only the above measurement. In this case, subsequent to the above measurement, the control unit 384 notifies the switch 389 and the arithmetic unit 385 of a selection designation for selection 2. Upon this setting, the output value from the low-pass filter 330 is a value obtained by replacing $\Phi$ with $(\Phi+\pi/2)$, and a graph shown in FIG. 34 is obtained. As is apparent from this graph, when the phase difference is in a range of 0 to $\pi$, the value W is positive. When the phase difference is in a range of π to 2π, the value W is negative. The arithmetic unit 385 receives the value W and outputs the positive/negative information of the value W as an interval signal. The conversion unit 386 receives this positive/negative information and the phase difference signal U, converts these data into a unique phase difference value, and outputs a phase difference output signal as shown in FIG. 35. Generation of the interval signal and the operation of the conversion unit 386 can also be applied even when the indefiniteness of phase difference is in a range of 0 to π or π to 2π.

According to the apparatus of this embodiment, the bias regulator 340 is adjusted as in the first embodiment, and thereafter, the processing unit 630 fixes the oscillation frequency of the variable frequency oscillator 430 to a certain value and alternately selects the excitation light beam and the fluorescence of the received light, thereby obtaining the phase difference between the excitation light beam and the fluorescence and obtaining the modulation amplitude data. The frequency of the variable frequency oscillator 430 is changed, and the same processing as described above is performed, thereby accumulating the fluorescence amplitude and the phase difference data with respect to the frequency and calculating the lifetime.

(Fourth Embodiment)

Figure 36:
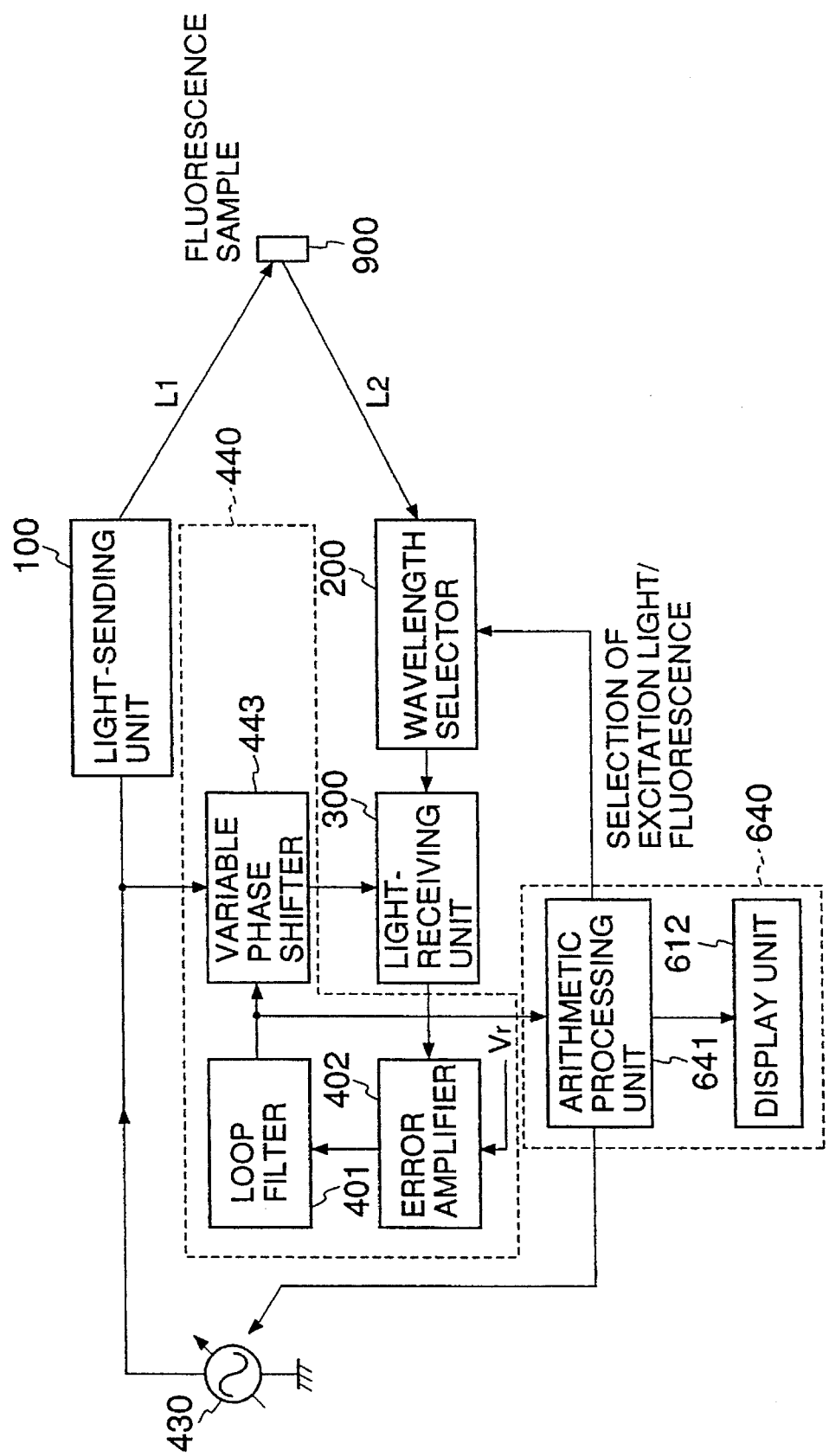
FIG. 36 is a block diagram showing the arrangement of a decay characteristic measuring apparatus of the fourth embodiment.

FIG. 36 is a block diagram showing the arrangement of a decay characteristic measuring apparatus according to the fourth embodiment of the present invention. This apparatus is different from that of the first embodiment in that a variable phase shifter for changing the phase is used in place of the voltage-controlled oscillator for changing the modulation frequency as a control target for phase lock. In this embodiment, a variable phase shifter for changing the phase difference between input and output signals in accordance with an applied voltage is used as a variable phase shifter. More specifically, the apparatus of this embodiment comprises (a) a variable frequency oscillator 430, (b) a light-sending unit 100, (c) a wavelength selector 200, (d) a light-receiving unit 300, (e) a phase adjustment unit 440, and (f) a processing unit 640. The variable frequency oscillator 430 generates a modulation signal having a frequency corresponding to a designation from the outside. The light-sending unit 100 receives the modulation signal from the variable frequency oscillator 430 and outputs an excitation light beam $I_{EX}(t)$ having a wavelength=$\lambda_1$, which is intensity-modulated with the modulation signal, to a target measurement object 900. The wavelength selector 200 receives a reaction light beam and a scattered light beam, and selects and outputs one of the light beams in accordance with a designation from the outside. The light-receiving unit 300 receives the modulation signal and the light beam output from the wavelength selector 200, generates a current signal corresponding to the product of the intensity of the received light beam and the modulation signal, and thereafter, outputs a phase difference signal reflecting the phase difference between the received light beam and the modulation signal and an amplitude signal reflecting the amplitude of the AC component of the current signal. The phase adjustment unit 440 outputs a modulation signal having a phase difference between input and output signals corresponding to the voltage value of an almost DC voltage signal output from the light-receiving unit 300. The processing unit 640 outputs an oscillation frequency designation signal to the variable frequency oscillator 430 and a wavelength selection designation signal for designating the selected wavelength ($\lambda_1$ or $\lambda_2$) to the wavelength selector 200. When the wavelength=$\lambda_1$ is selected, the processing unit 640 obtains a phase difference $\Phi_1$ between a modulation signal $V_M(t)$ and a scattered light beam $I_{RF}(t+\Phi_1)$ from a phase difference control signal output from the phase adjustment unit 440. When the wavelength=$\lambda_2$ is selected, the processing unit 640 obtains a phase difference $-(\Phi_1+\Phi_2)$ between the modulation signal $V_M(t)$ and a reaction light beam $I_{RC}(t+\Phi_1+\Phi_2)$ from the phase difference control signal output from the phase adjustment unit 440. The processing unit 640 obtains the decay characteristics of the reaction light beam in accordance with the two phase differences, i.e., $\Phi_2$.

The phase adjustment unit 440 comprises ① an error amplifier 402, ② a loop filter 401, and ③ a variable phase shifter 443. The error amplifier 402 receives the DC voltage output signal from the light-receiving unit 300, amplifies the difference with respect to a reference voltage (Vr), and outputs the signal. The loop filter 401 receives the signal output from the error amplifier 402 and passes only the almost DC component. The variable phase shifter 443 outputs a phase shift amount corresponding to the voltage value of the DC voltage signal output from the loop filter 401, i.e., the modulation signal having the phase difference between the input and output signals.

The processing unit 640 comprises ① an arithmetic processing unit 641 and ② a display unit 612. The arithmetic processing unit 641 outputs an oscillation frequency designation signal to the variable frequency oscillator 430 and issues a wavelength selection designation signal to the wavelength selector 200. At the same time, the arithmetic processing unit 641 reads the voltage value of the input voltage signal to the variable phase shifter 443 and obtains phase differences between the intensity-modulated scattered and reaction light beams and the modulation signal, and thereafter, calculates the decay characteristics of the reaction light beam. The display unit 612 displays the calculation result from the arithmetic processing unit 641 in accordance with a designation from the arithmetic processing unit 641.

As in the first embodiment, the arithmetic processing unit 641 of the processing unit 640 designates the wavelength selector 200 to select and output a light beam having the wavelength=$\lambda_1$ as the wavelength of an excitation light beam. In this state, the light-receiving unit 300 is operated, and the bias voltage value output from a bias regulator 340 is adjusted such that the DC output voltage value from the light-receiving unit 300 becomes "0 V".

The arithmetic processing unit 641 designates the oscillation frequency to the variable frequency oscillator 430. Upon reception of the oscillation frequency designation, a variable frequency oscillator 430 oscillates the designated frequency and outputs the oscillation signal to the light-sending unit 100 and the light-receiving unit 300 as a modulation signal. The light-sending unit 100 generates an excitation light beam which is intensity-modulated in accordance with the modulation signal.

The laser beam output from the light-sending unit 100 is irradiated on the target measurement object 900 as an excitation light beam. On the target measurement object 900 irradiated with the excitation light beam, part of the excitation light beam is scattered, and fluorescence is generated. The scattered component of the excitation light beam and part of the fluorescence are guided to the wavelength selector 200. The wavelength selector 200 separates the scattered component (to be referred to as a scattered light beam hereinafter) of the excitation light beam from the fluorescence in accordance with the wavelength selection designation from the processing unit 641, and outputs the scattered light beam to the light-receiving unit 300.

The scattered light beam supplied to the light-receiving unit 300 is received by a photoconductive photodetector 310. An AC voltage is applied to the photoconductive photodetector 310 of the light-receiving unit 300 through a capacitor. A current depending on a phase difference is supplied to a current-to-voltage converter 320 by inductor coupling such that the applied voltage component is not directly output. Since the conversion gain of the photoconductive photodetector 310 is modulated in accordance with the applied voltage, an output current depending on a phase difference with respect to the incident light which is intensity-modulated with the same frequency is obtained. The output current is integrated with the time constant of a low-pass filter 330, converted into a DC voltage depending on the phase difference, and output. As in the first embodiment, when the phase difference between the applied voltage and the incident light is $\pi/2$ (+$n\pi$), the DC voltage output from the light-receiving unit 300 is "0 V". In accordance with delay or advance of the phase, a DC voltage output with an inverted polarity is obtained. An output from the light-receiving unit 300 serving as a phase comparator is amplified by the error amplifier 402 and the loop filter 401, both of which are set to obtain the optimal response of the system, and supplied to the control voltage input terminal of the variable phase shifter 443. Therefore, the current signal represented by equation (3) is generated in the photoconductive photodetector 310. The current signal generated in the photoconductive photodetector 310 sequentially passes through the current-to-voltage converter 320 and the low-pass filter 330, and a DC voltage signal $V_{DC}$ represented by equation (5) is output. The DC voltage signal $V_{DC}$ output from the light-receiving unit 300 is amplified by the error amplifier 402, guided to the loop filter 401, limited to a necessary band therein, and supplied to the variable phase shifter 443 as a control voltage. The variable phase shifter 443 determines the phase shift amount in accordance with the control voltage value. More specifically, when the phase shift amount is smaller than the locked phase difference, the phase shift amount is controlled to become larger. To the contrary, when the phase shift amount is larger than the locked phase difference, the phase shift amount is controlled to become smaller. When a gain G of the error amplifier 402 is set to be sufficiently high, and the reference voltage value (Vr) is "0 V", the phase difference ($\Phi_1$) between the phase of the scattered light beam ($I_{SC}(\omega t + \Phi_1)$) incident on the photoconductive photodetector 310 and the phase of a modulation voltage ($V_{M2}(t)$) applied to the photoconductive photodetector 310 is obtained as almost $\pi/2$ (+$n\pi$; n=integer) in accordance with equation (7).

When the lock condition is satisfied, the arithmetic processing unit 641 reads the voltage value of the input signal to the variable phase shifter 443 and stores the voltage value.

The arithmetic processing unit 641 of the processing unit 640 designates the wavelength selector 200 to select and output a light beam having the wavelength=$\lambda_2$ as the wavelength of a reaction light beam (fluorescence). In this state, the light-receiving unit 300 is operated, and the bias voltage value output from the bias regulator 340 is adjusted such that the DC output voltage value from the light-receiving unit 300 becomes "0 V", as in the above case of the scattered light beam.

As in the above case of the scattered light beam, the phase shift amount for setting the phase difference ($\Phi_1+\Phi_2$) between the phase of the reaction light beam ($I_{RC}(\omega t+\Phi_1+\Phi_2)$) incident on the photoconductive photodetector 310 and the phase of the modulation voltage ($V_{M2}(t)$) applied to the photoconductive photodetector 310 to almost $\pi/2$ is measured and stored in the arithmetic processing unit 641. On the basis of the measured phase differences ($\Phi_1$) and ($\Phi_1+\Phi_2$), a lifetime $\tau$ as the decay characteristics of the reaction light beam is calculated in accordance with equation (11). The measured lifetime is displayed on the display unit 612.

The phase shift amount with respect to the control voltage of the variable phase shifter 443 must be known in advance. The processing unit 641 can obtain the frequency vs. phase characteristics of the sample by repeating the measurement while changing the oscillation frequency of the variable frequency oscillator 430. In addition, when the light-receiving unit as shown in FIG. 29 or 30 is used, the frequency vs. amplitude characteristics can also be simultaneously obtained.

(Fifth Embodiment)

Figure 37:
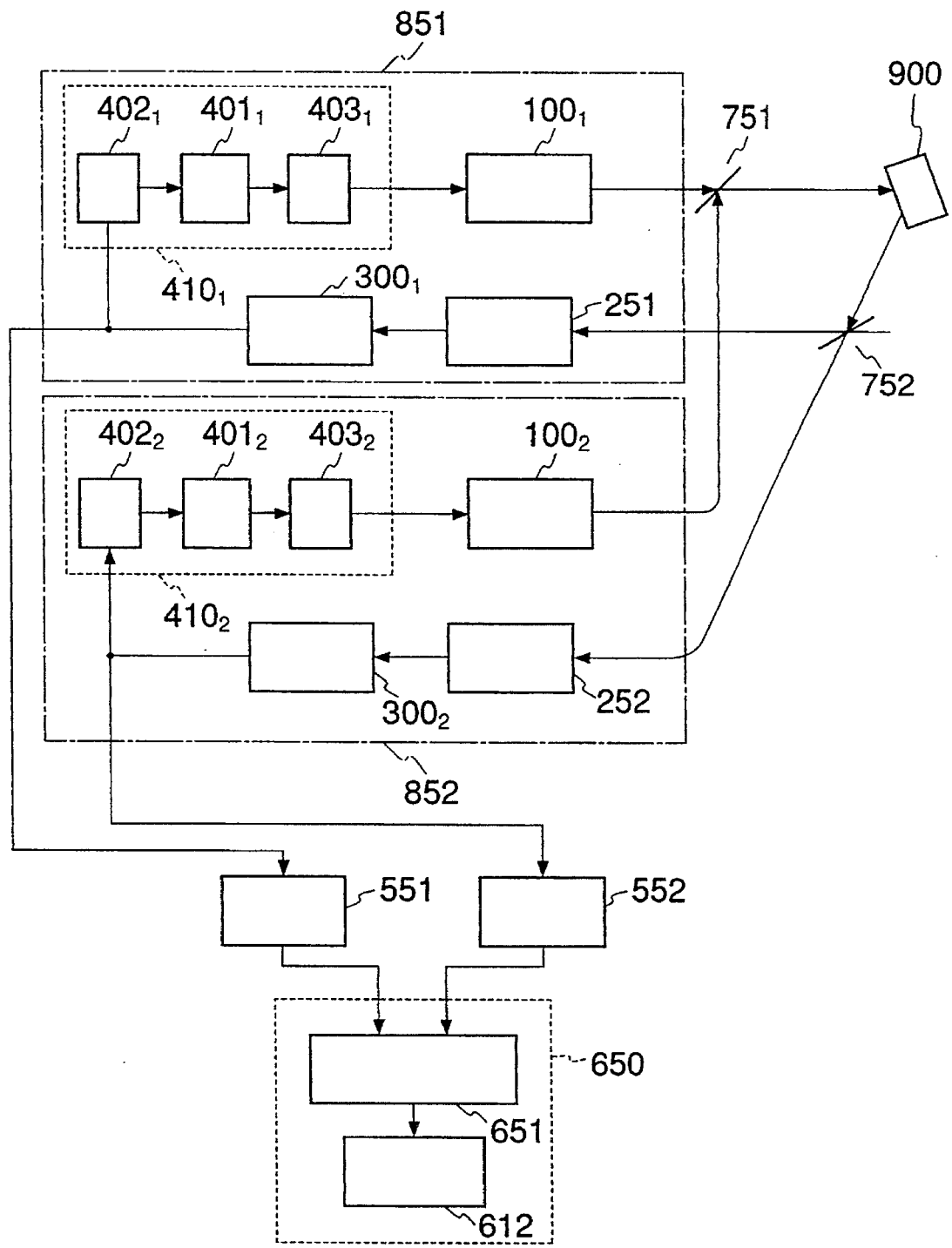
FIG. 37 is a block diagram showing the arrangement of a decay characteristic measuring apparatus of the fifth embodiment.

FIG. 37 is a block diagram showing the arrangement of a decay characteristic measuring apparatus according to the fifth embodiment of the present invention. In each of the above embodiments, when distances L1 and L2 to the target measurement object vary in a series of procedures for performing measurement while switching between the scattered light beam and the reaction light beam by the wavelength selection unit, accurate decay characteristics cannot be obtained. The apparatus of this embodiment is preferable to solve this problem. More specifically, in this apparatus, a phase-locked loop associated with a scattered light beam and a phase-locked loop associated with a reaction light beam are simultaneously formed, and phase differences with respect to a modulation signal are simultaneously measured, thereby allowing to neglect the distances L1 and L2 to the target measurement object. As shown in FIG. 37, this apparatus comprises (a) a lock system 851, (b) a lock system 852, (c) a frequency counter 551, (d) a frequency counter 552, (e) a processing unit 650, (f) a multiplexing mirror 751, and (g) a branching mirror 752. The lock system 851 forms a phase-locked loop associated with a scattered light beam. The lock system 852 forms a phase-locked loop associated with a reaction light beam. The frequency counter 551 monitors and measures the frequency of a modulation signal in the lock system 851. The frequency counter 552 monitors and measures the frequency of a modulation signal in the lock system 852. The processing unit 650 reads the measurement value of the frequency counter 551 when the lock system 851 forms the phase-locked loop, reads the measurement value of the frequency counter 552 when the lock system 852 forms the phase-locked loop, and obtains the decay characteristics of the reaction light on the basis of the read measurement values. The multiplexing mirror 751 multiplexes part of an excitation light beam output from the lock system 851 and part of an excitation light beam output from the lock system 852 and outputs the light beam to a target measurement object 900. The branching mirror 752 receives the scattered light beam and the reaction light beam from the target measurement object 900 and branches each light beam into two light beams containing a scattered light component and a reaction light component.

The lock system 851 is different from the lock system 800 of the first embodiment only in that a wavelength selector 251 for selectively transmitting a light beam having a wavelength=$\lambda_1$ is used in place of the wavelength selector 200. The lock system 852 is different from the lock system 800 of the first embodiment only in that a wavelength selector 252 for selectively transmitting a light beam having a wavelength=$\lambda_2$ is used in place of the wavelength selector 200.

The apparatus of this embodiment measures the decay characteristics of a reaction light beam in the following manner.

The bias regulators of light-receiving units $300_1$ and $300_2$ of the lock systems 851 and 852 are adjusted to set the output voltage value of a DC output from the light-receiving unit $300_1$ and the output voltage value of a DC output from the light-receiving unit $300_2$ to almost "0 V". Subsequently, an excitation light beam is output from each lock system.

Light-sending units $100_1$ and $100_2$ for generating excitation light beams are respectively driven by voltage-controlled oscillators $403_1$ and $403_2$ to generate excitation light beams which are intensity-modulated with the respective frequencies. A light beam output from the light-sending unit $100_1$ and a light beam output from the light-sending unit $100_2$ are aligned on the same optical path through the multiplexing mirror 751 and irradiated on the target measurement object 900. Of the scattered light component of the excitation light beam generated on the target measurement object 900 and the reaction light component associated with the decay characteristics, a component aligned on the specific optical path is branched and guided to the wavelength selector 251 for selecting only the excited wavelength $\lambda_1$ and the wavelength selector 252 for selecting only the reaction wavelength $\lambda_2$. The light beam passing through the wavelength selector 251 is supplied to the light-receiving unit $300_1$ while the light beam passing through the wavelength selector 252 is supplied to the light-receiving unit $300_2$. Each lock system forms a phase-locked loop, as in the first embodiment. More specifically, the phase lock operation associated with the scattered light beam and the phase lock operation associated with the reaction light beam are independently and simultaneously executed by the respective lock systems.

After the phase-locked loops are formed by the two lock systems, the processing unit 650 reads the frequency measurement value of the frequency counter 551 and the frequency measurement value of the frequency counter 552. Thereafter, the decay characteristics of the reaction light beam are calculated and displayed, as in the first embodiment.

According to the apparatus of this embodiment, as compared to the apparatus of the first embodiment, a lot of time required for switching the wavelength can be saved, and high-speed measurement which is limited by only the PLL response frequency and the data processing time can be performed.

(Sixth Embodiment)

To achieve a maximum resolving power in measurement, it is preferable to easily set the entire apparatus to conditions for obtaining the maximum sensitivity. To maximize the sensitivity for phase difference detection, the phase delay of a scattered light beam or a reaction light beam obtained with respect to an excitation light beam preferably falls within a range of 30° to 60°. For this purpose, it is appropriate to use an offset phase-locked loop technique disclosed in, e.g., Japanese Patent Laid-Open No. 63-308596) such that the oscillation frequency of the system is automatically fixed to set such a phase difference.

Figure 38:
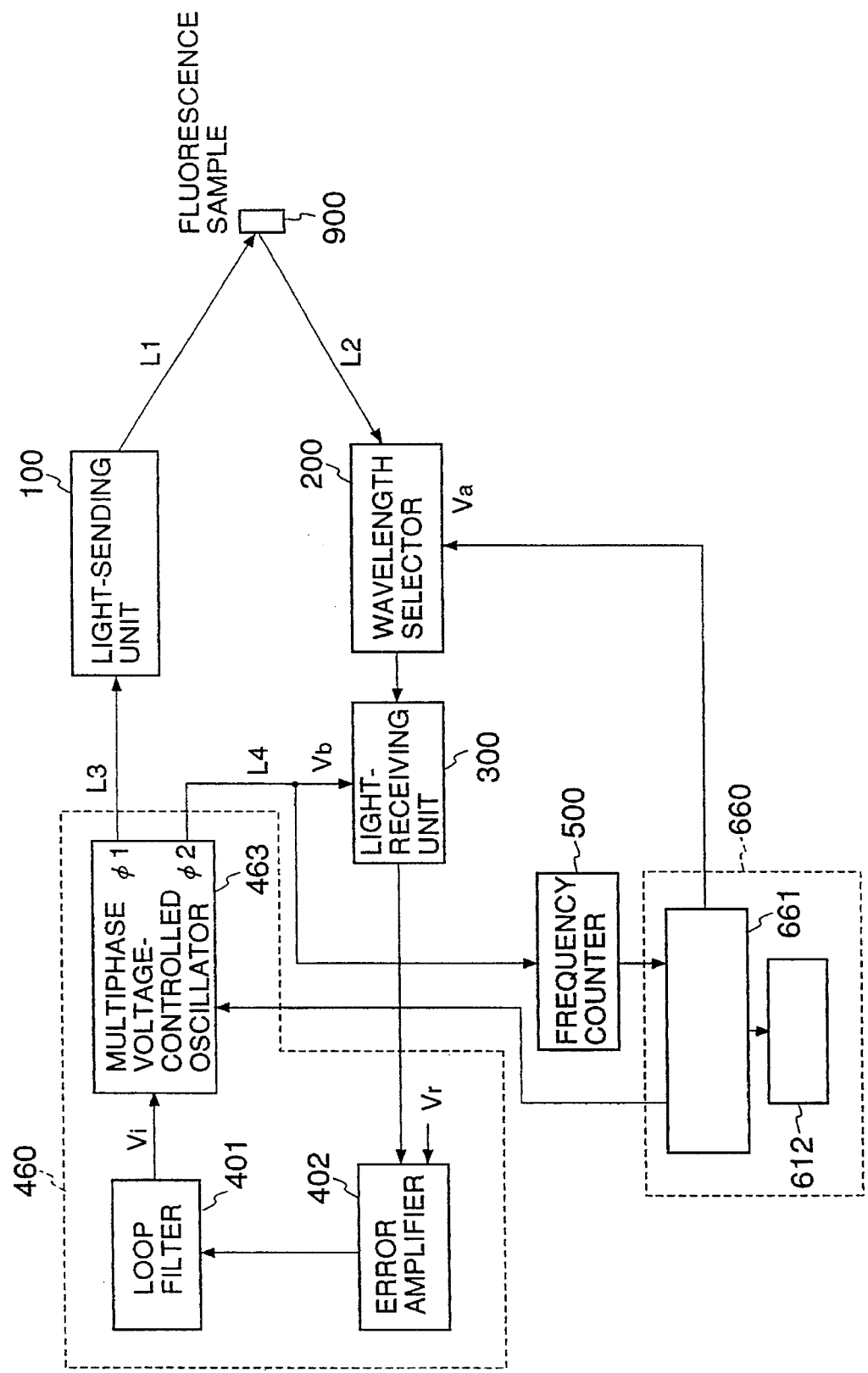
FIG. 38 is a block diagram showing the arrangement of a decay characteristic measuring apparatus of the sixth embodiment.

FIG. 38 is a block diagram showing the arrangement of a decay characteristic measuring apparatus according to the sixth embodiment of the present invention. This apparatus is characterized in that an offset phase-locked loop is formed. As shown in FIG. 38, this apparatus comprises (a) a light-sending unit 100, (b) a wavelength selector 200, (c) a light-receiving unit 300, (d) a frequency adjustment unit 460, (e) a frequency counter 500, and (f) a processing unit 660. The light-sending unit 100 receives a modulation signal $V_M(t)$ from the outside and outputs an excitation light beam $I_{EX}(t)$ having a wavelength=$\lambda_1$, which is intensity-modulated with the modulation signal $V_M(t)$, to a target measurement object 900. The wavelength selector 200 receives a reaction light beam $I_{RC}(t+\Phi_1+\Phi_2)$ having a wavelength=$\lambda_2$, which is generated on the target measurement object 900 when the excitation light beam $I_{EX}(t)$ output from the light-sending unit 100 is irradiated on the target measurement object 900, and a scattered light beam $I_{RF}(t+\Phi_1)$ obtained upon scattering of the excitation light beam $I_{EX}(t)$ on the target measurement object 900, and selects and outputs one of the light beams in accordance with a designation from the processing unit 660. The light-receiving unit 300 receives the modulation signal $V_M(t)$ and the light beam output from the wavelength selector 200, generates a current signal corresponding to the product of the intensity of the received light beam ($I_{RC}(t+\Phi_1+\Phi_2)$ or $I_{RF}(t+\Phi_1)$) and the modulation signal $V_M(t)$, and thereafter, outputs a voltage signal containing only an almost DC component. The frequency adjustment unit 460 outputs two modulation signals each having a frequency corresponding to the voltage value of the almost DC voltage signal output from the light-receiving unit 300, and having a phase difference designated by the processing unit 660. The frequency counter 500 measures the frequency of the modulation signal output from the frequency adjustment unit 460. The processing unit 660 outputs a wavelength selection designation signal for designating the selected wavelength ($\lambda_1$ or $\lambda_2$) to the wavelength selector 200. At the same time, the processing unit 660 reads the measurement value of the frequency counter 500 when a reference voltage value (Vr) input to an error amplifier 402 is set to "0 V", and the voltage value of the DC voltage signal output from the light-receiving unit 300 becomes almost "0 V" upon selection of the wavelength=$\lambda_1$. A phase difference $\Phi_1$ between the modulation signal $V_M(t)$ and the scattered light beam $I_{RF}(t+\Phi_1)$ is obtained from the read value. The processing unit 660 reads the measurement value of the frequency counter 500 when the voltage value of the DC voltage signal output from the light-receiving unit 300 becomes almost "0 V" upon selection of the wavelength=$\lambda_2$. A phase difference ($\Phi_1+\Phi_2$) between the modulation signal $V_M(t)$ and the reaction light beam $I_{RC}(t+\Phi_1+\Phi_2)$ is obtained from the read value. The processing unit 600 obtains the decay characteristics of the reaction light beam from the two phase differences, i.e., $\Phi_2$.

The frequency adjustment unit 460 comprises ① the error amplifier 402, ② a loop filter 401, and ③ a multiphase voltage-controlled oscillator 463. The error amplifier 402 receives a DC voltage output signal from the light-receiving unit 300, amplifies the difference to the reference voltage (Vr), and outputs the signal. The loop filter 401 receives the output from the error amplifier 402 and passes only the almost DC component. The multiphase voltage-controlled oscillator 463 outputs two modulation signals each having a frequency corresponding to the voltage value of the DC voltage signal output from the loop filter 401, and having a phase difference designated by the processing unit 660. The sum of group delay times generated in optical paths L1 and L2 and an electrical signal path L3 is set to be equal to the group delay time generated in an electrical signal path L4.

The processing unit 660 comprises ① an arithmetic processing unit 661 and ② a display unit 612. The arithmetic processing unit 661 issues a wavelength selection designation signal to the wavelength selector 200. At the same time, the arithmetic processing unit 661 reads the measurement value of the frequency counter 500, obtains phase differences between the intensity-modulated scattered and reaction light beams and the modulation signal, and thereafter, calculates the decay characteristics of the reaction light beam. The display unit 612 displays the calculation result from the arithmetic processing unit 661 in accordance with a designation from the arithmetic processing unit 661. The multiphase voltage-controlled oscillator 463 can change the frequency by voltage control as in the voltage-controlled oscillator 403. However, the multiphase voltage-controlled oscillator 463 has two outputs having the same frequency and a predetermined phase difference ($\Phi_2-\Phi_1$).

The apparatus of this embodiment outputs the decay characteristics of a reaction light beam in the following manner. For the descriptive convenience, group delay times in the electrical signal paths and the optical paths among the light-sending unit 100, the wavelength selector 200, and the light-receiving unit 300 are neglected.

Prior to actual measurement, a bias regulator 340 is adjusted to set the average value of a voltage signal output from a current-to-voltage converter 320, which voltage signal is an output from the light-receiving unit 300, is set to almost "0 V". At the same time, the processing unit 660 sets the phase difference ($\Phi_2-\Phi_1$) between the two signals output from the multiphase voltage-controlled oscillator 463 to a predetermined value within a range of 120° to 150°. Subsequently, an excitation light beam is output from the light-sending unit 100, and actual measurement is started. Thereafter, measurement is executed to measure the decay characteristics of the reaction light beam, as in the first embodiment.

In this apparatus, the delay time in the measurement system cannot be calibrated by the scattered component of the excitation light beam. For this reason, a target measurement object whose characteristics are known well must be used for time calibration.

The phase difference ($\Phi_2-\Phi_1$) between the two signals output from the multiphase voltage-controlled oscillator 463 is set within a range of 120° to 150°. However, the phase difference ($\Phi_2-\Phi_1$) between the two signals output from the multiphase voltage-controlled oscillator 463 can be set within a range of 30° to 60°, and an output on the $\Phi_2$ side can be supplied to the light-receiving unit 300 through a 90° phase shifter.

(Seventh Embodiment)

Figure 39:
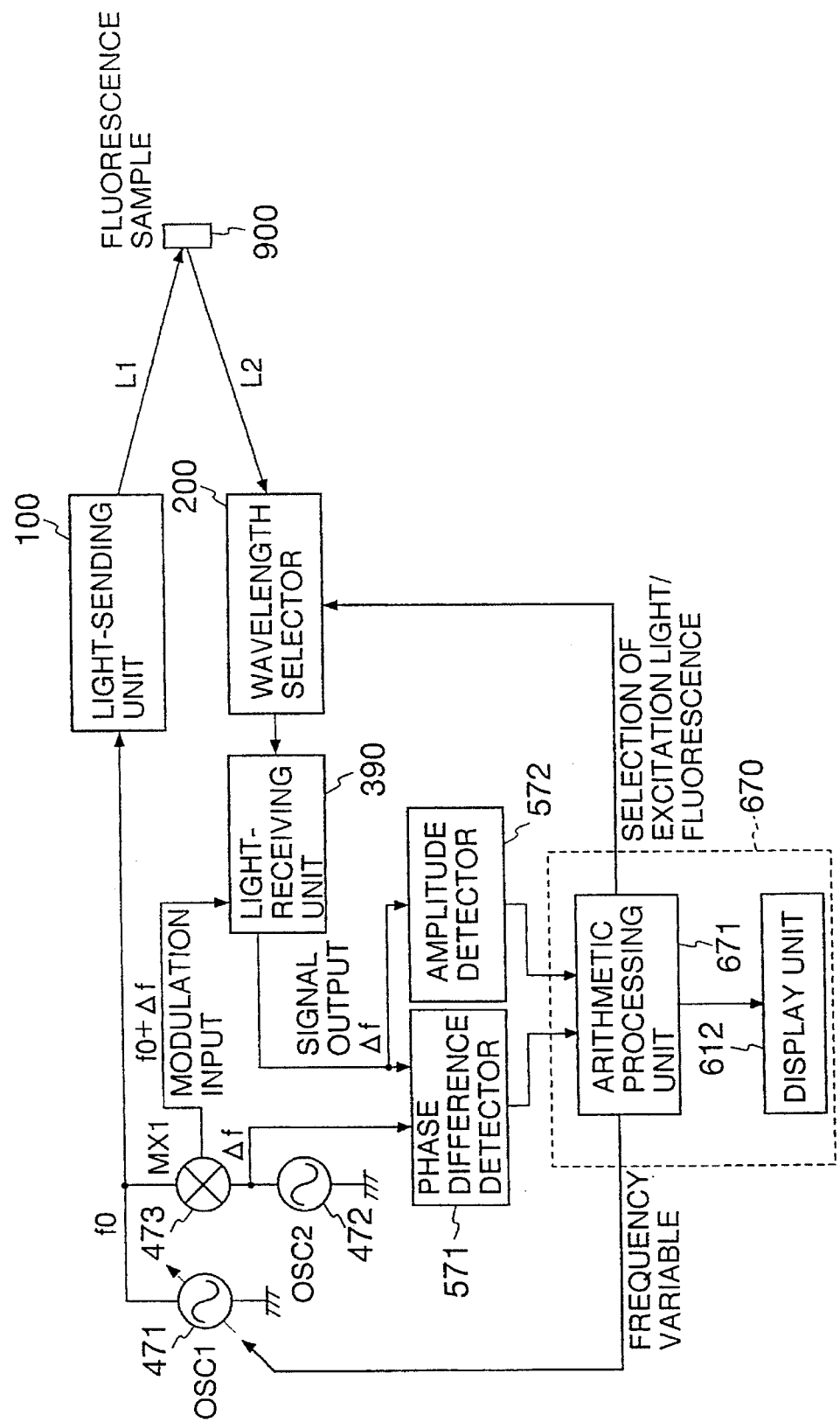
FIG. 39 is a block diagram showing the arrangement of a decay characteristic measuring apparatus of the seventh embodiment.

FIG. 39 is a block diagram showing the arrangement of a decay characteristic measuring apparatus according to the seventh embodiment of the present invention. In each of the above embodiments, the modulation frequency of an excitation light beam is equal to that of the photoconductive photodetector. In this embodiment, however, the applied voltage frequency of the photoconductive photodetector is different from the intensity modulation frequency of the excitation light beam (i.e., intensity modulation frequency of a scattered light beam or a reaction light beam incident on photoconductive photodetector). The light-receiving unit is operated as a frequency converter, and the phase difference and amplitude are measured by a beaten-down frequency. In this apparatus, the frequency is temporarily converted into a low frequency of 100 kHz or less for easy processing, and thereafter, the phase difference between electrical signals is detected, unlike a method of directly comparing the phase difference between incident light and an applied voltage of the photodetector.

As shown in FIG. 39, the apparatus of this embodiment comprises (a) a variable frequency oscillator 471, (b) an oscillator 472, (c) single-sideband mixer 473, (d) a light-sending unit 100, (e) a wavelength selector 200, (f) a light-receiving unit 390: (g) a phase difference detector 571, (h) an amplitude detector 572, and (i) a processing unit 670. The variable frequency oscillator 471 outputs an oscillation signal having a frequency (f0) corresponding to a designation from the processing unit 670. The oscillator 472 outputs an oscillation signal having a frequency $\Delta f$ (100 kHz or less). The single-sideband mixer 473 receives the oscillation signal output from the variable frequency oscillator 471 and the oscillation signal output from the oscillator 472 and outputs a modulation signal having a frequency=f0+$\Delta f$. The light-sending unit 100 receives the modulation signal from the variable frequency oscillator 471 and outputs an excitation light beam $I_{EX}(t)$ having a wavelength=$\lambda_1$, which is intensity-modulated with the modulation signal, to a target measurement object 900. The wavelength selector 200 receives a reaction light beam and a scattered light beam, and selects and outputs one of the light beams in accordance with a designation from the outside. The light-receiving unit 390 receives the modulation signal output from the single-sideband mixer 473 and the light beam output from the wavelength selector 200, generates a current signal corresponding to the product of the intensity of the received light and the modulation signal, and thereafter, selects and outputs a signal having the frequency $\Delta f$ corresponding to the difference between the frequency of the received light beam and the frequency of the modulation signal output from the single-sideband mixer 473. The phase difference detector 571 detects the phase difference between the phase of the signal output from the light-receiving unit 390 and the phase of the output signal from the oscillator 472. The amplitude detector 572 detects the amplitude value of the signal output from the light-receiving unit 390. The processing unit 670 outputs an oscillation frequency designation signal to the variable frequency oscillator 471 and a wavelength selection designation signal for designating the selected wavelength ($\lambda_1$ r $\lambda_2$) to the wavelength selector 200. At the same time, the processing unit 670 reads the phase difference detected by the phase difference detector 571 and the amplitude value detected by the amplitude detector 572. When the wavelength=$\lambda_1$ is selected, a phase difference $\Phi_1$ between a modulation signal $V_M(t)$ and a scattered light beam $I_{RF}(t+\Phi_1)$ is obtained. When the wavelength=$\lambda_2$ is selected, a phase difference ($\Phi_1+\Phi_2$) between the modulation signal $V_M(t)$ and a reaction light beam $I_{RC}(t+\Phi_1+\Phi_2)$ is obtained. The processing unit 600 obtains the decay characteristics of the reaction light beam in accordance with the two phase differences, i.e. $\Phi_2$.

Figure 40:
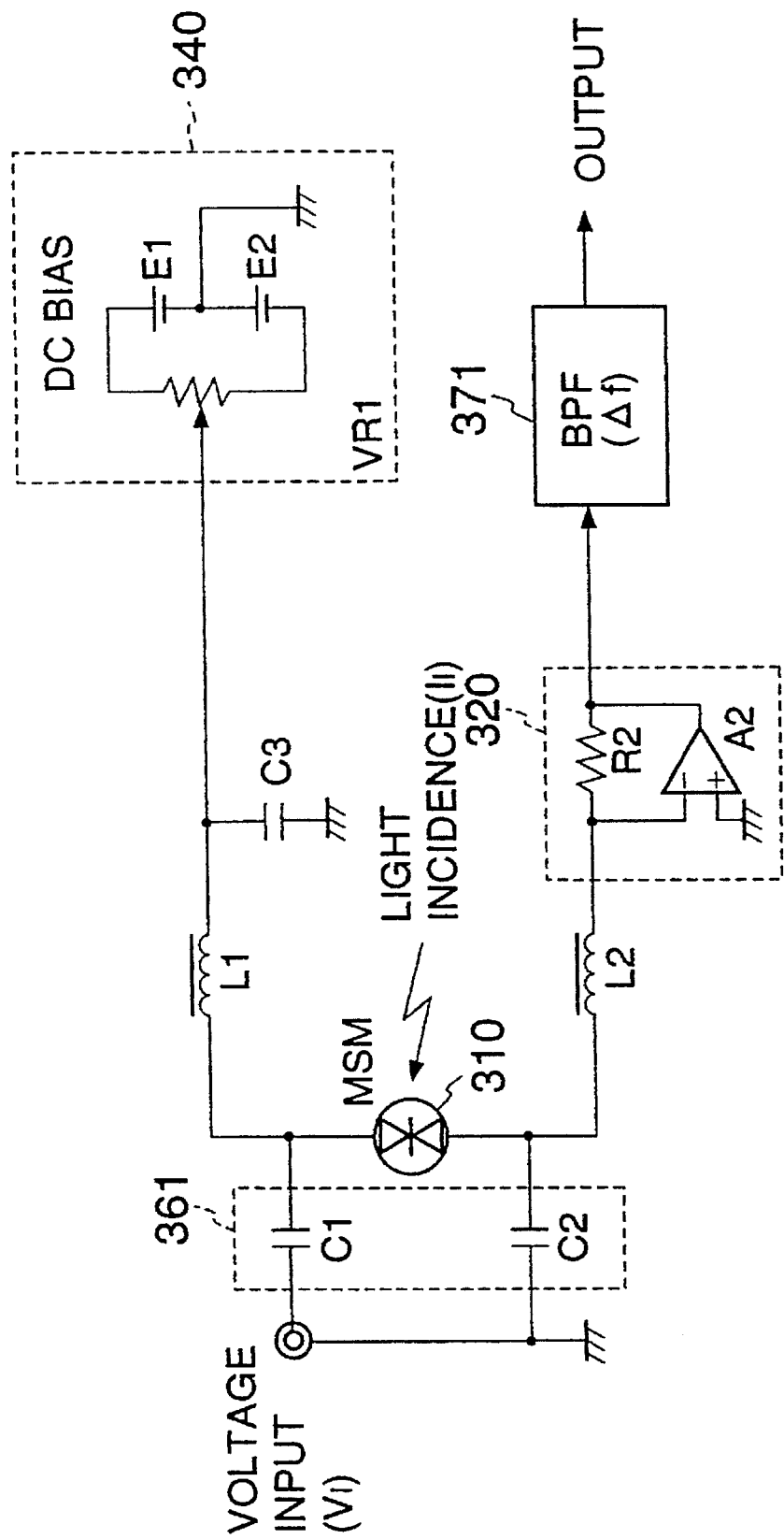
FIG. 40 is a block diagram showing the arrangement of a light-receiving unit of the seventh embodiment.

FIG. 40 is a block diagram showing the arrangement of the light-receiving unit 390. As shown in FIG. 40, the light-receiving unit 390 is constituted by ① a photoconductive photodetector 310, ② a voltage application unit 361, ③ choke coils L1 and L2, ④ a current-to-voltage converter 320, ⑤ a bandpass filter 371, and ⑥ a bias regulator 340. The photoconductive photodetector 310 receives an optical signal ($I_l$) and a voltage signal ($V_l$) and calculates the product of the optical signal and the voltage signal, thereby outputting a current signal reflecting the phase difference between the received light beam and the modulation signal. The voltage application unit 361 is constituted by connecting capacitors C1 and C2 for applying a voltage signal corresponding to the AC component of the voltage signal to the photoconductive photodetector 310. The choke coils L1 and L2 pass the low frequency component of a current generated in the photoconductive photodetector 310. The current-to-voltage converter 320 converts the AC component of the current signal flowing through the choke coil L1, the photoconductive photodetector 310, and the choke coil L2 into a voltage. The bandpass filter 371 selects and outputs a component of the voltage signal output from the current-to-voltage converter 320, which almost has a frequency Δf. The bias regulator 340 regulates the bias value of the voltage applied to the photoconductive photodetector 310. That is, the light-receiving unit 390 is equivalent to the light-receiving unit 300 shown in FIG. 2, in which the low-pass filter 330 is replaced with the bandpass filter 371.

The apparatus of this embodiment measures the decay characteristics of a reaction light beam in the following manner.

Prior to actual measurement, the bias regulator 340 is adjusted to set the average value of a voltage signal output from the current-to-voltage converter 320, which voltage signal is an output from the light-receiving unit 300, to almost "0 V". Subsequently, an excitation light is output from each lock system.

The single-sideband mixer 473 receives a signal generated by the oscillator 472 for generating a fixed low frequency (Δf) of 100 kHz or less and a signal generated by the variable frequency oscillator 471 whose oscillation frequency is designated by the processing unit 670, and supplies an output signal having a frequency=f0+Δf to the photoconductive photodetector 310 of the light-receiving unit 390. The generated signal from the variable frequency oscillator 471 is supplied to the single-sideband mixer 473, and at the same time, to the light-sending unit 100. The light-sending unit 100 irradiates an excitation light beam which is intensity-modulated in accordance with the signal supplied from the variable frequency oscillator 471 on the target measurement object 900. The excitation light scattered component and the reaction light (fluorescence) component from the target measurement object 900 are supplied to the wavelength selector 200 whose transmission frequency is designated by the processing unit 670. One of the components is guided to the light-receiving unit 390 in accordance with a designation.

The conversion gain of the photoconductive photodetector 310 depends on the applied voltage and is modulated with the frequency=f0+Δf. Therefore, in the photoconductive photodetectors the frequency (f0+Δf) of the applied voltage is mixed with the intensity modulation frequency (f0) of the incident light. The signal component having a frequency=2f0+Δf and the signal component having a frequency=Δf are generated as a current signal flowing through the photoconductive photodetector 310 and output from the current-to-voltage converter 320 connected to the photoconductive photodetector 310 as a voltage signal. Of the signal output from the current-to-voltage converter 320, a beaten-down signal component (frequency=Δf) is selected by the bandpass filter 371 and output. The beaten-down signal preserves the phase difference information between the modulation signal from the light-sending unit 100 and the scattered light beam or the reaction light beam and an amplitude proportional to the intensity modulation amplitude of the scattered light beam or the reaction light beam.

The beaten-down signal is supplied to the phase difference detector 571 and the amplitude detector 572. The phase difference detector 571 simultaneously receives an output signal from the oscillator 472, detects the phase difference between the output signal from the oscillator 472 and the beaten-down signal, and notifies the processing unit 670 of it. This phase difference reflects the phase difference between the modulation signal from the light-sending unit 100 and the scattered light beam or the reaction light beam. The amplitude detector 572 detects the amplitude value of the beaten-down signal and notifies the processing unit 670 of it.

In actual measurement, the processing unit 670 designates the oscillation frequency f0 to the variable frequency oscillator 471, and also designates the wavelength selector 200 to select the wavelength=$\lambda_1$. In this state, the phase difference $\Phi_1$ generated by the sum of group delay times in the optical paths L1 and L2, the light-sending unit 100, and the light-receiving unit 390 is measured. At the same time, a received intensity modulation amplitude component A1 is measured. These measurement results are recorded in the processing unit 670.

The processing unit 670 designates the wavelength selector 200 to select the wavelength=$\lambda_2$ without changing setting of the variable frequency oscillator 471. In this state, the phase difference ($\Phi_1+\Phi_2$) generated by the sum of group delay times in the optical paths L1 and L2, the light-sending unit 100, and the light-receiving unit 390 is measured. At the same time, a received intensity modulation amplitude component A2 is measured. These measurement results are recorded in the processing unit 670. Subsequently, the processing unit 670 obtains a phase difference ($\Phi_2-\Phi_1$) and a relative intensity (A2/A1) from the above recorded results.

The processing unit 670 sequentially changes the oscillation frequency designation to the variable frequency oscillator 471, thereby repeatedly performing the same measurement as described above. In this manner, the phase difference and relative intensity at each frequency can be obtained, and the decay characteristics of the target measurement object 900 can be measured.

(Eighth Embodiment)

Figure 41:
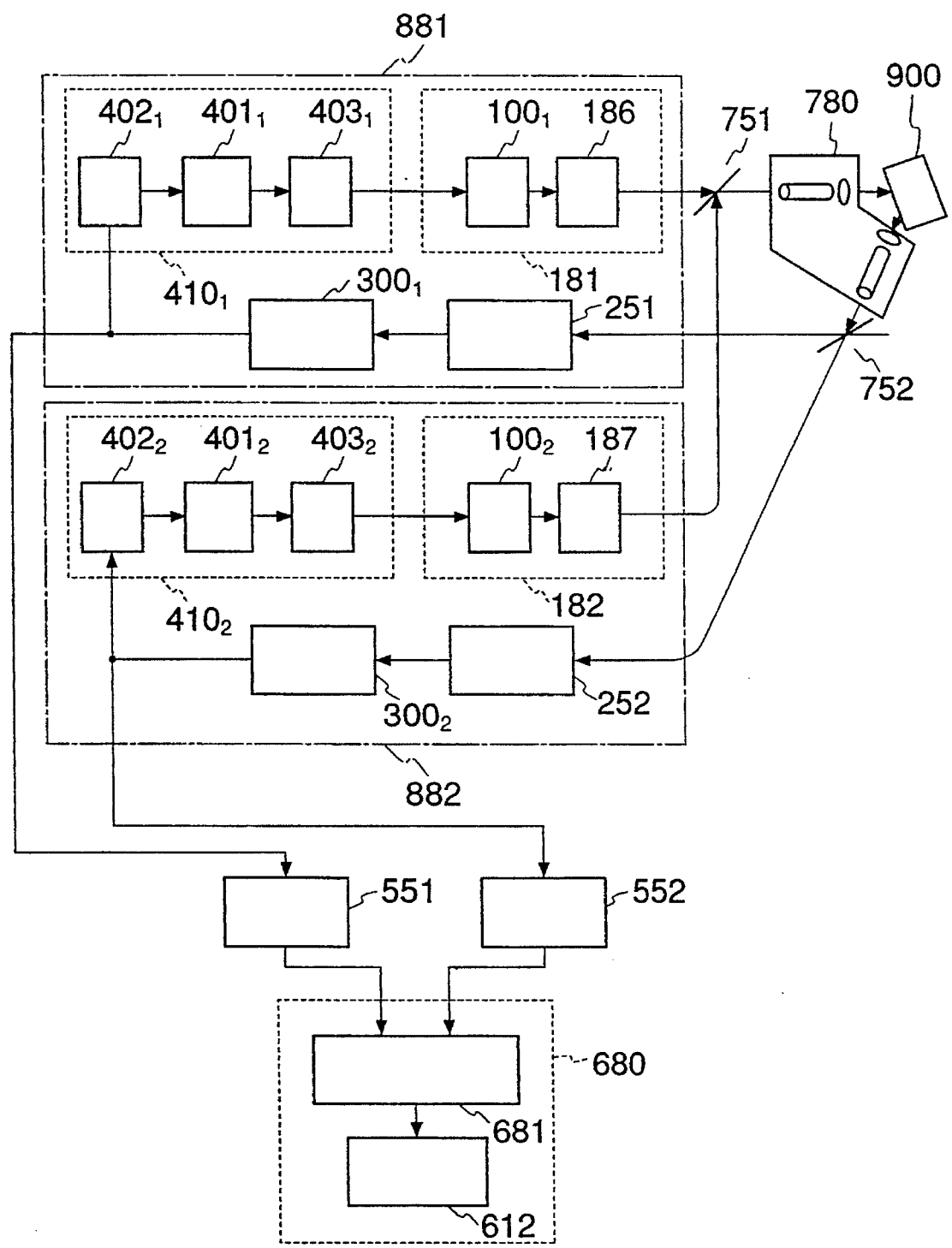
FIG. 41 is a block diagram showing the arrangement of a decay characteristic measuring apparatus of the eighth embodiment.

FIG. 41 is a block diagram showing the arrangement of a decay characteristic measuring apparatus according to the eighth embodiment of the present invention. In this apparatus, the present invention is applied to a system for discriminating a cell (e.g., a system disclosed in "R. R. Alfano et al., SPIE vol. 1599 Recent Advances in the Uses of Light in Physics, Chemistry, Engineering, and Medicine, pp. 284–289 (1991)).

As shown in FIG. 41, this apparatus comprises (a) a lock system 881, (b) a lock system 882, (c) a frequency counter 551, (d) a frequency counter 552, (e) a processing unit 680, (f) a multiplexing mirror 751, (g) a light guide 780, and (h) a branching mirror 752. The lock system 881 forms a phase-locked loop associated with a scattered light beam. The lock system 882 forms a phase-locked loop associated with a reaction light beam. The frequency counter 551 monitors and measures the frequency of a modulation signal in the lock system 881. The frequency counter 552 monitors and measures the frequency of a modulation signal in the lock system 882. The processing unit 680 reads the measurement value of the frequency counter 551 when the lock system 881 forms the phase-locked loop, reads the measurement value of the frequency counter 552 when the lock system 882 forms the phase-locked loop, and obtains the decay characteristics of the reaction light beam on the basis of the read measurement values. The multiplexing mirror 751 multiplexes part of an excitation light beam output from the lock system 881 and part of an excitation light beam output from the lock system 882 and outputs the light beam to a target measurement object 900. The light guide 780 guides the excitation light beam aligned by the multiplexing mirror 751 to the target measurement object 900, and at the same time, guides the scattered light beam and the reaction light beam from the target measurement object 900. The branching mirror 752 receives the light beam output from the light guide 780 and branches the light beam into two light beams containing a scattered light component and a reaction light component.

The lock system 881 is different from the lock system 800 of the first embodiment in that ① the light-sending unit 100 of the first embodiment is replaced with an SHG element 186 for generating the second harmonic of a light beam output from the light-sending unit 100, thereby constituting a light-sending unit 181, and ② the wavelength selector 200 is replaced with a wavelength selector 251 for selectively transmitting a light beam having a wavelength=$\lambda_1$. The lock system 882 is different from the lock system 800 of the first embodiment in that ① the light-sending unit 100 of the first embodiment is replaced with an SHG element 187 for generating the second harmonic of a light beam output from the light-sending unit 100, thereby constituting a light-sending unit 182, and ② the wavelength selector 200 is replaced with a wavelength selector 252 for selectively transmitting a light beam having a wavelength=$\lambda_2$.

The apparatus of this embodiment operates as in the first embodiment. More specifically, the oscillation frequencies of voltage-controlled oscillators $403_1$ and $403_2$ are controlled such that the phase differences between the light-sending units 181 and 182 and light-receiving units $300_1$ and $300_2$ are kept to a predetermined value ($\pi/2$). The fluorescence decay time of the target measurement object 900 is specified from the frequency, thereby discriminating a cancer cell from a normal cell.

The operation of the apparatus of this embodiment will be described below in detail.

An excitation light beam (wavelength=315 nm) is irradiated on the target measurement object 900 from the distal end of the light guide 780 incorporated in, e.g., a fiberscope toward cells. Of the excitation light beam, a scattered component and fluorescence (wavelength=330 to 440 nm) from the surface of the target measurement object 900 pass through the light guide 780 and are guided to the light-receiving units $300_1$ and $300_2$ through the wavelength selectors 251 and 252. A distance L3 between the distal end of the light guide 780 and the target measurement object 900 can be considered to frequently change. For this reason, the two lock systems 881 and 882 are prepared to increase the measurement period. The excitation light beam used for measurement is obtained by passing an output light beam from a laser diode for emitting a light beam having a wavelength=630 nm through the SHG crystals 186 and 187 for generating second harmonics. Distances L1 and L2 in the light guide 780 are set to 1 m, the refractive index is set to 1.5, the distance L3 between the distal end of the light guide 780 and the target measurement object 900 is set to 10 cm, and the refractive index of the optical path is set to 1.0. When the group delay times in the light-sending units 181 and 182, the light-receiving units $300_1$ and $300_2$; the wavelength selectors 251 and 252, and the light guide coupling optical system in the light-sending and light-receiving units are neglected, a value f1 obtained by the frequency counter 551 is represented as follows in accordance with equation (4):

$$f1 = ((4/3) \times (2 \times 1.5 + 0.2)/3 \times 10^8)$$
$$= 70.3125 \text{ MHz}$$

According to R. R. Alfano et al., the fluorescence decay characteristics of a cell are approximated by two decay time constants. Of the fluorescence from a cancer cell, the average value of smaller fluorescence decay time constants is 1.913 ns, and of the fluorescence from a normal cell, the average value of smaller fluorescence decay time constants is 1.12 ns. Although not described, a cancer cell and a normal cell are considered to have almost the same large decay time constant. In the apparatus of this embodiment, measurement cannot be performed while separating the two time constants. However, in accordance with a change in phase difference between an excitation light beam and fluorescence, which is caused by the different time constants for a normal cell and a cancer cell, a value obtained by the frequency counter 552 changes, which allows discrimination between the normal cell and the cancer cell.

If the distance L3 varies in accordance with the movement of the sample or fiberscope, the indication value of the frequency counter 552 varies even for the same target measurement object. However, by using the simultaneously obtained value f1, only the phase difference of the sample can be extracted in accordance with equation (17). For the descriptive convenience, the large time constant is neglected. In this case, a value f2 is specified in accordance with the following equation which is obtained from equations (17), (10), and (11):

$$\tan[(3/4) \times 2\pi \times (1-(f2/(70.3125 \times 10^6)))] = 2\pi \times f2 \times \tau$$

When the time constant of the cell is substituted into $\tau$, the frequency f2 obtained for a normal cell is 64 MHz, and the frequency f2 obtained for a cancer cell is 60.9 MHz. In consideration of the resolving power of the apparatus of this embodiment, the normal cell and the cancer cell can sufficiently be discriminated from each other.

As has been described above in detail, according to the decay characteristic measuring apparatus of the present invention, a photoconductive photodetector capable of performing a high-speed operation and having characteristics representing a small dependency on an incident light amount is used to execute high-speed calculation, and an electric circuit at a subsequent stage processes a relatively slow signal. For this reason, the resolving power of decay characteristic measurement can be largely increased.

More specifically, according to the present invention, variations in phase of an output, which are observed in use of an electronic mixer and caused by variations in input amplitude, can be prevented. When photoconductive photodetector with high-speed response is used as a photodetector, the usable frequency range can be largely increased, thereby improving the degree of freedom for selection of a measurement target.

Even when a high sensitivity and saturation for a strong disturbance signal are taken into consideration, no noise-free amplifier having a large dynamic range is required. In addition, no disturbance optical signal is supplied to the first-stage amplifier. For this reason, saturation of the first-stage amplifier need not be particularly taken into consideration. Therefore, the gain of the first-stage amplifier can be maximized within an allowance of the S/N ratio and the dynamic range for the signal component. The degree of freedom for design can be large, and a measurement system with a high sensitivity can be easily arranged.

Unlike the conventional system, even when a lot of modulation components other than a signal component are contained in background light stronger than signal light, the modulation components other than the signal component are not supplied to the first-stage amplifier. Therefore, a countermeasure for this situation need not be particularly taken.

In a normal system for performing phase comparison between electrical signals, an amplifier having a band to the modulation frequency is required. However, a system for directly performing phase comparison between incident light and an electrical signal, as in the present invention, only requires an amplifier having a low frequency band, which is used as a loop filter in a PLL. Therefore, a simple circuit arrangement can be obtained.

In a system wherein phase difference information is converted into a frequency and read out, the resolving power is limited by the precision of a frequency counter. Therefore, measurement at a high resolving power can be performed.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

The basic Japanese Application No. 223628/1994 filed on Sep. 19, 1994 is hereby incorporated by reference.

What is claimed is:

1. A decay characteristic measuring apparatus comprising:

a light-sending unit for irradiating a first light beam having a first wavelength on a target measurement object, the first light beam being intensity-modulated with a first electrical signal changed in accordance with a first frequency, and having an intensity periodically changed in accordance with the first frequency;

a wavelength selector for receiving a second light beam as a scattered light beam of the first light beam on said target measurement object, and a third light beam having a second wavelength, the third light beam being generated on said target measurement object upon irradiation of the first light beam output from said light-sending unit on said target measurement object, and selecting and outputting one of the second and third light beams in accordance with a designation from an outside;

a light-receiving unit, having a photodetector for receiving a second electrical signal controlling a photoelectric conversion gain and having a second frequency, receiving the light beam output from said wavelength selector, and generating a third electrical signal containing a component having a third frequency corresponding to an absolute value of a difference between the first frequency and the second frequency, the third electrical signal being an electrical signal corresponding to a received light intensity and the set photoelectric conversion gain, for outputting a fourth signal reflecting the component of the third frequency from the third electrical signal; and a measurement processing unit for outputting the first electrical signal to said light-sending unit, outputting the second electrical signal to said light-receiving unit, outputting a wavelength selection designation signal for designating a selected wavelength to said wavelength selector, and obtaining decay characteristics of the third light beam from a first measurement result of the fourth signal output from said light-receiving unit upon selection of the first wavelength and a second measurement result of the fourth signal output from said light-receiving unit upon selection of the second wavelength, on the basis of a phase difference between a phase of a change in intensity of the second light beam supplied to said light-receiving unit and a phase of a change in intensity of the third light beam supplied to said light-receiving unit.

2. An apparatus according to claim 1, wherein said light-receiving unit comprises a signal supplying unit for receiving an electrical signal, converting the electrical signal into a predetermined output form, and outputting the electrical signal, a photoconductive photodetector, having an electrical signal application terminal for receiving the electrical signal output from said signal supplying unit, for receiving a light beam, a conversion amplification unit for outputting a voltage signal corresponding to the electrical signal flowing through said photoconductive photodetector, and a frequency selector for receiving the voltage signal output from said conversion amplification unit, and selecting and passing a voltage signal having substantially the same frequency as that corresponding to an absolute value of a difference between a frequency of a change in intensity of the light beam incident on said photoconductive photodetector and a frequency of the electrical signal supplied to said signal supplying unit.

3. An apparatus according to claim 2, wherein the predetermined output form is a voltage signal output in a low output impedance state.

4. An apparatus according to claim 3, wherein, for said photoconductive photodetector, when a target measurement light intensity is constant, and an applied voltage value is an independent variable, a current amount flowing through said photoconductive photodetector is represented by a substantial odd function of the applied voltage within a predetermined domain including an applied voltage value of 0 V, and when the applied voltage is constant, and the target measurement light intensity is an independent variable, the current amount flowing through said photoconductive photodetector is represented by a substantial linear function of an irradiation signal intensity within a predetermined domain of the target measurement light intensity, and the voltage signal applied to said photoconductive photodetector is periodic and has a time average value of substantially zero, in which an amplitude is represented by a substantial even function of a time when a middle point between adjacent times where the amplitude becomes zero is defined as an origin.

5. An apparatus according to claim 2, wherein the predetermined output form is a current signal output in a high output impedance state.

6. An apparatus according to claim 5, wherein, for said photoconductive photodetector, when a target measurement light intensity is constant, and an applied current value is an independent variable, a voltage value generated across said photoconductive photodetector is represented by a substantial odd function of the applied current within a predetermined domain including an applied current value of 0 A, and when the applied current is constant, and the target measurement light intensity is an independent variable, the voltage value generated across said photoconductive photodetector is represented by a substantial linear function of an irradiation signal intensity within a predetermined domain of the target measurement light intensity, and a non-DC component of the current signal applied to said photoconductive photodetector is periodic and has a time average value of substantially zero, in which an amplitude is represented by a substantial even function of a time when a middle point between adjacent times where the amplitude of the non-DC component becomes zero is defined as an origin.

7. An apparatus according to claim 2, further comprising bias regulating means for adjusting an operating point of said photoconductive photodetector.

8. An apparatus according to claim 2, wherein said photoconductive photodetector is a metal-semiconductor-metal photodetector having a structure wherein rectifier junctions are connected in opposite directions.

9. An apparatus according to claim 2, wherein said photoconductive photodetector is a photodetector having a structure wherein ohmic contact electrodes are connected to oppose each other.

10. An apparatus according to claim 1, wherein the first frequency is equal to the second frequency, and the phase difference between the first electrical signal and the second electrical signal is known, and said measurement processing unit comprises a frequency adjustment unit for adjusting the first frequency to maintain a condition for fixing the output signal from said light-receiving unit to a reference value, a frequency measurement device for measuring the first frequency adjusted and fixed by said frequency adjustment unit, and an arithmetic processing unit for calculating a first phase difference corresponding to a difference between the phase of the change in intensity of the second light beam at a position of said photodetector and a phase of a change in amplitude of the first electrical signal from a first measurement frequency measured by said frequency measurement device when the second light beam is selected by said wavelength selector, calculating a second phase difference corresponding to a difference between the phase of the change in intensity of the third light beam at the position of said photodetector and a phase of a change in amplitude of the first electrical signal from a second measurement frequency measured by said frequency measurement device when the third light beam is selected by said wavelength selector, and obtaining the decay characteristics of the third light beam on the basis of the first phase difference and the second phase difference.

11. An apparatus according to claim 10, wherein the fourth signal is a voltage signal, the reference value is 0 V, and the difference between the phase of the change in intensity of the second light beam at the position of said photodetector and the phase of the change in amplitude of the second electrical signal when the first frequency fixed by said frequency adjustment unit is the first measurement frequency, and the difference between the phase of the change in intensity of the third light beam at the position of said photodetector and the phase of the change in amplitude of the second electrical signal when the first frequency fixed by said frequency adjustment unit is the second measurement frequency are one of $\pi/2$ and $3\pi/2$.

12. An apparatus according to claim 1, wherein the first frequency is different from the second frequency, and said measurement processing unit calculates the decay characteristics of the third light beam on the basis of measurement values of an amplitude and phase of the fourth signal.

13. A decay characteristic measuring apparatus comprising:

a first light-sending unit for irradiating a first light beam having a first wavelength on a target measurement object, the first light beam being intensity-modulated with a first electrical signal changed in accordance with a first frequency, and having an intensity periodically changed in accordance with the first frequency;

a first wavelength selector for selecting and outputting a second light beam as a scattered light beam of the first light beam on said target measurement object;

a first light-receiving unit, having a first photodetector for receiving a second electrical signal controlling a photoelectric conversion gain and having a second frequency, receiving the light beam transmitted through said wavelength selector and output from said first wavelength selector, and generating a third electrical signal containing a component having a third frequency corresponding to an absolute value of a difference between the first frequency and the second frequency, the third electrical signal being an electrical signal corresponding to a received light intensity and the photoelectric conversion gain, for outputting a fourth signal reflecting an amplitude value of the component of the third frequency from the third electrical signal;

a second light-sending unit for irradiating a third light beam having the first wavelength on said target measurement object, the third light beam being intensity-modulated with a fifth electrical signal changed in accordance with a fourth frequency, and having an intensity periodically changed in accordance with the fourth frequency;

a second wavelength selector for selecting and outputting a fourth light beam having a second wavelength, the fourth light beam being generated on said target measurement object upon irradiation of the third light beam output from said second light-sending unit on said target measurement object;

a second light-receiving unit, having a second photodetector for receiving a sixth electrical signal controlling the photoelectric conversion gain and having a fifth frequency, receiving the light beam transmitted through said second wavelength selector, and generating a seventh electrical signal containing a component having a sixth frequency corresponding to an absolute value of a difference between the fourth frequency and the fifth frequency, the seventh electrical signal being an electrical signal corresponding to the received light intensity and the photoelectric conversion gain, for outputting an eighth signal reflecting an amplitude value of the component of the sixth frequency from the seventh electrical signal; and a measurement processing unit for outputting the first electrical signal to said first light-sending unit, outputting the second electrical signal to said first light-receiving unit, outputting the fifth electrical signal to said second light-sending unit, outputting the sixth electrical signal to said second light-receiving unit, and obtaining decay characteristics of the fourth light beam from a first measurement result of the fourth signal output from said first light-receiving unit and a second measurement result of the eighth signal output from said second light-receiving unit, on the basis of a phase difference between a phase of a change in intensity of the second light beam supplied to said first light-receiving unit, and a phase of a change in intensity of the fourth light beam supplied to said second light-receiving unit.

14. An apparatus according to claim 13, wherein each of said first and second light-receiving units comprises a signal supplying unit for receiving an electrical signal, converting the electrical signal into a predetermined output form, and outputting the electrical signal, a photoconductive photodetector, having an electrical signal application terminal for receiving the electrical signal output from said signal supplying unit, for receiving a light beam, a conversion amplification unit for outputting a voltage signal corresponding to the electrical signal flowing through said photoconductive photodetector, and a frequency selector for receiving the voltage signal output from said conversion amplification unit, and selecting and passing a voltage signal having substantially the same frequency as that corresponding to an absolute value of a difference between a frequency of a change in intensity of the light beam incident on said photoconductive photodetector and a frequency of the electrical signal supplied to said signal supplying unit.

15. An apparatus according to claim 14, wherein the predetermined output form is a voltage signal output in a low output impedance state.

16. An apparatus according to claim 15, wherein, for said photoconductive photodetector, when a target measurement light intensity is constant, and an applied voltage value is an independent variable, a current amount flowing through said photoconductive photodetector is represented by a substantial odd function of the applied voltage within a predetermined domain including an applied voltage value of 0 V, and when the applied voltage is constant, and the target measurement light intensity is an independent variable, the current amount flowing through said photoconductive photodetector is represented by a substantial linear function of an irradiation signal intensity within a predetermined domain of the target measurement light intensity, and the voltage signal applied to said photoconductive photodetector is periodic and has a time average value of substantially zero, in which an amplitude is represented by a substantial even function of a time when a middle point between adjacent times where the amplitude becomes zero is defined as an origin.

17. An apparatus according to claim 14, wherein the predetermined output form is a current signal output in a high output impedance state.

18. An apparatus according to claim 17, wherein, for said photoconductive photodetector, when a target measurement light intensity is constant, and an applied current value is an independent variable, a voltage value generated across said photoconductive photodetector is represented by a substantial odd function of the applied current within a predetermined domain including an applied current value of 0 A, and when the applied current is constant, and the target measurement light intensity is an independent variable, the voltage value generated across said photoconductive photodetector is represented by a substantial linear function of an irradiation signal intensity within a predetermined domain of the target measurement light intensity, and a non-DC component of the current signal applied to said photoconductive photodetector is periodic and has a time average value of substantially zero, in which an amplitude is represented by a substantial even function of a time when a middle point between adjacent times where the amplitude of the non-DC component becomes zero is defined as an origin.

19. An apparatus according to claim 14, further comprising bias regulating means for adjusting an operating point of said photoconductive photodetector.

20. An apparatus according to claim 14, wherein said photoconductive photodetector is a metal-semiconductor-metal photodetector having a structure wherein rectifier junctions are connected in opposite directions.

21. An apparatus according to claim 14, wherein said photoconductive photodetector is a photodetector having a structure wherein ohmic contact electrodes are connected to oppose each other.

22. An apparatus according to claim 13, wherein the first frequency is equal to the second frequency, the phase difference between the first electrical signal and the second electrical signal is known, the fourth frequency is equal to the fifth frequency, and the phase difference between the fifth electrical signal and the sixth electrical signal is known, and said measurement processing unit comprises a first frequency adjustment unit for adjusting the first frequency to maintain a condition for fixing the output signal from said first light-receiving unit to a reference value, a first frequency measurement device for measuring the first frequency adjusted and fixed by said first frequency adjustment unit, a second frequency adjustment unit for adjusting the fourth frequency to maintain a condition for fixing the output signal from said second light-receiving unit to a reference value, a second frequency measurement device for measuring the fourth frequency adjusted and fixed by said second frequency adjustment unit, and an arithmetic processing unit for calculating a first phase difference corresponding to a difference between the phase of the change in intensity of the second light beam at a position of said first photodetector and a phase of a change in amplitude of the first electrical signal from a first measurement frequency measured by said first frequency measurement device, calculating a second phase difference corresponding to a difference between the phase of the change in intensity of the fourth light beam at a position of said second photodetector and a phase of a change in amplitude of the fifth electrical signal from a second measurement frequency measured by said second frequency measurement device, and obtaining the decay characteristics of the fourth light beam on the basis of the first phase difference and the second phase difference.

23. An apparatus according to claim 22, wherein the fourth electrical signal and the eighth electrical signal are voltage signals, the reference value is 0 V, and the difference between the phase of the change in intensity of the second light beam at the position of said first photoconductor and the phase of the change in amplitude of the second electrical signal when the first frequency fixed by said first frequency adjustment unit is the first measurement frequency, and the difference between the phase of the change in intensity of the fourth light beam at the position of said second photodetector and the phase of the change in amplitude of the sixth electrical signal when the fourth frequency fixed by said second frequency adjustment unit is the second measurement frequency are one of $\pi/2$ and $3\pi/2$.

* * * * *